US012631638B2

(12) United States Patent
    Kviatkovskyi

(10) Patent No.: US 12,631,638 B2
(45) Date of Patent: May 19, 2026

(54) MULTI-COMPONENT SYSTEMS FOR DETECTING COVID FROM SPUTUM AND SALIVA

(71) Applicant: Dmytro Kviatkovskyi, Bootle (GB)

(72) Inventor: Dmytro Kviatkovskyi, Bootle (GB)

( * ) Notice: Subject to any disclaimer, the term of this patent is extended or adjusted under 35 U.S.C. 154(b) by 0 days.

(21) Appl. No.: 18/423,781

(22) Filed: Jan. 26, 2024

(65) Prior Publication Data

US 2024/0168019 A1     May 23, 2024

Related U.S. Application Data

(63) Continuation-in-part of application No. 17/975,105, filed on Oct. 27, 2022, now abandoned.

(60) Provisional application No. 63/294,909, filed on Dec. 30, 2021.

(51) Int. Cl.
     *G01N 33/569*      (2006.01)
     *G01N 33/68*       (2006.01)
     *G16H 40/67*       (2018.01)

(52) U.S. Cl.
     CPC ....... *G01N 33/56983* (2013.01); *G01N 33/68* (2013.01); *G16H 40/67* (2018.01); *G01N 2800/26* (2013.01)

(58) Field of Classification Search
     CPC ............. G01N 33/56983; G01N 33/68; G01N 2800/26; G16H 40/67

USPC ........................................................ 204/403.1
See application file for complete search history.

(56) References Cited

U.S. PATENT DOCUMENTS

2009/0061533 A1 *   3/2009  Minami  ........... G01N 33/54353
                                                   422/68.1
2021/0290974 A1 *   9/2021  Emerson  .............. A61N 5/0624

* cited by examiner

*Primary Examiner* — Charles Capozzi
*Assistant Examiner* — Jacqueline Brazin

(57)              ABSTRACT

Systems for determining COVID include a biosensor that interacts with a sputum sample and outputs the first and second signals; a wireless communication device; a memory device with detectors embedded in the memory device. The biosensor is configured to use two different biological components with the first and second biological components separated by a membrane. The concentration of the first biological component corresponds to the threshold for the first virus strain and the concentration of the second biological component corresponds to the threshold for the second virus strain. The memory device is configured to receive the first and second signals and set the first and second signal thresholds for each detector. The memory device identifies the presence of the first or second virus strain in response to detectors embedded in the memory device are detecting a value that is greater than or less than the first or second signal threshold.

12 Claims, 38 Drawing Sheets

| First biological component | Concentration of the first biological component | Limit values (thresholds) |
|---|---|---|
| <ul><li>proteins</li><li>antibodies</li><li>lipids</li><li>enzymes</li><li>reagents</li><li>polymers</li><li>aptamers</li><li>DNA or RNA molecules</li><li>microbial cells</li><li>cell receptors</li><li>a biomolecule dye</li></ul> | corresponds to the limit values (thresholds) for the first SARS-CoV-2 virus strain | for the first SARS-CoV-2 virus strain |
| Second biological component | Concentration of the second biological component | Limit values (thresholds) |
| <ul><li>proteins</li><li>antibodies</li><li>lipids</li><li>enzymes</li><li>reagents</li><li>polymers</li><li>aptamers</li><li>DNA or RNA molecules</li><li>microbial cells</li><li>cell receptors</li><li>a biomolecule dye</li></ul> | corresponds to the limit values (thresholds) for the second SARS-CoV-2 virus strain | for the second SARS-CoV-2 virus strain |

FIG. 3

| First biological component | Concentration of the first biological component | Limit values (thresholds) |
|---|---|---|
| Proteins | 65% | for the Delta SARS-CoV-2 virus strain |
| Second biological component | Concentration of the second biological component | Limit values (thresholds) |
| Antibodies | 48% | for the Omicron SARS-CoV-2 virus strain |

*FIG. 4*

DETERMINING BY A CONTROLLER A FIRST THRESHOLD OF A SENSOR —1001

DETERMINING BY A CONTROLLER A SECOND THRESHOLD OF A SENSOR —1002

DETECTING A VALUE GREATER THAN THE FIRST THRESHOLD OR LESS THAN THE SECOND THRESHOLD —1003

TRANSMITTING THE INDICATION TO ANOTHER DEVICE —1004

DETERMINING BY A CONTROLLER A FIRST THRESHOLD OF A SENSOR ──1101

DETERMINING BY A CONTROLLER A SECOND THRESHOLD OF A SENSOR ──1102

DETECTING A FIRST VALUE GREATER THAN OR LESS THAN THE FIRST THRESHOLD AND DETECTING A SECOND VALUE GREATER THAN OR LESS THAN THE SECOND THRESHOLD ──1103

TRANSMITTING THE INDICATION TO ANOTHER DEVICE ──1104

| | COVID | Alpha | B.1.1.7 | Beta | Gamma | Delta | Lambda | Mu | Epsilon | Zeta | Theta | Eta | Iota | Kappa | B.1.1.207 | B.1.1.317 | B.1.616 | B.1.618 | B.1.1.529 |
|---|---|---|---|---|---|---|---|---|---|---|---|---|---|---|---|---|---|---|---|
| RT-PCR | | | | | | | | | | | | | | | | | | | |
| Nucleic acid test | | | | | | | | | | | | | | | | | | | |
| Serological test | | | | | | | | | | | | | | | | | | | |
| CRISPR | | | | | | | | | | | | | | | | | | | |
| INAA | | | | | | | | | | | | | | | | | | | |
| DPCR | | | | | | | | | | | | | | | | | | | |
| Microarray analysis | | | | | | | | | | | | | | | | | | | |
| NGS | | | | | | | | | | | | | | | | | | | |
| Antigen test | | | | | | | | | | | | | | | | | | | |
| RDT | | | | | | | | | | | | | | | | | | | |
| ELISAT | | | | | | | | | | | | | | | | | | | |
| Neutralization assay | | | | | | | | | | | | | | | | | | | |
| CI | | | | | | | | | | | | | | | | | | | |
| Chest CT scans | | | | | | | | | | | | | | | | | | | |
| Body temperature | | | | | | | | | | | | | | | | | | | |
| Blood oxygen level | | | | | | | | | | | | | | | | | | | |
| Cough | | | | | | | | | | | | | | | | | | | |
| Sputum | | | | | | | | | | | | | | | | | | | |
| Shortness of breath | | | | | | | | | | | | | | | | | | | |
| Fever | | | | | | | | | | | | | | | | | | | |
| Anosmia | | | | | | | | | | | | | | | | | | | |
| Ageusia | | | | | | | | | | | | | | | | | | | |
| Nasal congestion | | | | | | | | | | | | | | | | | | | |
| Runny nose | | | | | | | | | | | | | | | | | | | |
| Sore throat | | | | | | | | | | | | | | | | | | | |
| Muscle pain | | | | | | | | | | | | | | | | | | | |
| Joint pain | | | | | | | | | | | | | | | | | | | |
| Headache | | | | | | | | | | | | | | | | | | | |
| Fatigue | | | | | | | | | | | | | | | | | | | |
| Abdominal pain | | | | | | | | | | | | | | | | | | | |
| Vomiting | | | | | | | | | | | | | | | | | | | |
| Diarrhea | | | | | | | | | | | | | | | | | | | |
| Diabetes | | | | | | | | | | | | | | | | | | | |
| Lung diseases | | | | | | | | | | | | | | | | | | | |
| Cardiovascular diseases | | | | | | | | | | | | | | | | | | | |
| Ischemia | | | | | | | | | | | | | | | | | | | |
| Hypertension | | | | | | | | | | | | | | | | | | | |

| Differential №1 | | Differential №2 | | Differential №3 | | Differential №4 | | Differential №5 | |
|---|---|---|---|---|---|---|---|---|---|
| Value of differential №1 | Accurate value №1 | Value of differential №2 | Accurate value №2 | Value of differential №3 | Accurate value №3 | Value of differential №4 | Accurate value №4 | Value of differential №5 | Accurate value №5 |
| 3 | 5 | 26 | 3 | 7 | 6 | 22 | 3 | 12 | 1 |
| -5 | 6 | 6 | 3 | -3 | 3 | -3 | 4 | -5 | 1 |
| 15 | 5 | 3 | 6 | -11 | 2 | 0 | 4 | -8 | 1 |
| 2 | 2 | 45 | 2 | 14 | 2 | 5 | 4 | 12 | 1 |
| -12 | 6 | -12 | 5 | 18 | 3 | 4 | 3 | -3 | 3 |
| 6 | 6 | -2 | 5 | 8 | 3 | 14 | 3 | -7 | 1 |

15b

| Symptoms | |
|---|---|
| Shortness of breath | Shortness of breath |
| Sweating | Fatigue and weakness |
| Chills | Cough |
| Fatigue | Rapid heartbeat |
| Headache | Change in urine production |
| Muscle pain | Nausea |
| | Loss of appetite |
| | Decreased alertness |
| | Increase of respiration rate |
| Complex symptoms | |
| Fever | Fatigue |
| | Shortness of breath |
| Differentials | |
| Value of differential №1 / accurate value №1 | Value of differential №1 / accurate value №1 |
| Value of differential №2 / accurate value №2 | Value of differential №2 / accurate value №2 |
| Value of differential №3 / accurate value №3 | Value of differential №3 / accurate value №3 |
| Value of differential №4 / accurate value №4 | Value of differential №4 / accurate value №4 |
| Value of differential №5 / accurate value №5 | Value of differential №5 / accurate value №5 |
| Value of differential №6 / accurate value №6 | Value of differential №6 / accurate value №6 |
| | Value of differential №7 / accurate value №7 |
| | Value of differential №8 / accurate value №8 |
| | Value of differential №9 / accurate value №9 |

| Symptom | Weighting coefficient №1 | Weighting coefficient №2 | Weighting coefficient №3 | Weighting coefficient №4 | Weighting coefficient №5 |
|---|---|---|---|---|---|
| Fever | 3 | 5 | 4 | 6 | 1 |
| Chills | 4 | 6 | 5 | 3 | 1 |
| Cough | 4 | 6 | 5 | 2 | 1 |
| Difficulty breathing | 4 | 5 | 6 | 2 | 1 |
| Nasal congestion | 4 | 6 | 5 | 3 | 1 |
| Loss of taste | 4 | 5 | 6 | 3 | 1 |
| Sore throat | 4 | 2 | 5 | 6 | 1 |
| Loss of smell | 4 | 6 | 5 | 2 | 1 |
| Headache | 4 | 6 | 3 | 5 | 1 |
| Muscle aches | 4 | 2 | 6 | 5 | 1 |

16b

| Frequency of symptom in metric | Value of differential №1 / accurate value №1 | Value of differential №2 / accurate value №2 | Value of differential №3 / accurate value №3 | Value of differential №4 / accurate value №4 | Value of differential №5 / accurate value №5 |
|---|---|---|---|---|---|
| Presence of 3 symptoms of Delta strain | Yes | Yes | No | Yes | Yes |
| Presence of 4 symptoms of Delta strain | Yes | Yes | No | No | Yes |
| Presence of 5 symptoms of Delta strain | No | Yes | No | No | No |

16c

| Symptom | Value of differential | Accurate value | Symptom | Value of differential | Accurate value |
|---|---|---|---|---|---|
| Fever | 3 | 3 | Cough | 22 | 9 |
| | -5 | 1 | | -12 | 1 |
| | 15 | 6 | | 3 | 2 |
| | 45 | 8 | | 24 | 9 |
| | -12 | 1 | | 21 | 9 |
| | -1 | 1 | | 3 | 1 |
| Fatigue | 16 | 7 | Dyspnea | 35 | 6 |
| | 21 | 9 | | -11 | 1 |
| | 3 | 1 | | -1 | 1 |
| | -2 | 1 | | 13 | 4 |
| | 10 | 4 | | 17 | 6 |
| | -5 | 1 | | -2 | 1 |
| Anosmia | 13 | 4 | Ageusia | 19 | 7 |
| | 18 | 6 | | 3 | 2 |
| | -2 | 1 | | 43 | 8 |
| | 11 | 4 | | 23 | 7 |
| | -2 | 1 | | -12 | 1 |
| | 32 | 8 | | 2 | 2 |

| Value of differential | Groups of differentials | |
|---|---|---|
| | Group | Values of differential |
| -3 | Group №1 | -3, -11, -5, -12 |
| -11 | Group №2 | 14, 3, 12, 15, 2, 6 |
| 14 | Group №3 | 14, 15 |
| 3 | Group №4 | -12, 15 |
| 12 | | |
| -5 | | |
| 15 | | |
| 2 | | |
| -12 | | |
| 6 | | |

17b

| Symptom | Groups of symptoms | |
|---|---|---|
| | Group | Symptoms |
| Fever | Group №1 | Chills, fatigue, muscle pain |
| Shortness of breath | Group №2 | Cough, fever, headache, sweating |
| Sweating | Group №3 | Rapid heartbeat, increase of respiration rate, shortness of breath |
| Fatigue | Group №4 | Nausea, loss of appetite |
| Chills | | |
| Cough | | |
| Rapid heartbeat | | |
| Headache | | |
| Muscle pain | | |
| Nausea | | |
| Loss of appetite | | |
| Increase of respiration rate | | |

17c

| Symptom | Weighting coefficient |
|---|---|
| Fever | 3 |
| Shortness of breath | 4 |
| Sweating | 6 |
| Fatigue | 4 |
| Chills | 4 |
| Cough | 3 |
| Rapid heartbeat | 4 |
| Headache | 4 |
| Muscle pain | 5 |
| Nausea | 5 |
| Loss of appetite | 2 |
| Increase of respiration rate | 3 |

17d

| Symptoms | Complex symptoms | Correlation of several symptoms |
|---|---|---|
| Fever | Fever | Rapid heartbeat, headache, muscle pain, fatigue |
| Shortness of breath | Shortness of breath | Cough, chills, increase of respiration rate, sweating |
| Sweating | | |
| Fatigue | | |
| Chills | | |
| Cough | | |
| Rapid heartbeat | | |
| Headache | | |
| Muscle pain | | |
| Nausea | | |
| Loss of appetite | | |
| Increase of respiration rate | | |

MULTI-COMPONENT SYSTEMS FOR DETECTING COVID FROM SPUTUM AND SALIVA

BACKGROUND OF THE INVENTION

Field of the Invention

The present invention relates to diagnosing an individual's health using technical means, and more particularly, to sensor systems for detecting viral infections, e.g., new mutated COVID variants.

Description of the Related Art

Coronavirus disease 2019 or COVID-19 (original SARS-CoV-2 virus strain) and the many thousands of SARS-CoV-2 virus strains have spread worldwide, leading to an ongoing global pandemic. The COVID pandemic has swept the entire world, becoming a fundamental global tragedy, as it is virtually impossible to isolate oneself from the virus. Viruses tend to mutate, and SARS-CoV-2 virus strain is no exception. As a consequence, severe acute respiratory syndrome coronavirus SARS-CoV-2 has many variants. Original SARS-CoV-2 virus strain is an RNA virus, i.e., it has molecules of ribonucleic acid (RNA) as its genetic material. Each time the virus copies itself, the RNA sequence may change, which causes mutations. The virus' traits, such as its contagiousness and lethality, also change. Currently, there are thousands of coronavirus strains.

At the end of November 2021, new dangerous variant emerged—B.1.1.529, which received the name Omicron and it has been assessed as highly dangerous by the World Health Organization. The WHO supposes that, after a few mutations, all current diagnostic means, vaccines, and coronavirus drugs may become ineffective against the Omicron variant. The Omicron variant has been found to better evade antibodies than the Delta variant, which is now the most widespread COVID variant in the world. The Omicron variant has more than 50 mutations from the original SARS-CoV-2 virus strain, and most mutations are in the gene encoding the spike protein, which is the target of most vaccines.

Over time, other very dangerous mutated SARS-CoV-2 virus strains have sprouted up all around the world. These new variants have a different chromosomal genome structure, behave differently, and affect different vital organs in the human body, such as the new Brazilian variant or new Centaurus variant, which were first detected in July 2022. In August 2022, a new Deltacron variant, which is a hybrid of variants Delta and Omicron, was first detected in Russia. The detection of the Pirola variant in the UK first became known on Aug. 18, 2023. The new Pirola variant of the coronavirus has a number of additional mutations compared to the previously identified Omicron variants, and is more contagious than its predecessors.

Therefore, we are facing a unique and tragic reality, in which original SARS-CoV-2 virus strain is constantly mutating, spawning new autonomous variants that may be even more hazardous for people than the original variant. While many SARS-CoV-2 virus strains have vaccines, they do not exist in quantities that might be needed and may not be located where an outbreak of a new mutated SARS-CoV-2 virus strain was to occur. Though lockdown was an effective tool, it cannot be implemented for a longer duration if every country and its economy is to function normally. Therefore, there remains a need to develop modern systems for detecting new SARS-CoV-2 virus strains with a mutated genome. Timely detection of new SARS-CoV-2 virus strains and their effective treatment is possible only if a viral disease is diagnosed comprehensively and systematically, using new methods for detecting new SARS-CoV-2 virus strains. A number of existing drawbacks of the modern medical practice can be overcome using the proposed multi-component systems of the present invention for detecting new mutated SARS-CoV-2 virus strains from human sputum and saliva samples.

SUMMARY OF THE INVENTION

The system for determining COVID disease in a person comprises a biosensor utilizing two different biological components that interacts with sputum and saliva samples and outputs the first and second signals; a wireless communication device configured to communicate using a wireless peer-to-peer or machine-type-communication protocol; a memory device with detectors integrated in the memory device configured to receive the first and second signals from the biosensor using one or more detectors integrated into the memory device. The sputum and saliva samples include a nasal swab, nasopharyngeal swab, throat swab, deep airway material, saliva. In some aspects, the biosensor includes a microfluidic chip that allows only small sputum or saliva molecules to pass through to the biosensor and does not allow large molecules to pass through. In some aspects, the biosensor uses graphene coatings for binding to the sputum and saliva samples.

The biosensor of present invention is configured to include the first biological component that represents proteins and the second biological component. The second biological component within the biosensor may be lipids, antibodies, enzymes, reagents, polymers, DNA or RNA molecules, microbial cells, cell receptors, a biomolecule dye, etc. The first biological component and the second biological component are coupled to the same transducer within the biosensor. The first biological component and the second biological component are separated from each other by a membrane (e.g., a semi-permeable membrane, multilayer membrane, graphene membrane, ceramic membrane, iron membrane, silicone membrane, Teflon membrane, polymer membrane, rubber membrane, glass membrane, quartz membrane.)

The concentration of the first biological component corresponds to the threshold for the first SARS-CoV-2 virus strain, and the concentration of the second biological component corresponds to the threshold for the second SARS-CoV-2 virus strain with a mutated virus genome code. The first biological component and the second biological components interact with the sputum and saliva samples and change the chemical structure of the sputum and saliva samples. The biosensor outputs a first signal when the first biological component interacts with the sputum and saliva samples and changes the chemical structure of the sputum and saliva samples, and outputs a second signal when the second biological component interacts with the sputum and saliva samples and changes the chemical structure of the sputum and saliva samples. The first and second signals that the biosensor generates are electrical, magnetic or optical signals.

The memory device then receives the first signal and the second signal from the biosensor using one or more detectors integrated into the memory device. One or more detectors integrated into the memory device (e.g., micro temperature sensors, electrochemical immunosensors, atomic magnetometers (AM), spectrometers, fluorescence microscope, molecular electric transducer (MET), etc.) decrypt the first and second signals into values. Each detector is embedded in the memory device and coupled to the wireless communication device via the detector output. The memory device is coupled to the wireless communication device and configured to determine respective thresholds for each detector integrated into the memory device, identify that the person has the first or second SARS-CoV-2 virus strain in response to the detector are detecting a value that is greater than or less than the respective thresholds for each detector, and transmit an indication that the person has contracted the SARS-CoV-2 virus strain, via the wireless communication device, to another device.

In some aspects, the memory device controller using the controller command decoder determines a first signal threshold and a second signal threshold for each of the one or more detectors integrated into the memory device. The memory device transmits the indication to the wireless communication device via the detector output responsive to a determination that a value detected by the detector is greater than or less than the first respective threshold and responsive to a determination that a value detected by the detector is greater than or less than the second respective threshold. In some aspects, the memory device controller updates the first signal threshold and second signal threshold for each of the one or more detectors integrated into the memory device based on the detected change in the electrical, magnetic, and/or optical characteristics of the sputum and saliva samples. In some aspects, the memory device controller updates the first signal threshold and second signal threshold for each of the one or more detectors integrated into the memory device based on the detected change in the temperature characteristic and characteristic of relative molecular motion of the sputum and saliva samples.

The system of present invention may further comprise a plurality of sensors that gather symptom data values from the person representing their COVID disease symptoms, and a workstation with a computer or any equivalent gadgets that are embedded with machine learning and artificial intelligence techniques applied to signal data and the symptom data values to detect tendencies confirming indication that the person has contracted the SARS-CoV-2 virus strain. The tendencies are shown on a display through graphs and charts using multiple colors. The symptom data values are biochemical and biophysical data and represent COVID symptoms of person that may be respiratory symptoms (cough, sputum, shortness of breath, fever, anosmia (loss of smell), ageusia (loss of taste), nasal congestion, runny nose, sore throat), musculoskeletal symptoms (muscle pain, joint pain, headache, fatigue), digestive symptoms (abdominal pain, vomiting, diarrhea), physiological diseases (diabetes, lung diseases, cardiovascular diseases, ischemia, hypertension.)

These and other systems, methods, objects, features, and advantages of the present invention will be apparent to those skilled in the art from the following detailed description of the preferred embodiment and the drawings.

Additional features and advantages of the invention will be set forth in the description that follows, and in part will be apparent from the description, or may be learned by practice using the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed. All documents mentioned herein are hereby incorporated in their entirety by reference.

BRIEF DESCRIPTION OF THE ATTACHED FIGURES

The accompanying drawings, which are included to provide a further understanding of the invention and are incorporated in and constitute a part of this specification, illustrate embodiments of the invention and, together with the description, serve to explain the principles of the invention.

In the drawings:

FIG. 3 illustrates an example of the composition of two different biological components within the biosensor.

FIG. 4 illustrates another example of the composition of two different biological components within the biosensor.

FIG. 14 illustrates an example of a metric of differentials according to a first embodiment of the invention.

FIG. 15 illustrates examples of the metrics of differentials according to a second embodiment of the invention.

FIG. 16 illustrates examples of the metrics of differentials according to a third embodiment of the invention.

FIG. 17 illustrates examples of the metrics of differentials according to a fourth embodiment of the invention.

DETAILED DESCRIPTION OF THE PREFERRED EMBODIMENTS

Figure 1:
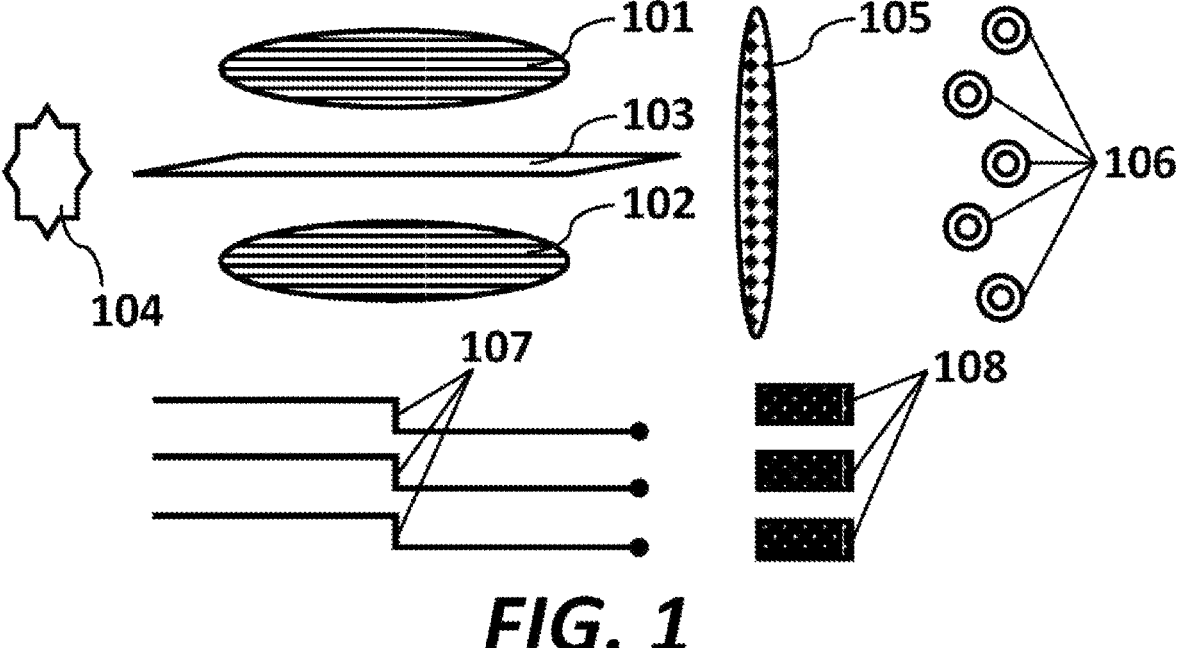
FIG. 1 illustrates components of the biosensor utilizing two different biological components for implementing the invention.

Reference will now be made in detail to the preferred embodiments of the present invention, examples of which are illustrated in the accompanying drawings.

The invention relates to systems for detecting, analyzing, and diagnosing new COVID variants. Below are the main terms used in the present invention.

A virus is an infectious agent that replicates inside the living cells of an organism and infects all life forms, from plants and animals to humans. Examples of common human diseases caused by viruses include the common cold, influenza, chickenpox, and cold sores. Many serious diseases such as rabies, Ebola virus disease, AIDS (HIV), avian influenza, and SARS are caused by viruses. Viruses spread in many ways. Many viruses, including influenza viruses, SARS-CoV-2, chickenpox, smallpox, and measles, spread in the air by coughing and sneezing.

Coronaviruses are a group of related RNA viruses that cause severe acute respiratory syndrome diseases. COVID-19 is a viral disease caused by severe acute respiratory syndrome coronavirus 2 (SARS-CoV-2). The COVID-19 is the original SARS-CoV-2 virus strain, which is the base for new SARS-CoV-2 virus strains having a changed (mutated) virus genome code.

Major SARS-CoV-2 virus strains include the SARS-CoV-2 virus strains of concern currently recognized by the World Health Organization, SARS-CoV-2 virus strains of interest which are or were recognized by the World Health Organization, other notable SARS-CoV-2 virus strains. SARS-CoV-2 virus strains of concern—Alpha (lineage B.1.1.7), B.1.1.7 with E484K, Beta (lineage B.1.351), Gamma (lineage P.1), Delta (lineage B.1.617.2). SARS-CoV-2 virus strains of interest—Lambda (lineage C.37), Mu (lineage B.1.621), Epsilon (lineages B.1.429, B.1.427, CAL.20C), Zeta (lineage P.2), Theta (lineage P.3), Eta (lineage B.1.525), Iota (lineage B.1.526), Kappa (lineage B.1.617.1), Omicron (lineage B.1.1.529). Other notable SARS-CoV-2 virus strains—Lineage B.1.1.207, Lineage B.1.1.317, Lineage B.1.616, Lineage B.1.618, Brazilian variant, Centaurus variant, Deltacron variant.

Predetermined symptom threshold values for SARS-CoV-2 virus strains are predetermined actual limits for specific symptoms provided in medical literature, which, when exceeded, show that the person has been infected by a COVID disease. Medical guidelines are well established, documented in medical literature, and famous scientific facts, which indicate predetermined symptom threshold values for SARS-CoV-2 virus strains.

A differential is a positive or negative difference between the values of the patient's biochemical and biophysical data obtained and predetermined symptom threshold values for SARS-CoV-2 virus strains.

Correlation is any mathematical or logical relationship (dependence) between two random variables that is based on causation. A tendency is a special case of correlation and shows a possible direction among random variables.

Sensors include the devices which collect the patient's biochemical and biophysical data for detecting respiratory symptoms (cough, sputum, shortness of breath, fever, anosmia (loss of smell), ageusia (loss of taste), nasal congestion, runny nose, sore throat), musculoskeletal symptoms (muscle pain, joint pain, headache, fatigue), digestive symptoms (abdominal pain, vomiting, diarrhea), physiological diseases (diabetes, lung diseases, cardiovascular diseases, ischemia, hypertension.)

Biosensors are analytical devices which convert a biological response into an electrical, magnetic or optical signal and combine a biological component with a physicochemical detector. The sensitive biological element, e.g., tissue, microorganisms, organelles, cell receptors, enzymes, antibodies, nucleic acids, etc., is a biologically derived material or biomimetic component that interacts with, binds with, or recognizes the analyte (the sputum or saliva sample) under study.

Laboratory medical tests include the reverse transcription polymerase chain reaction (RT-PCR) test, nucleic acid test, serological test, molecular test CRISPR, isothermal nucleic acid amplification, digital polymerase chain reaction, microarray analysis, next-generation sequencing, antigen tests for antigen proteins, rapid diagnostic test, enzyme-linked immunosorbent assay test, neutralization assay, chemiluminescent immunoassay, etc. Laboratory medical examinations include chest CT scans, checking for elevated body temperature, checking for low blood oxygen levels, etc.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized, and that structural and logical changes may be made without departing from the spirit and scope of the present invention. The following detailed description is, therefore, not to be taken in a limiting sense, and the scope of the present invention is defined by the appended claims and their equivalents.

Figure 2:
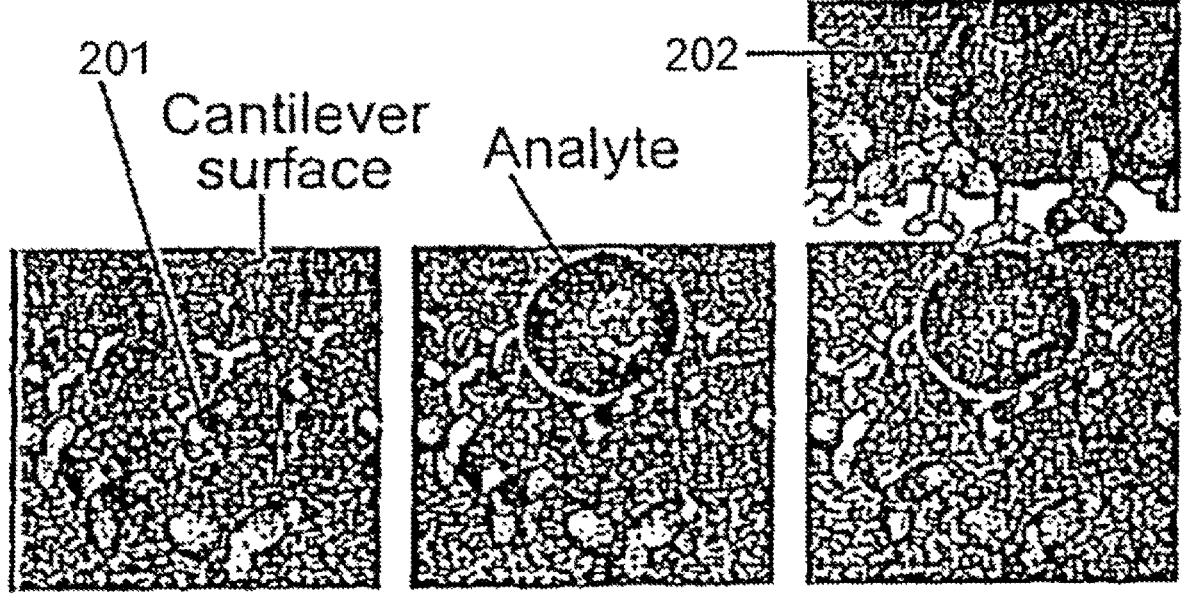
FIG. 2 is a diagram the operation of the biosensor utilizing two different biological components.

FIGS. 1-2 illustrate components and the operation of the biosensor utilizing two different biological components for implementing the present invention. In general, a biosensor is an analytical device which converts a biological response into a signal and combines a biological component with a physicochemical detector. The biologically responsive material, e.g., proteins, lipids, antibodies, enzymes, reagents, polymers, DNA or RNA molecules, microbial cells, cell receptors, a biomolecule dye, etc., is a biomimetic component that interacts with, binds with, or recognizes the analyte (sputum or saliva sample) under study. The types of biological samples of a person that can be used for collection of the person's symptom data values may include a nasal swab, nasopharyngeal swab, throat swab, deep airway material, saliva.

The types of biosensors of the present invention use the chemical or biological agent that generates a reaction of: 1) heat output (or heat absorption) by the reaction (calorimetric biosensor), 2) changes in distribution of charges causing an electrical potential to be produced (potentiometric biosensor), 3) movement of electrons produced within a redox (reduction oxidation) reaction (amperometric biosensor), 4) light output during a reaction or a light absorbance difference between the reactants and products (optical biosensors), 5) effects observed due to the mass of the reactants (piezo electric biosensor.)

It will be understood that various other types of biological or chemical sensors may be employed within the scope of the present invention. For example, the biosensors can produce an electrical signal detectable by the sensors (e.g., an electrochemical immunosensors.) In some aspects, the signal may be magnetic or optical (e.g., fluorescent emission.) If a biosensor outputs a magnetic signal as data, then sensors based on the atomic magnetometer (AM) are used to receive and register it. Optical sensors (e.g., a spectrometer or a fluorescence microscope) are used to register and analyze the fluorescent signal.

The present invention proposes to use specially developed the biosensor utilizing two different biological components. Biosensors of the present invention have two different biological components (e.g., proteins, lipids, antibodies, enzymes, reagents, polymers, DNA or RNA molecules, microbial cells, cell receptors, a biomolecule dye, etc.) that are separated by a membrane and coupled to a transducer or amplifier. Common to all types of biosensors utilizing two different biological components are recognition elements used as the first or second biological component: proteins, immunoglobulins (antibodies), enzymes (or homogenates of microbial cells), nucleic acids (DNA, RNA, PNA), microbial cells (microorganisms) and cell receptors.

As shown in FIG. 1, the biosensor utilizing two different biological components, where the first biological component 101 includes proteins. The first biological component 101 and second biological component 102 are separated by a membrane 103 (e.g., a semi-permeable membrane, multilayer membrane, graphene membrane, ceramic membrane, iron membrane, silicone membrane, Teflon membrane, polymer membrane, rubber membrane, glass membrane, quartz membrane, etc.) The first biological component and the second biological component are coupled to the same transducer 104 within the biosensor. The biosensor may include a microfluidic chip 105 that allows only small sputum or saliva molecules to pass through to the biosensor and does not allow large molecules to pass through.

The first biological component (proteins) 101 and second biological component (e.g., lipids, antibodies, enzymes, reagents, polymers, DNA or RNA molecules, microbial cells, cell receptors, a biomolecule dye, etc.) 102 interact with, binds with, or recognizes the sputum and saliva samples (the analyte) under study. As a result of a change in the chemical composition of sputum and saliva samples, reactions are formed when the first and second biological components chemically interact with sputum or saliva molecules 106. These reactions are determined and sensed by a transducer 104 which converts it to signals 107 (e.g., an electrical, magnetic, and/or optical signal). The sensors 108 will then receive, decipher and analyze the data on signals from the biosensor.

As shown in FIG. 2, for each SARS-CoV-2 virus strain to be identified, specific molecules will be identified. A protein 201 capable of recognizing a target substance will then be generated for each specific molecule and these proteins will be contained in the biosensor utilizing two different biological components. The sputum and saliva samples will be delivered to the biosensor and moved past the proteins. The proteins 201 will bind to the target molecules to be identified in the sputum solution. Thereafter, beads 202 will be brought past the biosensor. The beads 202 have covalently bound proteins that attach to the target molecules. The number of beads may be counted by sensors. The number of beads will indicate the concentration of the target molecules.

FIGS. 3-4 illustrate examples of the compositions of two different biological components within the biosensor. As noted above, the biosensor of the present invention uses two different biological components with the first and second biological components separated by a membrane (e.g., a semi-permeable membrane or a multilayer membrane). These biological components are proteins, antibodies, lipids, enzymes, reagents, polymers, aptamers, DNA or RNA molecules, microbial cells, cell receptors, a biomolecule dye. When interacting with sputum and saliva samples, the first biological component reacts chemically with the sputum and saliva and changes the chemical composition of the sputum and saliva, and the second biological component also reacts chemically with the sputum and saliva and also changes the chemical composition of the sputum and saliva.

As shown in FIG. 3, the concentration of each biological component (e.g., proteins, antibodies, lipids, enzymes, reagents, polymers, aptamers, DNA or RNA molecules, microbial cells, cell receptors, a biomolecule dye) is adjusted in such a way that when mixed with sputum and saliva samples obtained from a person, this biological component enters into a chemical reaction with the sputum and saliva and this chemical reaction is pronounced for fixation (e.g., by detectors), only if the sputum and saliva contain the presence of the SARS-CoV-2 virus strain. Therefore, the concentration of the first biological component corresponds to the limit values (thresholds) for the first SARS-CoV-2 virus strain within the sputum and saliva. Accordingly, the concentration of the second biological component corresponds to the limit values (thresholds) for the second SARS-CoV-2 virus strain within the sputum and saliva.

FIG. 4 illustrates an example of a composition of the first and second biological components, which are separated from each other by a membrane inside the biosensor. The first biological component represents proteins. The concentration of proteins in relation to their absolute specific gravity (100%) in the entire composition is 65%. This concentration of proteins means that if the Delta SARS-CoV-2 virus strain (the first SARS-CoV-2 virus strain) is present in the sputum and saliva, then the proteins, whose concentration is 65%, will enter into a chemical reaction with the sputum and saliva. This reaction will be clearly expressed and will be recorded by detectors.

The second biological component represents antibodies. The concentration of antibodies in relation to their absolute specific gravity (100%) in the entire composition is 48%. This concentration of antibodies means that if the Omicron SARS-CoV-2 virus strain (the second SARS-CoV-2 virus strain) is present in the sputum and saliva, then the antibodies, whose concentration is 48%, will enter into a chemical reaction with the sputum and saliva. This reaction will be clearly expressed and will be recorded by detectors.

Figure 5:
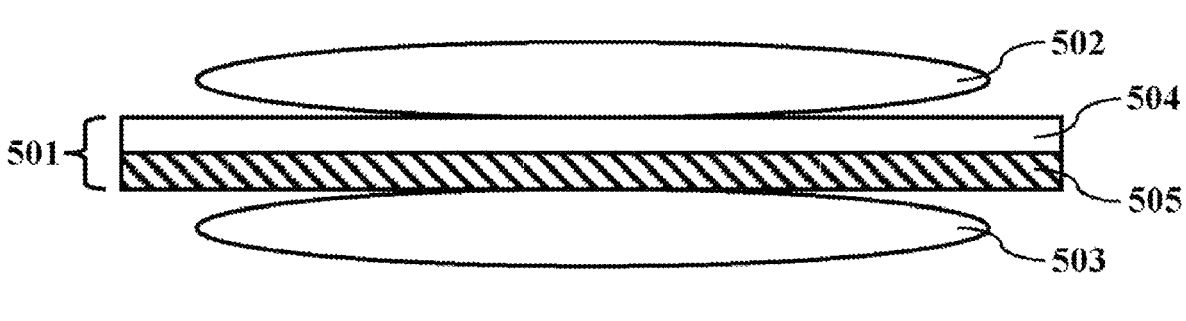
FIG. 5 illustrates an example of the cross-sectional of a membrane that separates two biological components from each other within the biosensor.

FIG. 5 illustrates an example of the cross-sectional view of a membrane that separates two biological components from each other within the biosensor of the present invention. The membrane 501 separates the first biological component 502 and the second biological component 503 within the biosensor. The membrane 501 is connected to a transducer inside the biosensor. The first biological component 502 and the second biological component 503 are connected to a transducer within the biosensor. The membrane 501 comprises one or more layers 504. The layers 504 may contain graphene, ceramic, iron, silicone, Teflon, polymer, rubber, glass, quartz. The membrane 501 also contains one or more semi-permeable layers 505. The semi-permeable layers 505 act as matrices to host the one or more layers 504.

A layer 504 may comprise graphene, ceramic, iron, silicone, Teflon, polymer, rubber, glass, quartz. In addition, the materials in the layer 504 may be an enzyme or oxidizing agent, for example. The layer 504 may be a separate layer within the membrane 501 or may be part of a semi-permeable layer 505. The one or more semi-permeable layers 505 may also be a layer 504 that is made of graphene, ceramic, iron, silicone, Teflon, polymer, rubber, glass, quartz, or contains additional material such as an enzyme or oxidizing agent.

Figure 6:
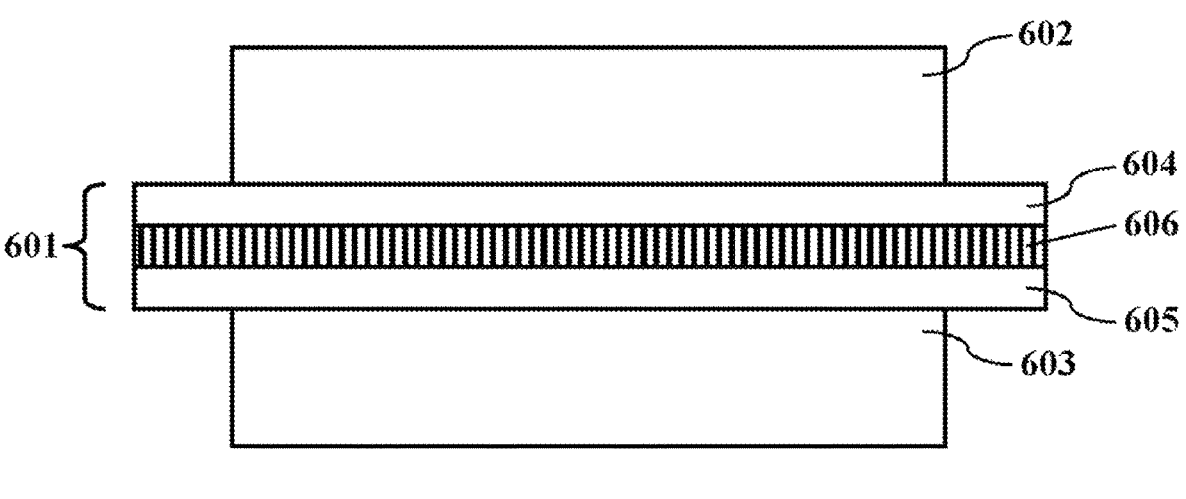
FIG. 6 illustrates another example of the cross-sectional of a membrane that separates two biological components from each other within the biosensor.

FIG. 6 illustrates another example of the cross-sectional view of a membrane that separates two biological components from each other within the biosensor of the present invention. A biosensor utilizing two different biological components separated by a multilayer membrane 601 within the biosensor comprises a surface 602 of a first biological component and a surface 603 of a second biological component. A multilayer membrane 601 contacts surfaces 602-603 and comprises layers 604 and 605. Layers 604 and 605 can be semi-permeable layers.

Between layers 604 and 605 there is an optimum buffering zone 606. The buffering zone 606 may contain graphene, ceramic, iron, silicone, Teflon, polymer, rubber, glass, quartz, enzymes, or oxidizing agents. The combination of layers 604 and 605 can be specifically chosen to provide an optimum composition for buffering zone 606, for example, to increase the buffering species within the multilayer membrane 601.

Figure 7:
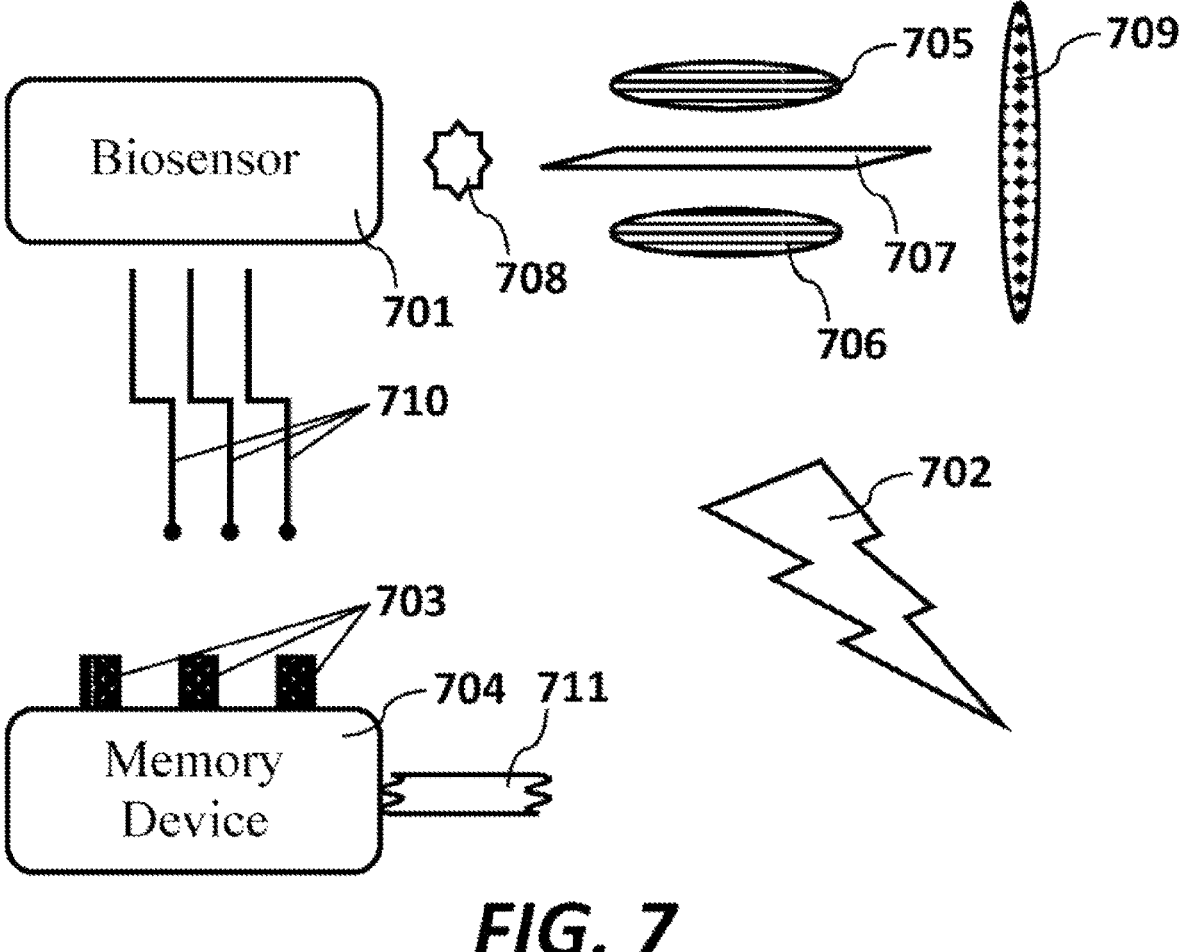
FIG. 7 is a diagram illustrating the general system for detecting COVID variants of the invention.

FIG. 7 is a diagram illustrating the general system for detecting COVID variants of the present invention. The system for determining COVID disease in a person comprises a biosensor 701 utilizing two different biological components that interacts with sputum and saliva samples obtained from a person; a wireless communication device 702 configured to communicate using a wireless peer-to-peer or machine-type-communication protocol; detectors 703 integrated into the memory device 704 that are configured to receive, decrypt and analyze data on signal from the biosensor 701 utilizing two different biological components; a memory device 704 coupled to the wireless communication device 702 and configured to determine signal thresholds for each detector 703 integrated into the memory device 704.

The biosensor 701 utilizing two different biological components is configured to include the first biological component 705 that represents proteins and the second biological component 706. The second biological component 706 within the biosensor 701 may be lipids, antibodies, enzymes, reagents, polymers, DNA or RNA molecules, microbial cells, cell receptors, a biomolecule dye, etc. The first and second biological components are separated from each other by a membrane 707 (e.g., a semi-permeable membrane, multilayer membrane, graphene membrane, ceramic membrane, iron membrane, silicone membrane, Teflon membrane, polymer membrane, rubber membrane, glass membrane, quartz membrane.) The first and second biological components are coupled to the same transducer 708 within the biosensor 701.

The first biological component 705 within the biosensor 701 interacts with the sputum and saliva samples and changes the chemical structure of the sputum and saliva samples. The second biological component 706 within the biosensor 701 interacts with the sputum and saliva samples and changes the chemical structure of the sputum and saliva samples. The sputum and saliva samples include a nasal swab, nasopharyngeal swab, throat swab, deep airway material. In some aspects, the biosensor 701 includes a microfluidic chip 709 that allows only small sputum or saliva molecules to pass through to the biosensor 701 and does not allow large molecules to pass through. In some aspects, the biosensor 701 uses graphene coatings for binding to the sputum and saliva samples.

The concentration of the first biological component 705 corresponds to the threshold for the first SARS-CoV-2 virus strain, and the concentration of the second biological component 706 corresponds to the threshold for the second SARS-CoV-2 virus strain with a mutated virus genome code. The biosensor 701 outputs a first signal when the first biological component 705 changes the chemical structure of the sputum and saliva samples, and outputs a second signal when the second biological component 706 changes the chemical structure of the sputum and saliva samples.

Thus, the biosensor 701 output a first and second signals 710 (e.g., an electrical signals, magnetic signals, optical signals) when the first biological component 705 and second biological component 706 changes the chemical structure of the sputum and saliva samples. The detectors 703 integrated into the memory device 704 then receive, decrypt and analyze the first and second signals 710 from the biosensor 701. In an aspect, the detectors 703 include electrochemical immunosensors. In another aspect, the detectors 703 include sensors based on the atomic magnetometer (AM). In yet another aspect, detectors 703 include spectrometers or fluorescence microscope.

Each detector 703 integrated into the memory device 704 is embedded in the memory device 704 and coupled to the wireless communication device 702 via the detector output. The memory device 704 coupled to the wireless communication device 702 and configured to determine signal thresholds for each detector 703 integrated into the memory device 704, identify that the person has the first or second SARS-CoV-2 virus strain in response to the detector 703 are detecting a value that is greater than or less than the signal thresholds for each detector 703, and transmit an indication that the person has contracted the SARS-CoV-2 virus strain, via the wireless communication device 702, to another device.

In some aspects, the controller 711 is additionally installed to the memory device 704 and determines, by controller command decoder, the first signal threshold and the second signal threshold for each detector 703 integrated into the memory device 704. The memory device 704 transmits the indication to the wireless communication device 702 via the detector output responsive to a determination that a value detected by the detector 703 is greater than or less than the first signal threshold and responsive to a determination that a value detected by the detector 703 is greater than or less than the second signal threshold.

In some aspects, the controller 711 updates the first signal threshold and second signal threshold for each detector 703 integrated into the memory device 704 based on the detected change in the electrical, magnetic, and/or optical characteristics of the sputum and saliva samples. In some aspects, the controller 711 updates the first signal threshold and second signal threshold for each detector 703 integrated into the memory device 704 based on the detected change in the temperature characteristic and characteristic of relative molecular motion of the sputum and saliva samples (e.g., by using molecular electronic transducers (MET) as motion sensors integrated into a memory device.)

Figure 8:
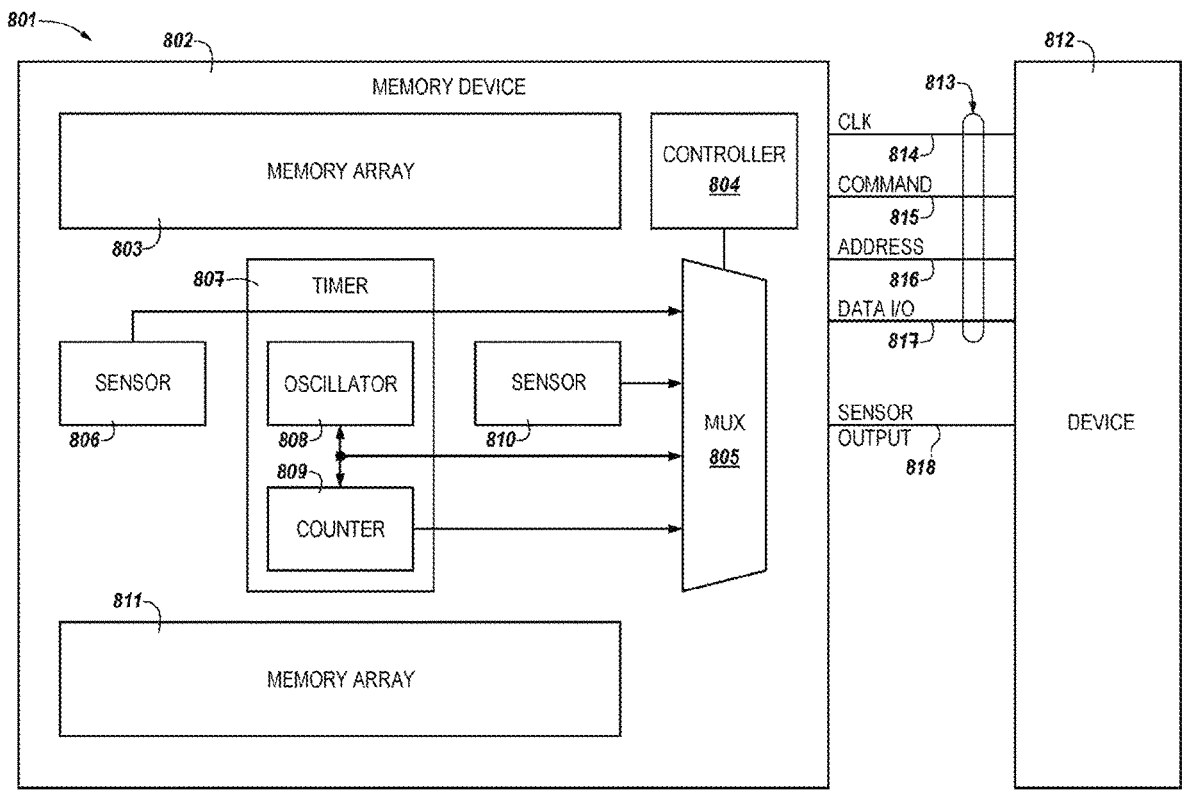
FIG. 8 is a diagram illustrating an example of the system with memory device sensors for implementing the invention.

FIG. 8 is a diagram illustrating an example of components of the system with memory device sensors for implementing the invention. FIG. 8 shows a computing system 801 that includes memory device 802. The memory device 802 can include memory array 803 and memory array 811 which may be collectively referred to herein as the memory array 803/811. The memory device 802 can include a controller 804 coupled to a multiplexer (MUX) 805. The MUX 805 can be coupled to one or more sensors embedded in circuitry of the memory device 802. For example, the MUX 805 can be coupled to an electrochemical immunosensor 806, a timer 807 (e.g., for self-refresh control), an oscillator 808, a counter 809, and a sensor based on the atomic magnetometer (AM) 810, which may be collectively referred to as the sensor or the sensors 806/810. Although specific types of sensors are mentioned herein, the present invention is not so limited and other sensors can be used (e.g., micro temperature sensor, spectrometer, fluorescence microscope, molecular electric transducer (MET), etc.)

The memory device 802 can include volatile or nonvolatile memory. For example, the memory media of the memory device 802 can be volatile memory media such as DRAM. DRAM can include a plurality of sensors which can be at least one of an electrochemical immunosensor, a sensor based on the atomic magnetometer, an oscillator, a timer, or a combination thereof. The memory device 802 can be coupled to another device 812 via a bus 813. The bus 813 can include a clock line (CLK) 814, a command line 815 to transmit commands, an address line 816 to determine where commands should be sent, and a data input/output (data I/O) 817. The other device 812 can be a central processing unit (CPU), a graphics processing unit (GPU), an application specific integrated circuit (ASIC), an edge computing device, etc. The other device 812 can be a host and/or included as part of another device such as a workstation.

A host (e.g., a processor, a CPU, a computing system, etc.) can be a host system such as a processor within a wireless communication device, a processor within a personal laptop computer, a processor within a vehicle, a processor within a desktop computer, a processor within a digital camera, a processor within a mobile telephone, a processor within an IoT enabled device, or a processor within a memory card reader, a processor within graphics processing unit (e.g., a video card), among various other types of host systems. As used herein an "IoT enabled device" can refer to devices embedded with electronics, software, sensors, actuators, and/or network connectivity which enable such devices to connect to a network and/or exchange data.

The other device 812 can include a system motherboard and/or backplane and can include a number of memory access devices, e.g., a number of processing resources (e.g., one or more processors, microprocessors, or some other type of controlling circuitry). One of ordinary skill in the art will appreciate that "a processor" can intend one or more processors, such as a parallel processing system, a number of coprocessors, etc. The other device 812 can be coupled to memory device 802 by the bus 813. The controller 804 can include a command decoder which can receive commands from the command line 815 of the bus 813. The command to read data from a sensor 806/810 can be received by the controller 804. The command can be a mode register type command from the other device 812 which can include information related to which sensor needs to output sensor data using the sensor output 818. The MUX can be a device that selects between analog and digital input signals received from selection pins and forward the signal to the sensor output 818.

As mentioned, the computing system 801 includes a sensor 806/810 embedded in circuitry the memory device 802. The sensor 806/810 can be configured to collect data related to the device 812. For example, the device 812 can be a part of and/or coupled to another device such as a workstation. The sensor 806/810 can be embedded in the memory device 802 such as including memory such as DRAM and collect data corresponding to the electrical, magnetic and optical characteristics of the sputum and saliva samples. Said differently, the embedded sensor 806/810 can be an electrochemical immunosensor 806 which can generate a sensor data value (e.g., a particular electrical signal value) in the form of a temperature of the memory device 802 coupled to another device such as a workstation. The memory device 802 can be configured to transmit the sensor 806/810 data to the device 812 using the sensor output 818. For example, the sensor output 818 coupled can be coupled to one or more of the sensors 806/810 and to the other device 812 to transmit the sensor data collected by the sensor 806/810 to the other device 802. The sensor output can be dedicated to the sensor embedded in the memory device 802. In this way, embedded sensors 806/810 can be accessible by end applications to provide sensor generated sensor data.

In some aspects, the MUX 805 can receive sensor data (electrical, magnetic and optical data of the sputum and saliva samples) from multiple sensors 806/810 responsive to receiving a command from the controller 805. For example, the controller 805 can receive a request from the other device 812 via the bus 813 to read sensor data from one or more sensors 806/810. Responsive to receiving the request, the controller 804 can transmit a command to the MUX 805 to select and forward sensor data from the electrochemical immunosensor 806 and the sensor based on the atomic magnetometer 810, where the sensor based on the atomic magnetometer 810 and the electrochemical immunosensor 806 are both embedded in circuitry of the of the memory device 802. The MUX 805 can transmit the sensor data form the electrochemical immunosensor 806 and the electrochemical immunosensor 810 to the other device 812 via the sensor output 818.

Figure 9:
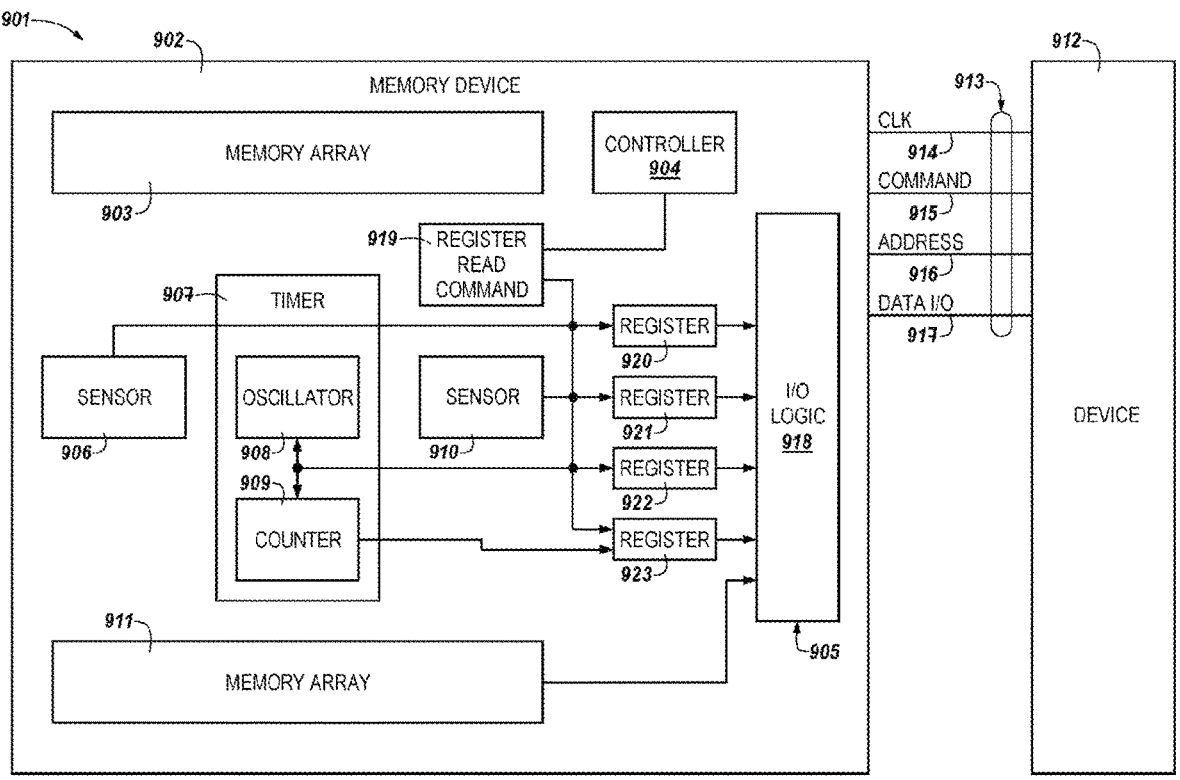
FIG. 9 is a diagram illustrating another example of the system with memory device sensors for implementing the invention.

FIG. 9 is a diagram illustrating another example of components of the system with memory device sensors for implementing the invention. A computing system 901 includes memory device sensors 906/910 and includes memory device 902 and be analogous to the memory device 802 of FIG. 8. The memory device 902 can include memory array 903 and memory array 911 which may be collectively referred to herein as the memory array 903/911 and be analogous to the memory array 803/811 of FIG. 8. The memory device 902 can include controller 904 which can be analogous to controller 804 of FIG. 8.

The controller 904 can be coupled to registers 920, 921, 922, and 923 and be collectively referred to herein as registers 920-923. The registers 920-923 can each be coupled to one or more sensors embedded in circuitry of the memory device 902. For example, the register 920 can be coupled to an electrochemical immunosensor 906, the register 921 can be coupled to a sensor based on the atomic magnetometer (AM) 910, the registers 922 and 923 can be coupled to a timer 907 via an oscillator 908 and/or a counter 909, which may be collectively referred to as the sensor or the sensors 906/910. Although specific types of sensors are mentioned herein, the present invention is not so limited and other sensors can be used (e.g., micro temperature sensor, spectrometer, fluorescence microscope, molecular electric transducer (MET), etc.) that detected a change in the electrical, magnetic and optical characteristics of the sputum and saliva samples or a change in the temperature characteristic and characteristic of relative molecular motion of the sputum and saliva samples.

The memory device 902 can be coupled to another device 912 via a bus 913. The bus 913 can include a clock line (CLK) 914, a command line 915 to transmit commands, an address line 916 to determine where commands should be sent, and a data input/output (data I/O) 917. The other device 912 can be a central processing unit (CPU), a graphics processing unit (GPU), an application specific integrated circuit (ASIC), an edge computing device, etc. The other device 912 can be included as part of another device such as a workstation. The bus 913 can be coupled to an input/output logic (I/O logic) 918. The I/O logic 918 can be a communication between the memory device 902 and the other device 912. The I/O logic 918 can include hardware to perform input and output operations 905 for the memory device 902. The I/O logic 918 can receive information (e.g., electrical, magnetic and optical data of the sputum and saliva samples) from the imbedded sensors 906/910 and transmit them to the other device 901 via the bus 913.

FIG. 9 illustrates an example of another device 912 and memory device 902 coupled to the other device 912. The memory device 902 includes a plurality of sensors 906/910 embedded in the memory device 902, and a plurality of registers 920-923 each respectively coupled to one of the plurality of sensors 906/910, the controller 904 (e.g., a command decode) to transmit commands to read one or more of the plurality of registers, and a data output (data I/O) 917 coupled to the plurality of registers 920-923 (e.g., via the I/O logic 918) to transmit the sensor data from the plurality of registers 920-923 to the other device 912. The signal (electrical, magnetic or optical signal) representing sensor data transmitted from the sensors 906/910 to respective registers 920-923 can be data of an operation of the sensor 906/910. This data can be used to detect change in the electrical, magnetic and optical characteristics of the sputum and saliva samples. For example, the electrochemical immunosensor 906 can generate an electrical signal value and transmit the electrical signal value to the register 920, the embedded timer 907 can include an oscillator 908 and/or a counter 909 which can transmit a signal representing sensor data to register 922 and/or 923, the embedded sensor based on the atomic magnetometer 910 can transmit magnetic signal value to the register 921.

The embedded timer can include the oscillator 908 which can produce a periodic signal to transmit to the register 922 and/or to the counter 909. The counter 909 can (independently or concurrently with the oscillator 908) transmit a quantity of incidences of sensor data collected by one or more of the sensors 906/910. Said differently, the oscillator 908 can work with the counter 909 to periodically generate a signal which can report a quantity of sensor data signals generated from any of the sensors 906/910. In contrast, the oscillator 908 and the counter 909 can operate independently to transmit respective sensor data to respective registers. In some aspects, the controller 902 can configure the sensors 906/910 to generate sensor data based on the detected change in the electrical, magnetic and optical characteristics of the sputum and saliva samples. For example, the controller 904 can configure the sensors 906/910 to generate sensor data to the respective registers 920-923 when the other device 912 is located in the sputum and saliva samples. The controller 904 can generate a register read command 919 to read the sensor data stored in the respective registers and the I/O logic 918 can transmit a signal representing sensor data from the registers 920-923 to the other device 912.

The controller 904 can receive an indication from the other device 912 located in the sputum and saliva samples, and the controller 904 can configure the sensors 906/910 to generate sensor data about the change in the electrical, magnetic and optical characteristics of the sputum and saliva samples or the change in the temperature characteristic and characteristic of relative molecular motion of the sputum and saliva samples. For example, the controller 904 can receive an indication that the other device 912 is located in the sputum and saliva samples. The controller 904 can configure the electrochemical immunosensor 906 to generate an electrical signal value (e.g., an encoded 8-bit binary string) and transmit the electrical signal value to the register 920. Responsive to a register read command 919 transmitted from the controller 904, the I/O logic 918 can transmit the sensor data from the register 920 including the electrical signal value to the other device 912. Said differently, the I/O logic 918 can transmit the values related to the respective operations of the plurality of sensors 906/910 to the other device 912. Using these methods, the electrical signal value generated by the embedded electrochemical immunosensor 906 can be accessible to the other device 912 and/or user.

In some aspects, the embedded timer 907 (using an embedded oscillator 908 and/or an embedded counter 909) can produce a timer output with a fixed period, for example, the controller 904 may be configured to generate a register read command 919 when a quantity of seconds have elapsed. The controller 904 can program the memory device 902 to generate sensor outputs to the respective registers 920-923 based on the quantity of seconds that have elapsed. As mentioned, the sensor based on the atomic magnetometer 910 can be embedded in the circuitry of the memory device 902 and can detect a change in magnetic signal within the sputum and saliva samples.

The controller 904 can receive an indication from the other device 912 related to the detected change in the electrical, magnetic and optical characteristics of the sputum and saliva samples, and the controller 904 can configure the sensors 906/910 to generate sensor data about the detected change in the electrical, magnetic and optical characteristics of the sputum and saliva samples. For example, the controller 904 can receive an indication that the other device 912 is located in the sputum and saliva samples. The controller 904 can configure the sensor based on the atomic magnetometer 910 to generate a particular magnetic signal value is detected in the environment. Responsive to a register read command 919 transmitted from the controller 904, the I/O logic 918 can transmit the sensor data from the register 921 including the particular magnetic signal value to the other device 912.

Similarly, the controller 904 can receive an indication from the other device 912 related to the detected change in the change in the temperature characteristic and characteristic of relative molecular motion of the sputum and saliva samples (e.g., by using molecular electronic transducers (MET) as motion sensors embedded into a memory device.) The controller 904 can then configure the sensors 906/910 to generate sensor data about the detected change in the temperature characteristic and characteristic of relative molecular motion of the sputum and saliva samples.

In some aspects, multiple embedded sensors 906/910 can be used in combination to provide information to the user via the other device 912. For example, the other device 912 can be coupled to a wireless communication device which can initiate an operation responsive to transmission of the signal representing sensor data (e.g., from one or more of the sensors 906/910) from the plurality of registers 920-923 to the other device 912. The wireless communication device can include the other device 912 and can make decisions based on the received sensor data. For example, the wireless communication device may be a smartphone, and the other device 912 coupled to the smartphone may receive an electrical signal value from the electrochemical immunosensor 906, and the sensor based on the atomic magnetometer 910 embedded in the memory device 902 of the smartphone. Based on the receipt of the electrical signal value and the magnetic signal value, the other device 912 may initiate the smartphone to change an operation. Using these methods, users can gain access to embedded sensor data and avoid the need for external sensor installations.

Figure 10:
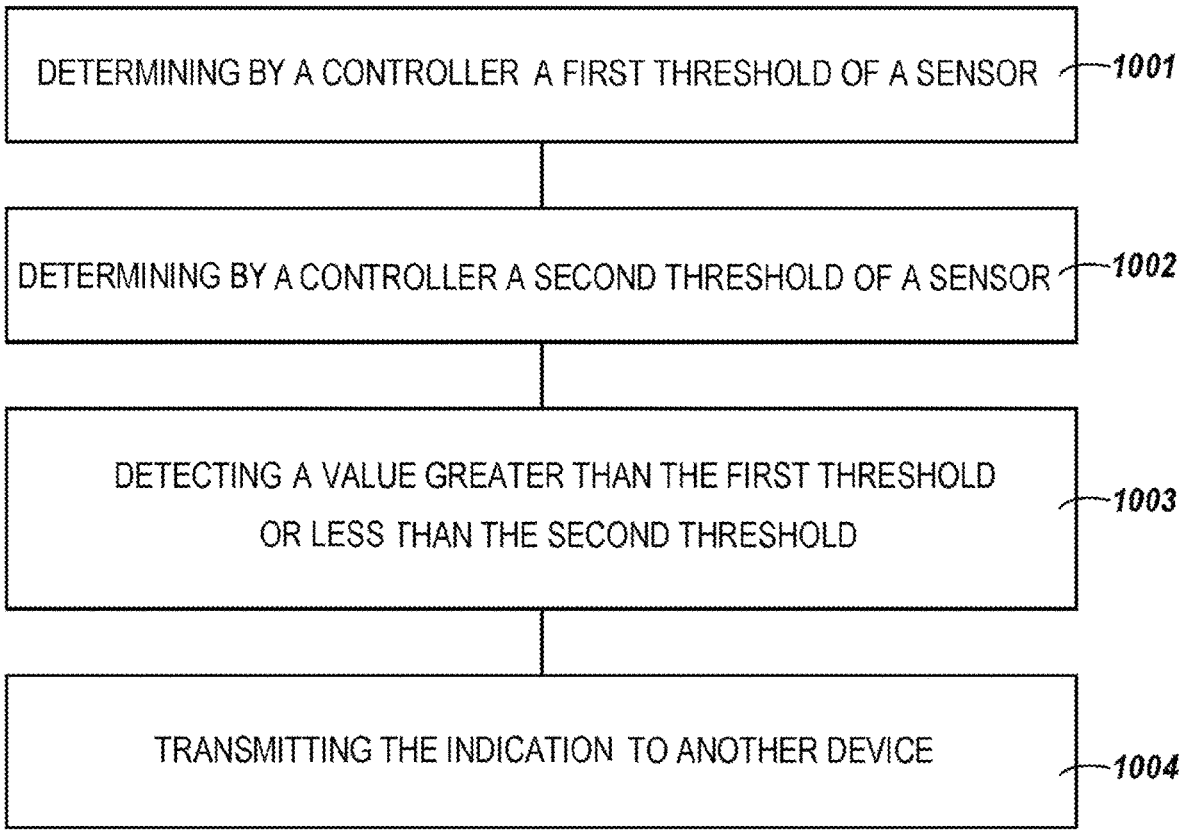
FIG. 10 is a flowchart illustrating the steps of using memory device sensors according to a first embodiment of the invention.

FIG. 10 is a flowchart illustrating the steps of using memory device sensors according to a first embodiment of the invention. In step 1001, a first threshold of a sensor (e.g., sensors 806/810 of FIG. 8) embedded in the memory device is determined by the controller (e.g., the controller 804 of FIG. 8) coupled to a memory device (e.g., a memory device 802 of FIG. 8) using the controller command decoder. The sensors can be embedded in the memory device and enabled to generate values (e.g., electrical signal values, magnetic signal values, optical signal values) which can be provided to another device and be accessible to users, or end applications. The sensor can be an electrochemical immunosensor embedded in the memory device and the first threshold can be a high electrical signal threshold. The controller can configure the electrochemical immunosensor to include a high electrical signal threshold and/or a low electrical signal threshold.

In step 1002, a second threshold of the sensor embedded in the memory device is determined by the controller using the controller command decoder. In this example, the second threshold can be a low electrical signal threshold. The controller can, via the memory device, transmit an indication to the other device responsive to the electrochemical immunosensor detecting an electrical signal that is greater than or less than the first threshold and the second threshold. In step 1003, the memory device transmits an indication responsive to the sensor detecting a value greater than the first threshold or less than the second threshold. In an aspect, the second threshold can be a low electrical signal threshold. To provide the other device and/or the workstation with the indication and/or the sensor data values from the embedded sensors, the memory device can transmit the indication (or sensor data values) via a sensor output dedicated to the embedded sensors of the memory device.

In step 1004, the indication is transmitted via a sensor output to another device. The other device may be a part of a workstation or a computing device that includes hardware and/or software to control the operations of the workstation. The other device can be directly or indirectly coupled to the sensors embedded in the memory device via the sensor output (e.g., the sensor output 818 of FIG. 8). In some aspects, the memory device can alter the first and the second threshold of the embedded sensor based on the detected change in the electrical, magnetic, and optical characteristics of the sputum and saliva samples. In some aspects, the memory device can alter the first and the second threshold of the embedded sensor based on the detected change in the temperature characteristic and characteristic of relative molecular motion of the sputum and saliva samples.

For example, the system further is detected by the controller a change in the electrical, magnetic and optical characteristics of the sputum and saliva samples, altering, by the controller, the first threshold of the sensor embedded in the memory device; and altering, by the controller, the second threshold of the sensor embedded in the memory device, where the first threshold and the second threshold are altered based at least in part on the detected change in the characteristics of the sputum and saliva samples. The alteration of the sensor threshold can include disabling one or more sensors embedded in the memory device. While the examples of FIG. 10 describe the utilization of a sensor output, the present invention is not so limited. The examples, described in connection with FIG. 10 can utilize registers (e.g., registers 920-923 of FIG. 9) and an I/O logic (e.g., an I/O logic 918 of FIG. 9).

Figure 11:
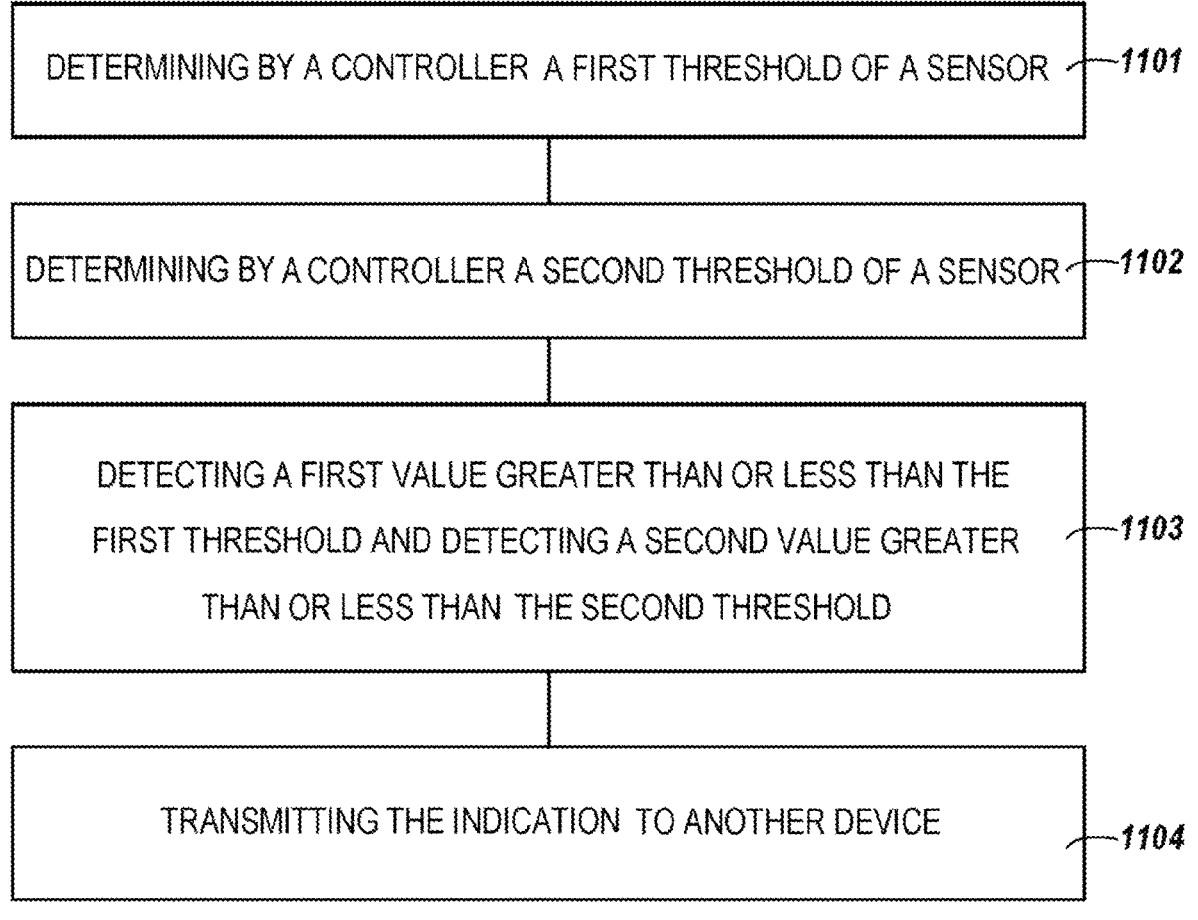
FIG. 11 is a flowchart illustrating the steps of using memory device sensors according to a second embodiment of the invention.

FIG. 11 is a flowchart illustrating the steps of using memory device sensors according to a second embodiment of the invention. In step 1101, a first threshold of a first sensor embedded in a memory device is determined by a controller using the controller command decoder. The sensors can be embedded in the memory device and enabled to generate values (e.g., electrical signal values, magnetic signal values, optical signal values s) which can be provided to another device and be accessible to users, or end applications. In step 1102, a second threshold of a second sensor (e.g., a sensor 906/910 of FIG. 9) embedded in the memory device is determined by the controller using the controller command decoder. The memory device and/or the controller included in the memory device can be configured to transmit an indication about the values (or the values themselves) generated by the sensors embedded in the memory device to the other device.

In step 1103, the memory device transmits an indication responsive to the first sensor detecting a first value greater than or less than the first threshold and responsive to the second sensor detecting a second value greater than or less than the second threshold. The indication can be transmitted via a sensor output. Using this method, the sensors embedded in the memory device can transmit the sensor data values generated to the other device coupled to the workstation, and/or an indication about the values detected by the embedded sensors can be transmitted to the other device coupled to the a workstation and/or another device.

For example, in step 1104, the indication is transmitted to another device, via a sensor output coupling the first sensor and the second sensor to the other device, wherein the indication is based on the first value and the second value. The indication can be an alert indicating that a value collected by the sensors embedded in the memory device is greater than or less than the respective configured thresholds. While the examples of FIG. 11 describe the utilization of a sensor output, the present invention is not so limited. The examples, described in connection with FIG. 11 can utilize registers (e.g., registers 920-923 of FIG. 9) and an I/O logic (e.g., an I/O logic 918 of FIG. 9). While example of a workstation is used herein, other examples are contemplated.

Figure 12:
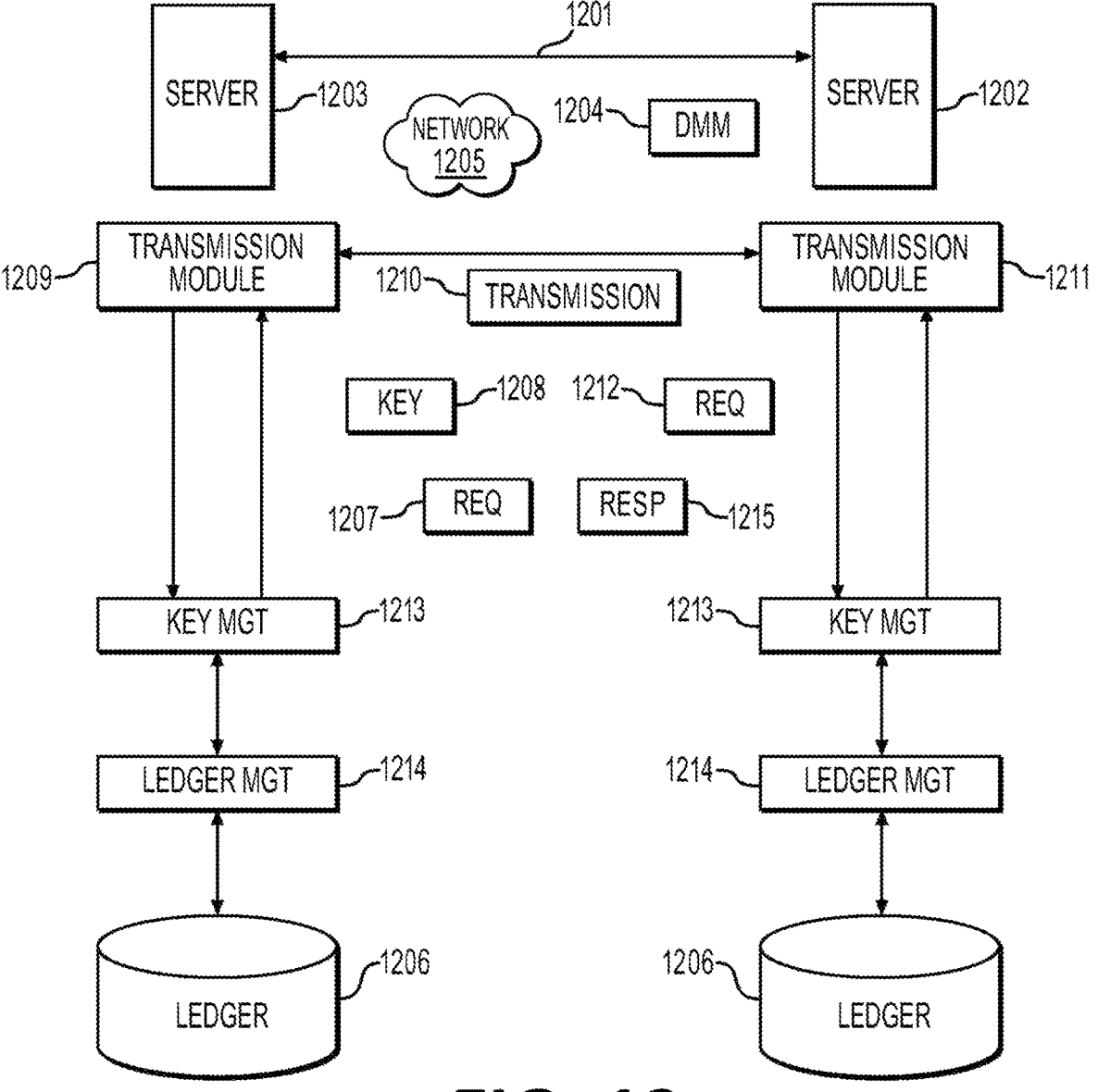
FIG. 12 is a diagram illustrating components of the data transmission operation.

FIG. 12 is a diagram illustrating components for implementing the data transmission operation for implementing the invention. The components provide the data transmission operation between the sensor or biosensor and server. The data transmission operation 1201 in an embodiment of the present invention is carried out by using end-to-end encryption of the data by creating a key. This seems appropriate because some of the data transferred (e.g., data on the person's current illnesses or person's symptom data values) are personal data received and secure methods of data transfer between servers will provide protection against possible hacking and loss of person's personal data.

In operation, the servers 1202 and 1203 enable secure transmission of data between or on behalf of their hardware and software components through the use of data merging module (DMM) 1204 connected by network 1205. The servers 1202 and 1203 cooperate with the DMM 1204 to generate and maintain a distributed ledger 1206. The distributed ledger 1206 stores metadata associated with hardware and software components of servers 1202 and 1203. The distributed ledger 1206 implements a data structure that includes various blocks, with each block holding a batch of individual transmissions and including a timestamp indicating block inclusion in the ledger 1206.

Each server 1202 and 1203 may include a ledger management module, and a key management module. The ledger management modules manage the distributed ledger 1206. For example, the ledger management modules may propose new blocks for the distributed ledger 1206 (each proposed block containing one or more transmissions.) The ledger management module further performs operations to ensure that the network node includes an updated copy of the distributed ledger 1206. Generally, the ledger management module serves as an interface for the distributed ledger 1206. For example, the key management module may access the distributed ledger 1206 by way of the key management module. In operation, a transmission module of server 1203 may initiate a transmission with the server 1202. To execute this transmission, the transmission module of server 1203 first may query the distributed ledger 1206 to determine if a certification transmission is stored therein that would satisfy access requirements.

The distributed ledger 1206 may contain the certification transmission but not the required key. Alternatively, the distributed ledger 1206 may contain both the key and the certification transmission. Assuming only the key is not available, the server 1203 may request the server 1202 provide the required key. In response, the transmission module transmits a key request 1207 to the key management module. The key request 1207 indicates a requested transmission type, e.g., health certification (i.e., the key request 1207 is for a health credential that the transmission module requires to complete the transmission.)

The key management module provides a key 1208 in response to receiving the key request 1207. The key management module determines whether the key request 1207 is a valid request. The key management module accesses the distributed ledger 1206 to determine whether the key request 1207 satisfies one or more validation criterion. For example, the key management module may query the distributed ledger 1206 to determine whether the requested time duration, the requested number of transmissions, and/or requested transmission type are permitted.

The key management module synthesizes the key 1208. The key 1208 may include a session key, a pair of keys (e.g., a public key and a private key.) In some examples, the pair of keys is asymmetric or a single shared key. For example, the key management module may employ a variety of symmetric-key algorithms, such as Data Encryption Standard (DES) and Advanced Encryption Standard (AES), to generate the key 1208. Alternatively, the key management module employs a variety of public-key algorithms, such as RSA, to generate the key 1208. In an aspect, the key 1208 includes a random number. In another aspect, the key 1208 is the output of a hash function, where the hash function is a hash of the names of the entities, a time of day, and/or a random number. In yet another aspect, the key 1208 includes a credential.

The key 1208 is associated with a key identifier (ID) that identifies the key, and a validity period that indicates a time duration during which the key 1208 is valid. The validity period may be equal to requested time duration. However, if the requested time duration is greater than a threshold time duration, the validity period may be limited to the threshold time duration. In an aspect, the key 1208 may be associated with a validity number that indicates the number of transmissions that can be completed with the key 1208. The validity number may be equal to a requested number of transmissions. However, if the requested number of transmissions is greater than a threshold number of transmissions, the validity number may be limited to the threshold number of transmissions. In another aspect, the key 1208 is associated with a validity type that indicates a transmission type that may be completed with the key request 1207. The validity type may be the same as a requested transmission type.

The transmission module 1209 may employ the key 1208 to synthesize the transmission data 1210. In an aspect, the transmission module 1209 signs the transmission data 1210 (e.g., a hash of the transmission data) with the key 1208. In another aspect, the transmission data 1210 includes encrypted data. The transmission module 1209 employs the key 1208 to encrypt the transmission data 1210. When encrypted, the transmission module 1209 transmits the transmission data 1210. The transmission module 1211 receives the transmission data 1210 and completes the transmission based on the transmission data 1210.

The transmission module 1211 may determine whether the transmission data 1210 is valid by, for example, determining whether the key 1208 employed to synthesize the transmission data 1210 is valid. As such, the transmission module 1211 transmits a validation request 1212 to the key management module 1213. In an aspect, the validation request 1212 includes the key 1208 (e.g., when the transmission data 1210 includes the key 1208). In another aspect, the validation request 1212 includes the key ID. In yet another aspect, the validation request 1212 includes only the transmission data 1210.

The key management module 1213 receives the validation request 1212 and determines whether the key 1208 employed to synthesize the transmission data 1210 is valid by, for example, querying the distributed ledger 1206 with the key 1208 and/or the key ID. The second key management module 1214 then transmits a validation response 1215 to the transmission module 1211. The validation response 1215 indicates a validity status of the key 1208. For example, the validation response 1215 may indicate the validity period, the validity number, and/or the validity type associated with the key 1208 are satisfied.

Based on the validation response 1215, transmission module 1211 employs the transmission data 1210 to complete the transmission. For example, the transmission module 1211 may complete the transmission if the validation response 1215 indicates that the transmission data 1210 was synthesized with a valid key (e.g., the key 1208 is valid.) In another aspect, the transmission module 1211 may access the distributed ledger 1206 to determine whether the transmission is permitted. If the distributed ledger 1206 indicates that the transmission is permitted, the second transmission module 1211 completes the transmission.

Figure 13:
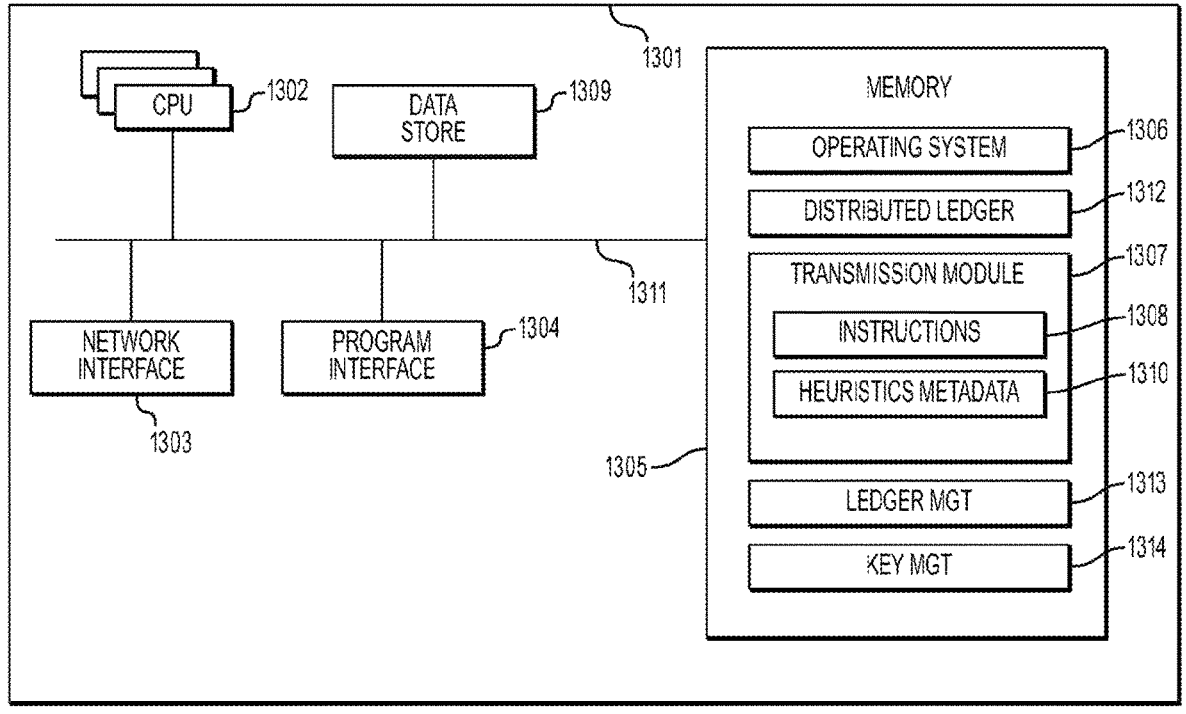
FIG. 13 illustrates components of the data merging module of FIG. 12.

FIG. 13 illustrates components of the data merging module of FIG. 12, which is used to transmitting data between the sensor or biosensor and server. The data merging module (DMM) includes server sub-system 1301. Server sub-system 1301 in turn includes one or more CPUs 1302, network interface 1303, program interface 1304, and memory 1305. Memory 1305 is a non-transitory computer-readable memory. Memory 1305 includes server operating system (OS) 1306 and transmission module 1307. Transmission module 1307 includes machine instructions 1308, which may be loaded from non-transitory computer-readable storage medium (i.e., data store) 1309, and heuristics and metadata 1310. The CPUs 1302, network interface 1303, program interface 1304, memory 1305, and data store 1309 communicate over system bus 1311. The operating system 1306 includes procedures for handling various basic system services and for performing hardware-dependent tasks.

The transmission module 1307 manages transmissions between the sensor or biosensor and server. For example, the transmission module 1307 may transmit a key request to a network node within a cluster of network nodes that are configured to maintain a distributed ledger. The transmission module 1307 receives a key in response to transmitting the key request and synthesizes transmission data with the key. The transmission module 1307 transmits the transmission data to another entity. The transmission module 1307 receives transmission data, transmits a validation request to determine whether the key utilized to synthesize the transmission data is valid, receives a validation response, and utilizes the transmission data to complete a transmission if the validation response indicates that the key is valid. To that end, the transmission module 1307 includes machine instructions 1308, and heuristics and metadata 1310.

The memory 1305 and/or the data store 1309 also stores programs, modules, and data structures to enable a distributed ledger 1312, a ledger management module 1313, and a key management module 1314. The distributed ledger 1312 may be distributed over various network nodes. In some aspects, each network node stores a local copy of the distributed ledger 1312. The distributed ledger 1312 may store information regarding transmissions between the sensor or biosensor and server. In some aspects, the distributed ledger 1312 stores a batch of transmissions in a block. In some aspects, each block is timestamped.

The ledger management module 1313 manages the distributed ledger 1312. For example, the ledger management module 1313 functions to ensure that the local copy of the distributed ledger 1312 is synchronized with the local copy of the distributed ledger 1312 at other network nodes. The ledger management module 1313 participates in consensus protocols associated with the distributed ledger 1312. For example, the ledger management module 1313 may propose new blocks for the distributed ledger 1312 and/or votes on block proposals received from other network nodes. To that end, the ledger management module 1313 includes machine instructions, and heuristics, and metadata.

The key management module 1314 receives a key request from an entity, determines whether the key request is valid, synthesizes a key if the key request is valid, transmits the key to the entity, and stores the key in the distributed ledger 1312. The key management module 1314 determines whether the key request is valid by determining whether one or more validation criterion stored in the distributed ledger 1312 is satisfied. For example, the key management module 1314 receives a validation request from an entity, accesses the distributed ledger 1312 to determine whether the key utilized to synthesize the transmission data is valid, and transmits a validation response that indicates the validity status of the key to the entity. To that end, the key management module 1314 includes machine instructions, heuristics, and metadata.

FIG. 14 illustrates an example of a metric of differentials that includes the values of the differentials for major SARS-CoV-2 virus strains. The left-hand column of the metric contains the results of laboratory medical tests that include tests for COVID disease (e.g., antigen test, molecular test, antibody test), and laboratory medical examinations required to obtain the values of the person's biochemical and biophysical data in relation to the symptoms of the major SARS-CoV-2 virus strains. Symptoms of the SARS-CoV-2 virus strains are variable, but in general include fever, cough, headache, fatigue, breathing difficulties, and loss of smell and taste. The severity of mutated SARS-CoV-2 virus strains varies and symptoms of the mutated SARS-CoV-2 virus strains are variable. Common symptoms include headache, loss of smell and taste, nasal congestion and a runny nose, a cough, muscle pain, a sore throat, a fever, diarrhea, and breathing difficulties. People with the same infection may have different symptoms, and their symptoms may change over time.

Laboratory medical tests listed in the left-hand column of the metric include reverse transcription polymerase chain reaction (RT-PCR) test, nucleic acid test, serological test, molecular test CRISPR, isothermal nucleic acid amplification (INAA), digital polymerase chain reaction (DPCR), microarray analysis, next-generation sequencing (NGS), antigen tests for antigen proteins, rapid diagnostic test (RDT), enzyme-linked immunosorbent assay test (ELISA), neutralization assay, chemiluminescent immunoassay (CI). Samples for these tests can be nasal swab, nasopharyngeal swab, throat swab, deep airway material, saliva, etc. Laboratory medical examinations include chest CT scans, checking for an elevated body temperature, and checking for low blood oxygen levels.

The left-hand column of the metric further contains names of symptoms and diseases, for which the person's biochemical and biophysical data is gathered by a plurality of sensors (including biosensors) for detecting respiratory symptoms (cough, sputum, shortness of breath, fever, anosmia (loss of smell), ageusia (loss of taste), nasal congestion, runny nose, sore throat), musculoskeletal symptoms (muscle pain, joint pain, headache, fatigue), digestive symptoms (abdominal pain, vomiting, diarrhea), physiological diseases (diabetes, lung diseases, cardiovascular diseases, ischemia, hypertension.)

It should be obvious to those skilled in the art which sensors can be used for each individual symptom, and therefore, it is pointless to list all these sensors in the present invention, especially when new and enhanced sensors are continuously being introduced in medical practice (e.g., biosensors which convert a biological response into an electrical signal and combine a biological component with a physicochemical detector.) It is also obvious that as many available sensors should be used and as many laboratory medical tests, laboratory medical examinations should be run as possible to obtain maximum data. Sensors for other symptoms not mentioned above can also be used, if necessary, such as saliva sensors (e.g., ultrasound of the salivary glands), etc.

The header of the metric contains the names of the major SARS-CoV-2 virus strains: original SARS-CoV-2 virus strain, Alpha (lineage B.1.1.7), B.1.1.7 (E484K), Beta (lineage B.1.351), Gamma (lineage P.1), Delta (lineage B.1.617.2), Lambda (lineage C.37), Mu (lineage B.1.621), Epsilon (lineages B.1.429, B.1.427, CAL.20C), Zeta (lineage P.2), Theta (lineage P.3), Eta (lineage B.1.525), Iota (lineage B.1.526), Kappa (lineage B.1.617.1), Lineage B.1.1.207, Lineage B.1.1.317, Lineage B.1.616, Lineage B.1.618, Omicron (lineage B.1.1.529). This list is not complete and can be further expanded by adding new COVID variants discovered later.

Based on the scientific medical literature, medical guidelines provide predetermined symptom threshold values that can be used to identify major SARS-CoV-2 virus strains (e.g., those listed in the header of the table.) Therefore, it is possible to calculate the actual differentials (differences) between the values of the person's biochemical and biophysical data obtained from a plurality of sensors, through laboratory medical tests, laboratory medical examinations (listed in the left-hand column of the metric), and the predetermined symptom threshold values that would help to identify the major SARS-CoV-2 virus strains. These differentials are added to the metric, so the metric contains the values of the differentials that represent differences between the values of the person's biochemical and biophysical data and predetermined symptom threshold values for the major SARS-CoV-2 virus strains.

The differentials mentioned in the present invention may be negative. For example, a healthy person's temperature is about 36.6° C., while the temperature indicative of the Delta SARS-CoV-2 virus strain is 40° C. According to conventional medical practice, if the person's temperature is 38° C., for instance, then the differential is not calculated, as the 40° C. threshold value hasn't been reached. Further diagnosis of the Delta SARS-CoV-2 virus strain is not carried out. According to the present, differentials are always calculated, and the diagnosis is carried out, even if the difference is negative (−2° C.). It is possible that differentials of other symptoms all point to the fact the person has Delta SARS-CoV-2 virus strain, while the insufficiently high temperature is due to the person's individual physiological parameters. Therefore, the data in the metric of FIG. 14 includes differentials, both positive and negative, between the values of the person's biochemical and biophysical data and predetermined symptom threshold values for the major SARS-CoV-2 virus strains.

For each of a plurality of the values of differentials within the metric of the differentials of FIG. 14, which are calculated by comparing the values of data received from a person to predetermined symptom threshold values for the SARS-CoV-2 virus strains (e.g., for the first original SARS-CoV-2 virus strain and for the second mutated SARS-CoV-2 virus strain), the medical analytics platform of the present invention can identify an accurate value indicative of the likelihood that the person is experiencing the symptom of the SARS-CoV-2 virus strain (e.g., the symptom of the first original SARS-CoV-2 virus strain or the symptom of the second mutated SARS-CoV-2 virus strain) and the severity this symptom. Thereafter, it is created a metric of all differentials in which the differentials (e.g., the first and second differentials) are ordered in their values (accurate value) relative to symptoms of the SARS-CoV-2 virus strains (e.g., the symptom of the first original SARS-CoV-2 virus strain or the symptom of the second mutated SARS-CoV-2 virus strain.)

FIG. 15 illustrates examples of the metrics of differentials that includes the accurate values and complex symptoms. The accurate value indicates of the likelihood that the person is experiencing the symptom and the severity this symptom. By relying on well established, medically documented, facts and characteristics for symptoms of the SARS-CoV-2 virus strains (and discretizing measures that calibrate them), and, e.g., machine learning techniques, the accurate value (accurate values № 1-5 in 15a) can be computed for each of a plurality of the differentials (values of differential № 1-5 in 15a). Thus, accurate values for differentials that indicate the likelihood and severity (e.g., uninfected, mild, moderate, and severe) of symptom of the SARS-CoV-2 virus strain can be established.)

In an aspect, machine learning techniques are used to determine accurate values for differentials that indicate the likelihood and severity of symptoms of the SARS-CoV-2 virus strains. The medical analytics platform may use a (deep or shallow) machine learning process to definite accurate values for the differentials. As additional studies are released, it is possible to update the accurate values for the differentials describing the likelihood and severity of each of the symptoms above. In another aspect, the accurate values for the differentials can be the original values of the differentials obtained by comparing the values of data received from a person representing their symptoms to predetermined symptom threshold values for the SARS-CoV-2 virus strain. In this case, the accurate values for the differentials and values of the differentials are the same.

Thus, the metrics of the differentials stores a plurality of records of values (or accurate values) of differentials, each associating a symptom with possible symptoms of the SARS-CoV-2 virus strains. It is also possible to determine complex symptoms within the plurality of the symptoms of the SARS-CoV-2 virus strains. The complex symptom is the symptom that shows the correlation of the several symptoms of the SARS-CoV-2 virus strains. For example, as shown in 15b, if symptoms comprise shortness of breath, sweating, chills, fatigue, headache, muscle pain, the possible complex symptom comprises fever that may cause the above symptoms, and the differentials lists a plurality of values of differentials (accurate values) calculated for these symptoms.

The metric of 15b also can include functions to determine a possible cause or causes of a symptom. Such functions may be in forms of an expert system or a decision tree. Examples of web-based expert system include the software owned and managed by EasyDiagnosis, a division of MatheMEDics such as www.easydiagnosis.com. It is noted that 15b is merely illustrative of a logical record. Many representations to store, retrieve, search for, or modify all or parts of the illustrated stored content are well known in the state of the art.

The metric of the differentials includes complex symptoms indicated or associated with the Delta SARS-CoV-2 virus strain. As shown in 15b, symptoms associated with the Delta SARS-CoV-2 virus strain may include shortness of breath, especially with activity, or when lying down, swelling of feet and ankles, fatigue and weakness, persistent cough or wheezing cough that may be accompanied by white or blood-tinged phlegm, rapid weight gain, irregular or rapid heartbeat, change in urine production (increase or decrease, need to urinate at night), nausea, loss of appetite, decreased alertness, and increase of respiration rate.

Fatigue and shortness of breath can be distinguished as complex symptoms that show the correlation of the noted above symptoms of the Delta SARS-CoV-2 virus strain for the indicated example. Each of these complex symptoms may be evaluated based on a well-known scale. For example, the fatigue and shortness of breath may be characterized to show the severity on a New York Heart Association scale of 0-10 (10 being very severe fatigue or shortness of breath.) Using complex symptoms within the metrics of the differentials, it may find that the person has contracted the Delta SARS-CoV-2 virus strain, if for example, feels fatigue very easily, and experiences shortness of breath.

The comprehensiveness of the information about the values (or accurate values) of the differentials and the complex symptoms within the metrics of the differentials allows to evaluate the health situation of the person and make a conclusion about a presence or absence of SARS-CoV-2 disease in a person. The record of complex symptom in 15*b* may include a summary of the complex symptom, possible causes of the symptom and the correlation of the several symptoms. As will be appreciated, this data can be also grouped and weighted.

FIG. 16 illustrates examples of the metrics of differentials that include the weighting coefficients. The severity of symptom of COVID disease is described by the weighting coefficient. The weighting coefficient characterizes the severity level of symptom. The weighting coefficients for symptoms of the SARS-CoV-2 virus strains may be determined, based on the latest medical documentation, indicative of higher/lower likelihoods that the person is experiencing more/less severe symptoms of the SARS-CoV-2 virus strains. The weighting coefficients for symptoms of the SARS-CoV-2 virus strains may be compared with each other. For each value (or accurate value) of differential within the metric of differentials, a higher weighting coefficient is indicative of a more severe the respective symptom of the SARS-CoV-2 virus strain. Thereafter, the values (or accurate values) of the differentials within the metric of the differentials are then ordered relative to the weighting coefficients for symptoms.

The weighting coefficient of the symptom is established by weighing the severity level of this symptom. The each symptom may be weighted based on the prevalence and correlation between each symptom and the SARS-CoV-2 virus strains, as identified in the latest medical documentation, such that a weighting coefficient of symptom below the lowest thresholds is indicative of a low likelihood that the person has contracted the SARS-CoV-2 virus strain. And vice versa, a weighting coefficient of symptom above the highest thresholds is indicative of a high likelihood that the person has contracted the SARS-CoV-2 virus strain.

16*a* illustrates an example of weighting coefficients for ten symptoms of the most common SARS-CoV-2 virus strains: fever, chills, cough, difficulty breathing, nasal congestion, loss of taste, sore throat, loss of smell, headache, muscle aches. As noted above, the SARS-CoV-2 symptoms within the metric of the differentials may be weighted differently when evaluating possible diseases of the SARS-CoV-2 virus strains. Thus, the weighting coefficient is determined for each above symptom that characterizes the severity level of symptom.

Thereafter the values (or accurate values) of the differentials within the metric are ordered relative to these weighting coefficients. The hierarchy of weighting symptoms of the SARS-CoV-2 virus strains in 16*a* is based on the utilizing a scoring/weighting range of 1-6. A score of 1 indicates the highest confidence level for a SARS-CoV-2 symptom with a score of 6 having the least reliable value for validating or verifying the symptom. It is possible to generate a weighting coefficients № 1, № 2, № 3, № 4, № 5, based on the values (or accurate values) of the differentials and the weight of symptom it has been assigned.

16*b* illustrates exemplary rules for weighting the SARS-CoV-2 symptoms that can be used, for example, in conjunction with the weighting coefficients identified in the metric of 16*a* to determine a confidence level that a SARS-CoV-2 disease is present. In order for a symptom of the SARS-CoV-2 virus strain to be deemed to have a high severity, certain combinations of weighting coefficients must exist. If the weight level based on the weighting coefficients exceeds a predetermined weight level, the condition is considered "confirmed" that the person has been diagnosed with that SARS-CoV-2 symptom.

The weight level may be determined using the weighted method using machine learning techniques or based on the presence of a certain number of weighting coefficients. For example, a symptom of the SARS-CoV-2 virus strain could be confirmed if any three of the weighting coefficients are found into the metric of the differentials. As shown in 16*b*, for the Delta SARS-CoV-2 virus strain, if three (or more) weighted coefficients for the Delta strain at the same time are present, the weight level is considered to be surpassed and the symptom of the Delta SARS-CoV-2 virus strain is considered to be validated or confirmed.

After performing the above steps to determine symptoms accurate values for differentials, weighting coefficients for symptoms of the SARS-CoV-2 virus strains and complex symptoms of the SARS-CoV-2 virus strains, the metric of differentials is created. The values (or accurate values) of the differentials within the metric are ordered in their values relative to symptoms of the SARS-CoV-2 virus strains (e.g., to symptoms of the first SARS-CoV-2 virus strain and symptoms of the second SARS-CoV-2 virus strain.)

The metrics of the differentials are then compared to the predetermined metric that contains known values of differentials indicating that the person has contracted SARS-CoV-2 virus strains (e.g., the first original SARS-CoV-2 virus strain or the second mutated SARS-CoV-2 virus strain.) In response to this comparison, a presence or absence of SARS-CoV-2 in a person is determined. In an aspect, the determination occurs when at least one value (accurate value) within the metric of the differentials exceeds the values within the predetermined known metric. In another aspect, the determination occurs when the majority of the values (accurate values) within the metric of the differentials exceed the values within the predetermined known metric.

Other embodiments of the present invention are possible. In an aspect, the values (or accurate values) of the differentials within the metric of differentials can be combined into multiple groups based on the differences in the values (or accurate values) of the differentials, and after that the groups of the differentials within the metric of the differentials are ordered relative to symptoms of the SARS-CoV-2 virus strains. In another aspect, the similar symptoms of the SARS-CoV-2 virus strains can be combined into a group, and after that the values (or accurate values) of the differentials within the metric of the differentials are ordered relative to multiple groups of symptoms.

Additionally, the predetermined symptom threshold values for all SARS-CoV-2 virus strains and the values within the metric of differentials may be updated so that the predetermined symptom threshold values reflect the latest understanding of symptoms of the SARS-CoV-2 virus strains. As additional studies are released, it is possible to update the accurate values for differentials, weighting coefficients for symptoms of the SARS-CoV-2 virus strains, complex symptoms of the SARS-CoV-2 virus strains.

The medical analytics platform may use a (deep or shallow) machine learning process to adjust the predetermined symptom threshold values for the SARS-CoV-2 virus strains, accurate values for differentials, weighting coefficients for symptoms of the SARS-CoV-2 virus strains, complex symptoms of the SARS-CoV-2 virus strains. Therefore, the metric of differentials is flexible that may be updated to identify additional symptoms that are found to be indicative of the SARS-CoV-2 virus strains. In the event of a future epidemic or pandemic, the disclosed metric of differentials can also be used to recognize the symptoms of a future virus.

The differentials within this metric of 16c are ordered in their values (or accurate values) relative to six most common symptoms of the SARS-CoV-2 virus strains: fever, cough, fatigue, dyspnea, anosmia, ageusia. For fever detection, a direct body temperature reading is collected and compared to the predetermined temperature threshold values for the person. Additionally, an increased heart rate is an indication of fever too. Data indicative of the heart activity of the person may be received, for example, from the heart monitor. Therefore, it is possible to detect a fever by detecting the person heart rate and comparing the detected heart rate to the predetermined heart rate threshold values for the person. The differences between the values of data received from a person (namely, body temperature, heart rate) and the predetermined symptom threshold values are the values of the differentials (3, −5, 15, 45, −12, −1) which then converted into accurate values (3, 1, 6, 8, 1, 1) indicative of the presence and severity of a fever.

Cough may be detected via acoustic engineering, e.g., using sound analysis, respiratory conditions are identifiable. Fatigue can be detected based in drop skin temperature (for example, as measured by the skin temperature thermometer), galvanic skin response data (for example, as measured by the electrodermal activity (EDA) sensor), reduced heart rate (for example, as measured by the heart monitor.) The differences between the values of data received from a person (namely, respiratory conditions, skin temperature, galvanic skin response data, reduced heart rate) and the predetermined symptom threshold values are the values of the differentials (22, −12, 3, 24, 21, 3 and 16, 21, 3, −2, 10, −5) which then converted into accurate values (9, 1, 2, 9, 9, 1 and 7, 9, 1, 1, 4, 1) indicative of the presence and severity of a cough and fatigue accordingly.

Difficulty or labored breathing (dyspnea) may be detected by identifying an increased respiratory rate (for example, as measured by the respiratory sensor) and a change in blood oxygenation (for example, as measured by the pulse oximetry sensor.) The loss of the sense of smell (anosmia) and reduced ability to smell (hyposmia) have well established diagnostic tests, such as the University of Pennsylvania Smell Identification Test (UPSIT) and "Sniffin' Sticks", a test of nasal chemosensory performance based on pen-like odor-dispensing devices. The loss of sense of taste (ageusia) and reduced ability to taste sweet, sour, bitter, or salty substances (hypogeusia) can be detected via plurality of various sensors and biosensors. The differences between the values of data received from a person (namely, respiratory rate, change in blood oxygenation, smell test data, taste sensors data) and the predetermined symptom threshold values are the values of the differentials (35, −11, −1, 13, 17, −2 and 13, 18, −2, 11, −2, 32 and 19, 3, 43, 23, −12, 2) which then converted into accurate values (6, 1, 1, 4, 6, 1 and 4, 6, 1, 4, 1, 8 and 7, 2, 8, 7, 1, 2) indicative of the presence and severity of a dyspnea, anosmia, and ageusia accordingly.

FIG. 17 illustrates other examples of the metrics of differentials of the present invention. The differentials can be combined into multiple groups based on the differences in the values of the differentials (accurate values), and after that the groups of the differentials within the metric of the differentials are ordered relative to symptoms of the SARS-CoV-2 virus strains. 17a shows example of groups of the differentials. The values of the differentials such as −3, −11, 14, 3, 12, −5, 15, 2, −12, 6 are accordingly combined into multiple groups of the differentials № 1, № 2, № 3, № 4 that include the corresponding values of the differentials: −3, −11, −5, −12 and 14, 3, 12, 15, 2, 6 and 14, 15 and −12, 15.

In other aspects, the similar symptoms of the SARS-CoV-2 virus strains can be combined into a group, and after that the values of the differentials (accurate values) within the metric of the differentials are ordered relative to multiple groups of symptoms. 17b shows example of groups of symptoms. The SARS-CoV-2 symptoms such as fever, shortness of breath, sweating, fatigue, chills, cough, rapid heartbeat, headache, muscle pain, nausea, loss of appetite, increase of respiration rate are accordingly combined into multiple groups of symptoms № 1, № 2, № 3, № 4 that include the similar symptoms: chills, fatigue, muscle pain; cough, fever, headache, sweating; rapid heartbeat, increase of respiration rate, shortness of breath; nausea, loss of appetite.

In other aspects, the weighting coefficient for each symptom of the SARS-CoV-2 virus strain is determined. The weighting coefficient characterizes the severity level of symptom. The values of the differentials (accurate values) within the metric of the differentials are then ordered relative to the weighting coefficients. 17c shows example of weighting coefficients. The symptoms of the SARS-CoV-2 virus strains such as fever, shortness of breath, sweating, fatigue, chills, cough, rapid heartbeat, headache, muscle pain, nausea, loss of appetite, increase of respiration rate have accordingly weighting coefficients 3, 4, 6, 4, 4, 3, 4, 4, 5, 5, 2, 3 that characterize the likelihood and severity these symptoms. Thereafter the values (or accurate values) of the differentials within the metric are ordered relative to these weighting coefficients.

In other aspects, it is determined the complex symptom that shows the correlation of the several symptoms of the SARS-CoV-2 virus strains. After that the values of the differentials (accurate values) within the metric of the differentials are ordered relative to complex symptoms. 17d shows example of complex symptoms within the plurality of the symptoms: fever, shortness of breath, sweating, fatigue, chills, cough, rapid heartbeat, headache, muscle pain, nausea, loss of appetite, increase of respiration rate. The complex symptoms such as fever, shortness of breath may cause the symptoms such as rapid heartbeat, headache, muscle pain, fatigue; cough, chills, increase of respiration rate, sweating.

Figure 18:
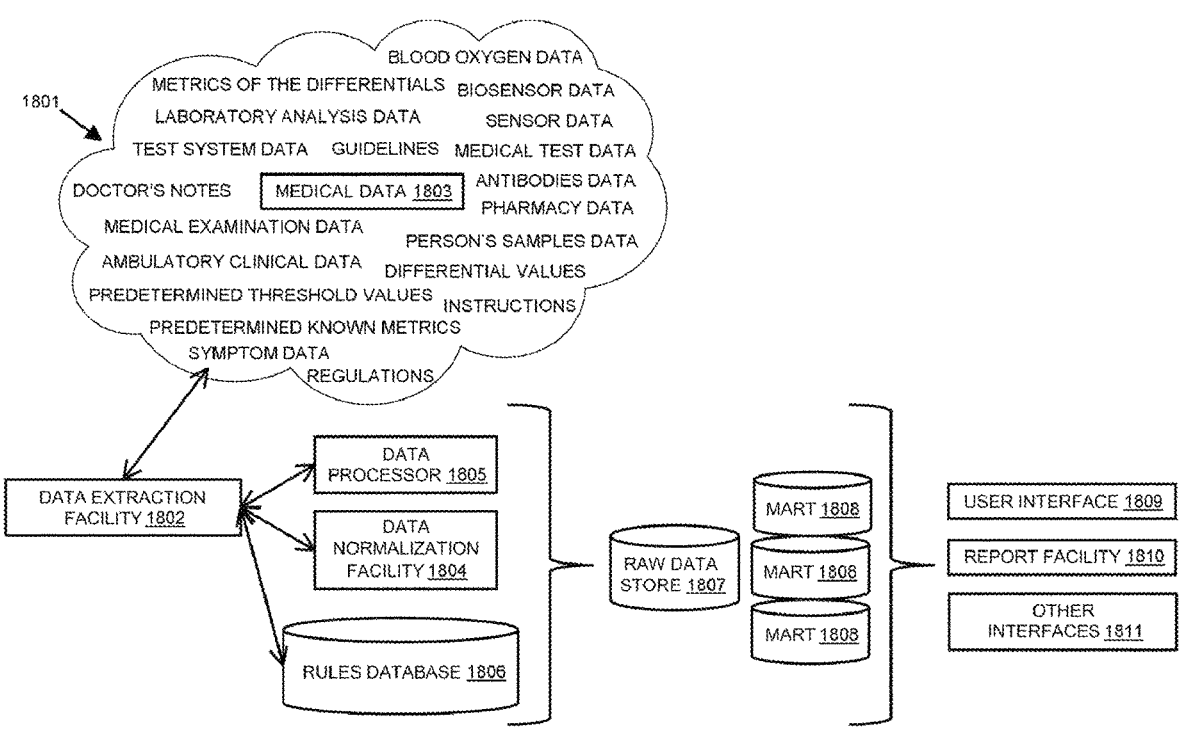
FIG. 18 is a diagram illustrating the medical analytics platform of the invention.

FIG. 18 is a diagram illustrating the medical analytics platform 1801 of the present invention. A data extraction facility 1802 can extract data from a plurality of medical data 1803 to enable the real-time collection, processing, analysis and centralized storage of medical information in a databases. Real-time, continuous data ingestion may come from various medical data 1803 which may include sensor data, biosensor data, laboratory analysis data, medical test data, test system data, person's sputum or saliva samples data, antibodies data, blood oxygen data, medical examination data, ambulatory clinical data, pharmacy data, doctor's notes, medical regulations, medical instructions, medical guidelines, predetermined symptom threshold values, differential values, symptom data, metrics of the differentials, predetermined known metrics, etc.

The medical analytics platform 1801 enables ingestion and analysis of the medical data by converting the data to standardized data elements using a data normalization facility 1804 and a data processor 1805. The data processor 1805 may transform data from the various formats in which it exists. The rules database 1806 may provide rules to the data processor 1805 for analysis of medical data 1803. To do this, the rules database 1806 stores rules, instructions, guidelines, attributes, characteristics, and criteria that are used in this analysis. The data are manipulated and analyzed by the medical analytics tools. Tools may enable data mining, the machine learning techniques, etc. The analytics may be modular, such as by SARS-CoV-2 virus strain, predetermined symptom threshold value, differential, symptom, etc. The analytics may generate granular comparative data. The analytics may also enable predictive modeling.

The medical analytics platform 1801 may also comprise tools for analytic model building. For example, to build a disease model for SARS-CoV-2 virus strain, aspects of the disease that might be of interest, such as person's symptom data values, may be obtained by a plurality of sensors or a test system for an indication of a viral infectious disease. These aspects may be defined as inputs to the model in terms of rules, instructions, guidelines, attributes, characteristics, criteria, etc. These inputs may be defined in a rules database 1806 and updated periodically or as needed. Data may be analyzed according to rules of the model by the medical analytics platform 1801 to enable determining a disease in a person. The data may be stored in a flexible data warehouse, such as a raw data store 1807 and a data mart 1808. The data may be certified. Interfaces to the medical analytics platform 1801, such as a user interface 1809, report facility 1810, and other interfaces 1811, may be used to search and view data, initiate analyses, visualize data, generate reports, generate a tracking page, etc.

Figure 19:
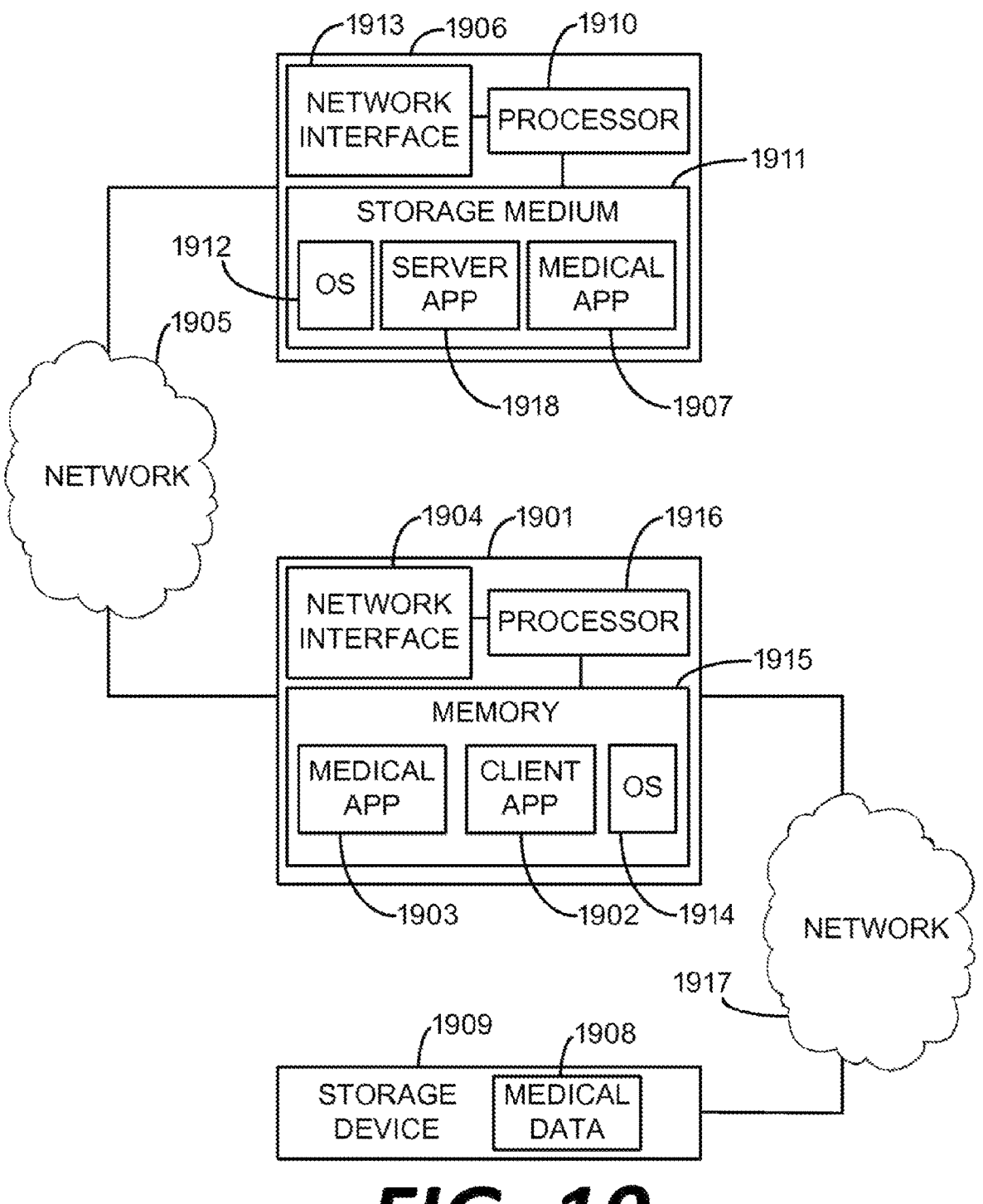
FIG. 19 is a diagram illustrating components for implementing the medical analytics platform of FIG. 18.

FIG. 19 is a diagram illustrating components for implementing the medical analytics platform of FIG. 18 using one or more medical applications, including a client computer 1901 having a client application 1902 configured to control access of one or more medical applications (e.g., a medical application 1903) to one or more client computer resources, such as a network interface 1904. The client computer 1901 can include one or more client computers, or one or more other computers configured to process medical data. The client application 1902 can be configured to communicate over a network 1905 with a server 1906 having one or more medical applications, such as the medical application 1907. Further, the client application 1902 can be configured to receive information (e.g., medical data 1908) from a storage device 1909, such as a database coupled to the client computer 1901 (e.g., using a local area network, a wide area network, etc.) In an example, the client computer 1901 can include a medical application 1903, such as at least partially received (e.g., downloaded) from the server 1906, etc. In certain examples, the client computer can include a plurality of medical applications at least partially received (e.g., downloaded) from the server 1906.

The client application 1902 can be configured to provide information to one or more medical applications stored at least partially on the client computer 1901, and to control access of one or more of the medical applications 1903 to one or more client computer resources, such as a network interface 1904. In an example, the server 1906 can include a processor 1910 (e.g., one or more processors) coupled to a storage medium 1911 (e.g., one or more hard drives, an array of hard drives, etc.) The storage medium 1911 can include a general-purpose server operating system 1912 (e.g., Linux, Microsoft Windows Server, IBM Advanced Interactive eXecutive (AIX), etc.) stored or installed thereon. In certain examples, the server operating system 1912 can manage one or more server software processes, and can include commercial or open source software, such as Apache/Tomcat, JBOSS, or IIS, or others to manage server-based processes. In an example, the server 1906 can include a physical network interface 1913 coupled to the network 1905 for communication with the client computer 1901.

The client computer 1901 can include an operating system 1914 (e.g., a general purpose operating system) stored or installed in a memory 1915 and configured to be executed on a processor 1916 coupled to the memory 1915. The client operating system 1914 can include, for example, Microsoft Windows 7, Microsoft Windows XP, Linux, Redhat, Ubuntu, Apple OS X, Google Android, Apple ITunes, or one or more other client operating systems. In certain examples, the client computer 1901 can be coupled to a storage device 1909, such as via a local area network 1917. In an example, the external storage device 1909 can include a remote server, such as via a wide area network, and can include medical data 1908 stored thereon. In an example, the external storage device 1909 can include a database of medical data, a medical imaging archive, clinical informatics storage, a laboratory/pathology system, an imaging modality, or other clinical users and information resources.

A physical network interface 1904 can be coupled to the processor 1916. In certain examples, the physical network interface 1904 can be configured to couple the client computer 1901 to the network 1905, such as for communication with server 1906. In an example, the physical network interface 1904 can couple the client computer 1901 to the network 1917, such as for communication with the external storage device 1909. In an example, the operating system 1914 can include one or more client operating system resources, such as a network interface. In an example, the operating system 1914 can include a resource configured to control access to the physical network interface 1904.

The client computer 1901 can include a client workstation running a Windows based, or other, operating system, a medical device (e.g., a magnetic resonance imaging (MRI) scanner) including a general purpose processor or memory, a mobile device (e.g., a laptop), an etc. In certain examples, the client computer 1901 can include one or more inputs (e.g., keyboard, mouse, etc.) configured to receive user requests, such as a user request for a specific medical application, a user request to process data on a medical application, account information, etc. In an example, the storage medium 1911 on the server 1906 can include one or more medical applications (e.g., a medical application 1907) stored thereon. In an example, the medical application 1907 can include a software application or executable configured to perform one or more actions on information, such as one or more items of medical data.

The client computer 1901 can include the client application 1902 stored on the memory 1915 and configured to initiate and control the execution of one or more medical applications, such as the medical application 1907. In other examples, the client application 1902 can include an executable image. In another example, the client application 1902 can include one or many binary libraries or intermediate library objects controlled by a higher-level executable image. The client application 1902 can communicate with a server application 1918 for download or control of the medical application 1907 as discussed in more detail below.

Although FIG. 19 illustrates the client computer 1901 as a single client computer, in other examples, multiple client computers can be coupled to the server 1906 over the network 1905. Accordingly, because the client computer 1901 can include multiple client computers having an instance of the client application 1902 executing thereon, multiple instances of the client application 1902 can communicate simultaneously with server application 1918. Additionally, although the server 1906 illustrated in FIG. 19 includes a single server, in certain examples, the server 1906 can include a distributed server, and can include multiple sites having synchronized databases coupled to the network 1905.

In an example, the medical application 1907 can include a virtualized application configured to be executed on a virtual platform. In an example, the medical application 1907 can include a software application that is fully installed within a container file that includes a complete run-time environment for the application. The container can include a virtualized operating system having a conventional medical application installed thereon, including an application .exe and .dll components, along with other related services including a database management system. In an example, the medical application 1907 can include a VMWare, CITRIX, or other equivalent based construct or virtual operating system.

Figure 20:
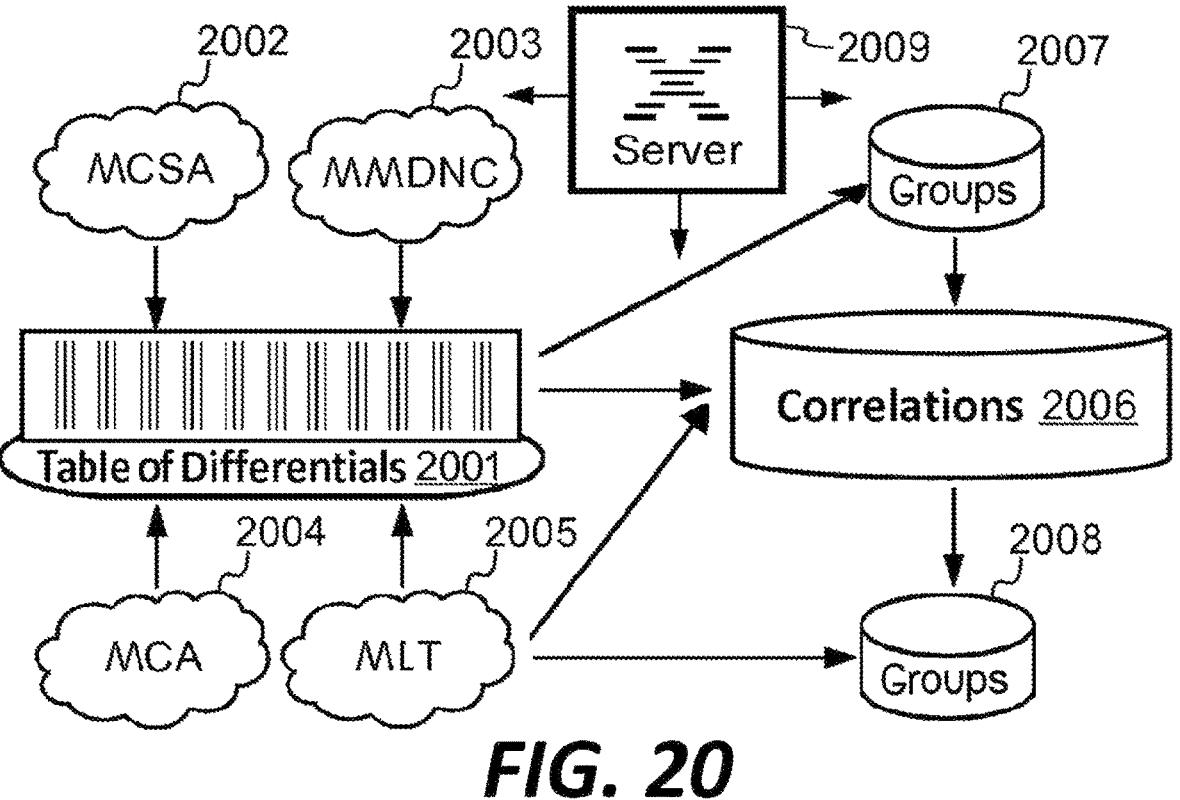
FIG. 20 is a diagram illustrating the analysis of medical data of the invention.

FIG. 20 is a diagram illustrating the analysis of medical data of the present invention. The metrics of differentials of FIGS. 14-17 are grouped into the table of differentials 2001 and stored on a server 2009 or a Cloud server. The table 2001 (metrics of FIGS. 14-17) comprises all differentials obtained for major COVID variants, which are then processed using the method of combinatorial statistical analysis 2002, the mathematical method of dense network of curves 2003, the methods of cluster analysis 2004, the machine learning techniques 2005 to detect tendencies and correlations 2006. In another aspect, the differentials within the table of differentials 2001 are combined into multiple groups of differentials 2007 based on the differences in the differentials. The differentials that were not included in the groups 2007 are not taken into account in the further analysis of the set of differentials. Based on the multiple groups of differentials 2007 detected, the set of differentials is analyzed using these methods to detect tendencies and correlations 2006 indicative of relationships between the groups of the differentials.

A set of the all detected tendencies and correlations 2006 are created. The correlations within the set are further analyzed by using the methods of cluster analysis 2004 to define the same or similar correlations and combining these correlations into a group 2008. The correlations that were not included in the groups are not taken into account in the further determination of COVID disease in a patient. Thus the multiple groups of correlations 2008 having same or similar correlations are created. All the data is stored in the databases on the server 2009. Then, these databases are analyzed by using machine learning techniques 2005 that are applied on the data saved on the databases. In another embodiment of the present invention, the databases are uploaded to the cloud server that is shared by multiple computers.

Figure 21:
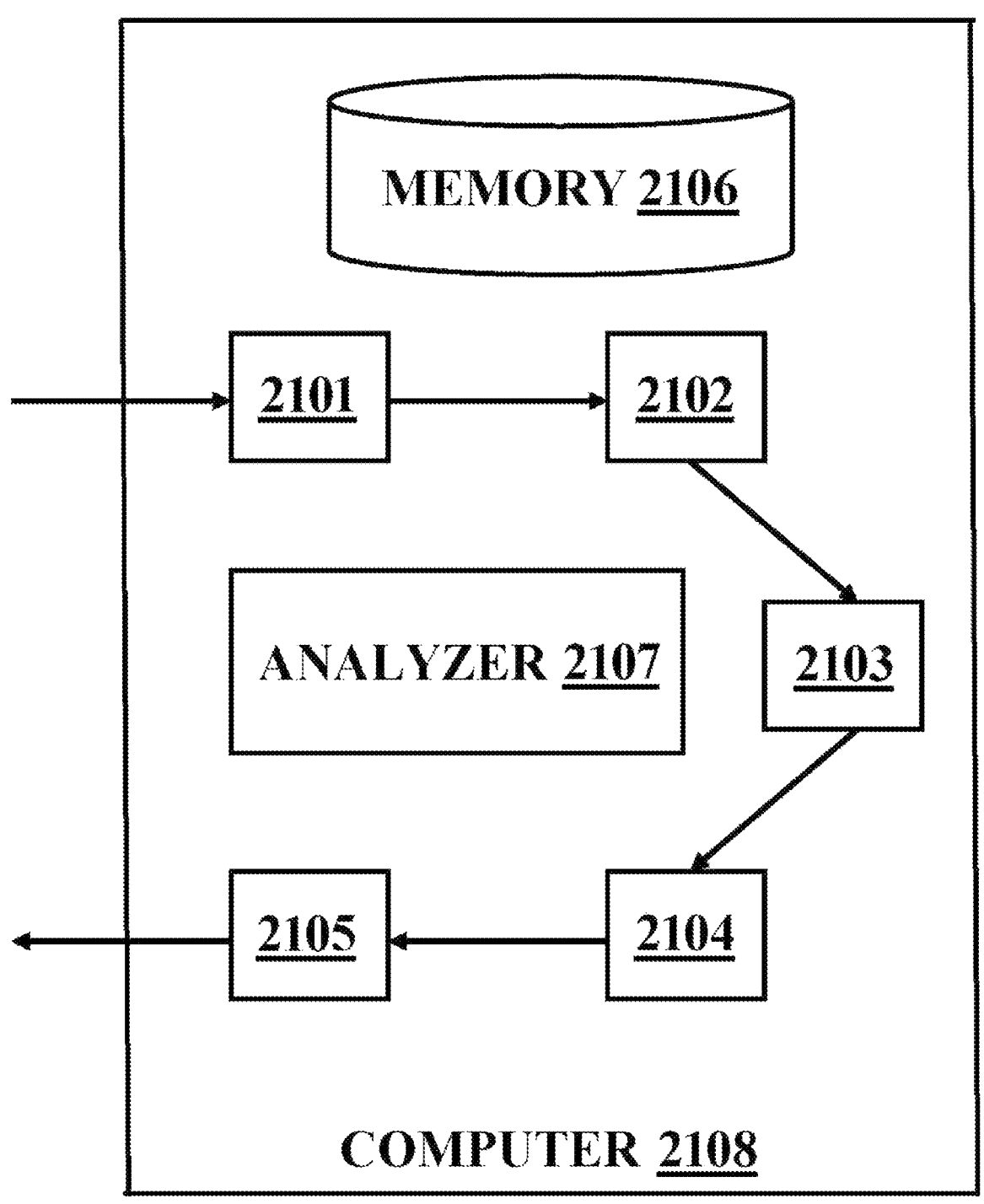
FIG. 21 is a diagram illustrating hardware components for implementing the combinatorial data analysis.

FIG. 21 is a diagram illustrating a hardware system for implementing the method of combinatorial statistical data analysis (MCSA) 2002 of FIG. 20. The system consists of 5 software components: 1) unit 2101 for lists selection (or for at least one database selection) allowing the user to enter the values and/or terms of interest in a combinatorial fashion in different lists, 2) a co-occurrence frequency retrieval unit 2102 wherein the unit extracts the co-occurrence and separately occurring statistics of the values and/or terms of interest in a combinatorial fashion from the databases, 3) a normalization unit 2103 wherein the ratio of co-occurrence statistics of the values and/or terms to the separately occurring statistics are calculated using various formulas, 4) data integration unit 2104 where the normalized data is integrated on a matrix, 5) the display unit 2105 where the data is displayed to the end-user in a graphical format.

The units 2101-2105 implemented in the central memory 2106 of a computer 2108 or on one of its storage units from a storage medium, for example, a CD-ROM, or through the transmission of a data feed. Actions on values and data are implemented through the analyzer 2107 that is loaded into the computer 2108. The aim of the method of combinatorial statistical analysis is to allow the user to enter lists of the numbers and/or terms in double or triple combinations, and compare it with each other to find specific tendencies and correlations indicative of the mathematical (statistical) or logical relationships between the values.

The method of combinatorial statistical analysis functions in the following fashion: 1) at least one database is chosen by the user, 2) the values and/or terms of interest are entered by the user in at least two lists with respect to the order of interest, 3) determination of co-occurrence as well as separately occurring frequencies for the values and/or terms of different lists in a combinatorial fashion, 4) data normalization via ratio calculation of the co-occurrence statistics to the separately occurring statistics using different ratio formulas, 5) elimination of errors and data normalization according to the normalization step, 6) graphical display of the results to the user.

The method of combinatorial statistical analysis allows the user to search for symptoms of major COVID variants, and to read and interpret the results in the following fashion: 1) the selection of the main database, 2) entrance of the values of differentials and values of patient data obtained into list 1 and list 2, 3) determination of the occurring frequencies of values in list 1 and list 2 separately on the database, 4) determination of the co-occurrence of frequencies of values in list 1 and values in list 2 in a combinatorial fashion, 5) ratio normalization of the values of frequencies of list 1 and list 2 in a combinatorial fashion, 6) error elimination with respect to results of the normalization, 7) integration of the obtained data on a matrix and displaying to the end-user using the color code. The results will show the user which symptoms of major COVID variants are probable based on the statistics of the data in table 2001.

Or, for example, we can compare and analyze the set of differentials and the set of predetermined symptom threshold values for major COVID variants to detect diseases of major COVID variants. For this we will use the method of combinatorial statistical analysis 2002 to search for COVID disease in the following fashion: 1) the selection of the main database, 2) entrance of the values of differentials and predetermined symptom threshold values into list 1 and list 2 (as below using the entrance unit), 3) determination of the occurring frequencies of values in the list 1 and list 2 separately on the database, 4) determination of the co-occurrence frequencies of values in list 1 and values in list 2 in a combinatorial fashion, 5) ratio normalization of the values of frequencies of list 1 and list 2 in a combinatorial fashion, 6) error elimination with respect to results of the normalization, 7) integration of the obtained data on a matrix and displaying to the end-user using the color code. The results will show the user which diseases of major COVID variants are probable based on the statistics of the data in table 2001.

The method of combinatorial statistical analysis 2002 is used to compare pairs of datasets in order to calculate statistics and find tendencies and correlations 2006 that are the mathematical (statistical) or logical relationships between the values among the following fifteen pairs of datasets: 1) differentials and patient's biochemical and bio-physical data, 2) differentials and predetermined symptom threshold values for major COVID variants, 3) differentials and patient's individual physiological parameters, 4) differentials and diseases that accompany COVID-19, 5) differentials and additional patient data, 6) patient's biochemical and biophysical data and predetermined symptom threshold values for major COVID variants, 7) patient's biochemical and biophysical data and patient's individual physiological parameters, 8) patient's biochemical and biophysical data and diseases that accompany COVID-19, 9) patient's biochemical and biophysical data and additional patient data, 10) predetermined symptom threshold values for major COVID variants and patient's individual physiological parameters, 11) predetermined symptom threshold values for major COVID variants and diseases that accompany COVID-19, 12) predetermined symptom threshold values for major COVID variants and additional patient data, 13) patient's individual physiological parameters and diseases that accompany COVID-19, 14) patient's individual physiological parameters and additional patient data, 15) diseases that accompany COVID-19 and additional patient data.

In order to detect tendencies and correlations 2006 in a large array of data, e.g., comparing three or more datasets and finding tendencies and correlations there, the mathematical method of dense network of curves 2003 is used, for instance, to detect correlations between differentials, patient's biochemical and biophysical data, patient's individual physiological parameters, patient's diseases that accompany COVID-19, and additional patient data. The mathematical method of dense network of curves allows for a superior level of analysis of the aforementioned data, both qualitatively and quantitatively.

Figure 22:
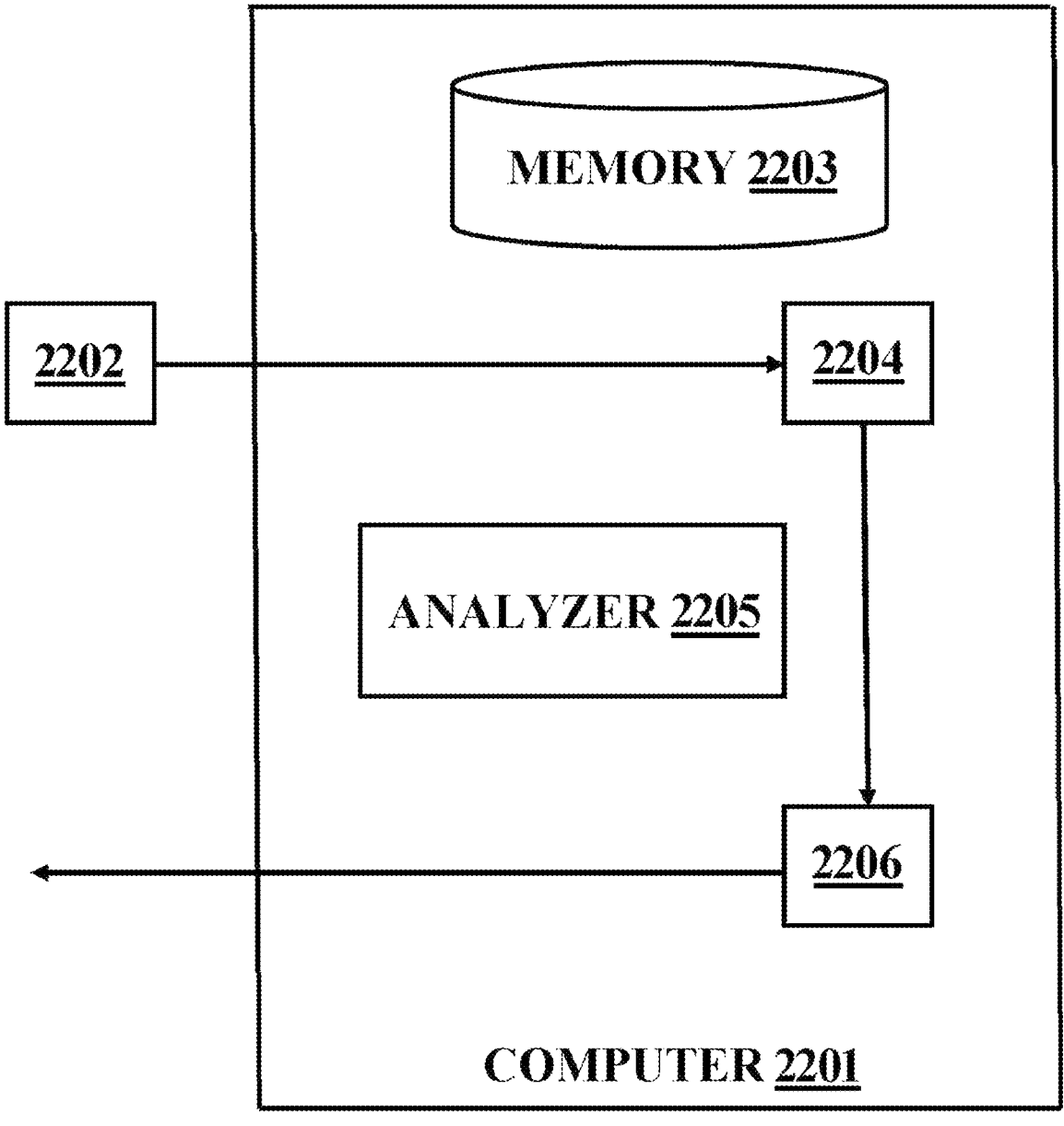
FIG. 22 is a diagram illustrating hardware components for implementing the regression data analysis.

FIG. 22 is a diagram illustrating a hardware system for implementing the mathematical (regression data analysis) method of dense network of curves (MMDNC) 2003 of FIG. 20. The system of FIG. 22 includes the computer 2201, the chronological set of numerical values 2202, the central memory 2203, the unit of data entry 2204, the analyzer 2205, the display unit 2206. The chronological set of values 2202 is entered into the unit of data entry 2204 stored in the central memory 2203 of a computer 2201 or on one of its storage units from a storage medium, for example, a CD-ROM, or through the transmission of a data feed. The numerical values of the chronological set 2202 are used in the system in order to construct a dense network of curves constituting the topological structure of the set. Operations on the numerical values of the chronological set 2202 according to the mathematical formula (that be given below) are implemented through the analyzer 2205 that is loaded into the computer 2201.

The system is used to construct a dense network of curves constructed mathematically from numerical data of the chronological set 2202 (e.g., the values of the patient's biochemical and biophysical data or the values of the differentials) and defined by a primary parameter (the number of data points used) and a secondary parameter (the scale parameter). The secondary parameter (the scale parameter) can be the interval of time separating two consecutive data points, for example, minutes, hours, or days, since the onset of the illness or the patient was in quarantine. Other types of intervals can also be used. For differentials, for example, the scale can be expressed in terms of the number of same values of differentials to one patient or the number of same values of differentials to one major COVID variant. Or, for example, a dense network of curves can be constructed mathematically from the values of differentials of the chronological set 2202 and defined by a primary parameter (the number of patients with ischemic heart disease and tuberculosis) and a secondary parameter (the duration of the patient's illness or having immunity).

The system can use any of the following regressions: 1) regression of order zero, otherwise known as average, 2) first order regression, otherwise known as linear regression, 3) second order regression, otherwise known as quadratic regression, 4) regression of order greater than 2. The curves of this network belong to one of the following categories: 1) moving regression (MR) of degree zero, known as the moving average (MA), 2) MR of the first degree, known as the moving linear regression (MLR), 3) MR of the second degree, which we will call the moving quadratic regression (MQR), 4) MR of the kth degree, which we will call the moving k regression (MKR).

The present invention is based on the utilization of a dense network of MRs corresponding to a large set of values of the primary parameter, chosen according to defined criteria because in this case-characteristic figures appear strikingly on the monitor of a computer 2201. The network described in what follows is composed of MLRs. It is on the presence of these characteristic figures within the dense network that rests the ability to the analysis of the data and obtain precise and reliable information. The method can also use adjusted data, for example, averaged or weighted data.

The necessary conditions under which the characteristic figures appear in the network are the following: 1) the network must contain a large number of MLRs, greater than about 50, 2) the set of the values of the primary parameter must extend over a sufficiently large range, 3) the distribution of the values of the primary parameter must be such that the corresponding network has a uniform density on average. In practice, criterion 3 is satisfied when the values of the primary parameter constituting the set grow slowly and uniformly. Furthermore, if wished, one can slightly modify the density, for example, by making the network denser for smaller values of the primary parameter.

The algebraic formula used in the present invention is:

$$nk = n1 + (k-1)a + k(k-1)N(N-1)[nN - n1 - (N-1)a]$$

where:
k = {1, . . . N},
N is the number of curves in the network,
$n_1$ is the first term of the set,
$n_N$ is the $N^{th}$ term of the set,
a is the interval between $n_1$ and $n_2$.

Taking N=100, $n_1$=8, $n_N$=1502, and a=8 as an example, one obtains for the primary parameter the following set of values: {8, 16, 24, 33, 41, 50, 59, 68, . . . , 1351, 1372, 1393, 1415, 1436, 1458, 1480, 1502}. This set of values generates a network of 100 MLRs which has a uniform density on average and extends over a large range. The characteristic figures seen on the monitor of the computer belong to one of the following two types: 1) cord, and 2) envelopes. A cord is a pronounced condensation of curves that stands out from a less dense background of curves of the network. An envelope outlines the boundary of a group of curves of the network. A characteristic figure attracts or repels the representative curve of the data, depending on its type, its shape and its relative position to the representative curve of the data. The more marked the characteristic figure, the stronger the attraction or the repulsion.

The analysis of the data requires the examination of the ensemble of the cords and envelopes and the representative curve of the data up to a given moment, over a sufficiently large interval of consecutive data points. An interval is considered sufficiently large when it contains a peripheral characteristic figure at the top of the network exhibiting a convex upward turning point and another one at the bottom exhibiting a convex downward turning point. The ensemble of the cords and envelopes and the representative curve of the data observed over a sufficiently large interval are referred to as a spatial configuration. Qualitative and quantitative indications are obtained from a spatial configuration by determining which characteristic figures specifically attract and which characteristic figures specifically repel the representative curve of the data, and this is achieved through the examination of numerous and varied spatial configurations.

Figure 23:
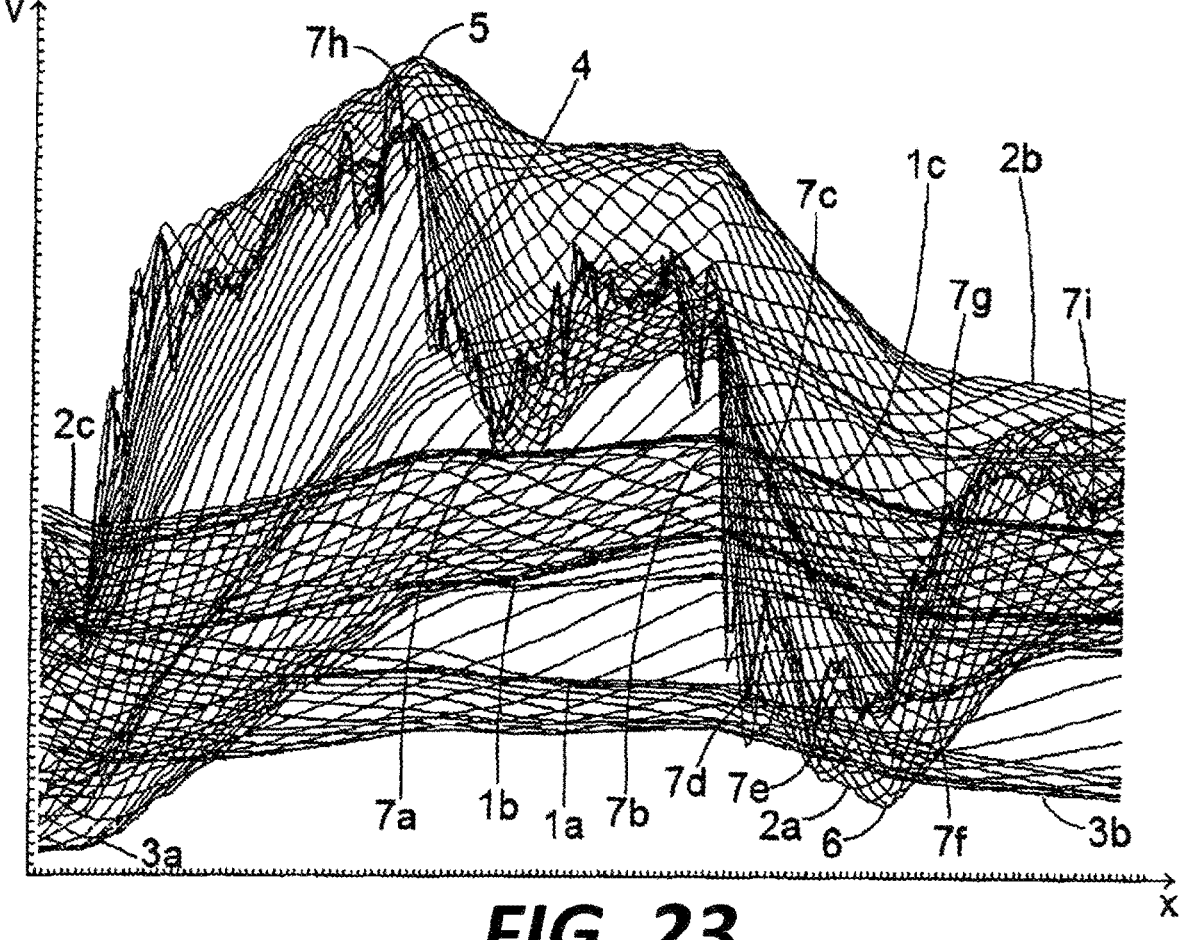
FIG. 23 illustrates a graphical example of using the regression data analysis.

FIG. 23 illustrates a graphical example of using the mathematical method of dense network of curves 2003 of FIG. 20 in which characteristic figures and spatial configurations appear. In FIG. 23, which represents a network of one hundred and fifty curves based on linear regressions calculated by the formula described above, one can see characteristic figures containing cords 1a, 1b, 1c, envelopes 2a, 2b, 2c, mixed figures (which is both a cord and an envelope) 3a, 3b and the representative curve of the set of values 4, in the form of a continuous curve.

The network contains on the upper part a peripheral characteristic figure presenting a maximum 5 and on the lower part a peripheral characteristic figure presenting a minimum 6. A characteristic figure will attract-repulse the representative curve of the chronological set of values according to its type, its shape, and its position in relation to the representative curve. For example, it is, at abscissa x0, the "attractive-repulsive" effect of the characteristic figures on the representative curve of the chronological set of values, without figure-crossing 7a, 7d, 7e, 7h, 7i and with figure-crossing 7b, 7c, 7f, 7g.

As shown in FIG. 20 by using the method of combinatorial statistical data analysis 2002, the mathematical (regression data analysis) method of dense network of curves 2003, the methods of cluster analysis 2004, it is possible to analyze all data stored in the databases on the server 2009 in the system of the present invention in order to find tendencies and correlations 2006. Also, the method of combinatorial statistical analysis 2002, the mathematical method of dense network of curves 2003, the methods of cluster analysis 2004 can be employed independently as machine learning techniques using the aforementioned databases on the server 2009 to predict new variants of COVID-19, or create novel learning models for detecting new COVID variants.

The methods 2002-2005 disclosed above are used to calculate statistics, and detect and analyze tendencies and correlations 2006 that are the mathematical or logical relationships between the values in the following data: 1) biochemical and biophysical data obtained from sensors and biosensors (for detecting cough, sputum, shortness of breath, fever, anosmia, ageusia, nasal congestion, runny nose, sore throat, muscle pain, joint pain, headache, fatigue, abdominal pain, vomiting, diarrhea, diabetes, lung diseases, cardiovascular diseases, ischemia, hypertension), 2) biochemical and biophysical data obtained from laboratory medical examinations (chest CT scans, checking for elevated body temperature, checking for low blood oxygen level), 3) biochemical and biophysical data obtained from laboratory medical tests (the reverse transcription polymerase chain reaction test, nucleic acid test, serological test, molecular test CRISPR, isothermal nucleic acid amplification, digital polymerase chain reaction, microarray analysis, next-generation sequencing, antigen tests for antigen proteins, rapid diagnostic test, enzyme-linked immunosorbent assay test, neutralization assay, chemiluminescent immunoassay), 4) patient's individual data (whether they have tuberculosis, diabetes, pregnancy, severe immunosuppression, lymphoma, oncological diseases, ulcers, ischemic heart diseases, cardiovascular pathologies, nervous diseases, as well as their sex, age, height, weight, ethnicity, area of living, quarantine stay length, etc.)

The method of combinatorial statistical analysis 2002, the mathematical method of dense network of curves 2003, the methods of cluster analysis 2004, the machine learning techniques 2005 can be used to detect tendencies and correlations 2006 in this data in order to diagnose the patient's viral disease, identify the major COVID variant that is closely related to the patient's disease, find differences between diseases caused by the major COVID variants, update and revise predetermined symptom threshold values for the major COVID variants, predict the individual traits of the course of the patient's viral disease, detect individual traits of the patient's diseases that accompany COVID-19, detect the post-COVID syndrome of the patient. Detected tendencies and correlations that are the mathematical or logical relationships between the values can then be used to create machine learning techniques for detecting new COVID variants.

The method of combinatorial statistical analysis 2002 compares and analyze the values of biochemical and biophysical data obtained from sensors and through laboratory medical tests, laboratory medical examinations with predetermined symptom threshold values indicating to any of the major COVID variants: Alpha (lineage B.1.1.7), B.1.1.7 with E484K, Beta (lineage B.1.351), Gamma (lineage P.1), Delta (lineage B.1.617.2), Lambda (lineage C.37), Mu (lineage B.1.621), Epsilon (lineages B.1.429, B.1.427, CAL.20C), Zeta (lineage P.2), Theta (lineage P.3), Eta (lineage B.1.525), Iota (lineage B.1.526), Kappa (lineage B.1.617.1), Omicron (lineage B.1.1.529), Lineage B.1.1.207, Lineage B.1.1.317, Lineage B.1.616, Lineage B.1.618, Brazilian variant, Centaurus variant, Deltacron variant, etc. The data is included in lists 1 and 2 respectively, and statistics are calculated using the combinatorial approach.

In cases when a sensor reading or test result exceeds the predetermined symptom threshold values, the resulting differentials will be positive. All major COVID variants are ranked according to the total number of positive differentials they have, from the higher total to the lower total. The top-ranked COVID variant, which has more positive differentials than other variants, will be the patient's diagnosed viral disease of major COVID variant (the corresponding diagnosis is provided), and the next COVID variant will be the closely related major COVID variant, which is the closest to the patient's diagnosed viral disease (the diagnosed major COVID variant that has infected the patient).

When the mathematical method of dense network of curves 2003 is used to analyze all data stored in the databases on the server 2009 in the system of the present invention and interpret results, the primary parameter includes both values of differentials and predetermined symptom threshold values for major COVID variants, and the secondary parameter includes the values of the patient's biochemical and biophysical data, which are periodically updated. The resulting cords and envelopes for the representative curve of the data will show the diagnosed major COVID variant (i.e., the data forming the cord or envelope are located closer to the representative curve of the data) and the closely related major COVID variant (i.e., the data forming the characteristic figure are located further away from the representative curve of the data).

The viral disease of a major COVID variant and the closely related major COVID variant can be detected separately using the method of combinatorial statistical analysis 2002, the mathematical method of dense network of curves 2003, the methods of cluster analysis 2004. Then all detected major COVID variants can be summed up and ranked using both methods, and the top two COVID variants may be interpreted as the patient's viral disease of major COVID variant, and as the major COVID variant that is closely related to the patient's disease respectively.

Using the method of combinatorial statistical analysis 2002 to calculate statistics for the values of differentials for all major COVID variants, and the values of differentials for the original COVID-19 virus strain, which are included in lists 1 and 2 respectively, the probability of the patient being infected by a major COVID variant is calculated, and the differences between this viral disease and the original COVID-19 virus strain are determined, in case the values of differentials of the diagnosed disease do not match the values of differentials or predetermined symptom threshold values for the original COVID-19 virus strain.

In the same way, individual traits of the viral disease course are determined, wherein all values of differentials and values of patient's biochemical and biophysical data obtained from sensors and through laboratory medical tests, laboratory medical examinations are included in lists 1 and 2 respectively, and the biochemical and biophysical data are periodically updated. By calculating statistics for differentials and biochemical and biophysical data obtained over the course of the patient's viral disease using the combinatorial method, it is possible to see the progress of the viral disease. For example, if the values of differentials increase over time, then the disease is intensifying. Conversely, if the values of differentials decrease over time, then the disease is abating.

The resulting statistical tendencies and correlations 2006 may be uploaded into the method of combinatorial statistical analysis 2002 again and compared, for example, with the patient's individual physiological parameters and additional patient data. Matches with certain patient's individual physiological parameters found therein might show individual traits of the patient's disease course. If the resulting tendencies and correlations 2006 are compared with the diseases that accompany COVID-19, then the combinatorial method might show individual traits of the patient's diseases that accompany COVID-19, as well as their possible post-COVID syndrome.

Also, in order to detect tendencies and correlations 2006, the mathematical method of dense network of curves 2003 is used, wherein the primary parameter includes both values of differentials and predetermined symptom threshold values for major COVID variants, and the secondary parameter includes statistical data of major COVID variants by sex, age, and region. The resulting spatial configuration represented by cords and envelopes and applied to a representative curve of the data will show the differences between major COVID variants, in case some characteristic figures will be detected that can be compared using the primary parameter and the secondary parameter data.

So, if the primary parameter includes both values of differentials and predetermined symptom threshold values for major COVID variants, the secondary parameter includes statistical data of major COVID variants by sex, age, and region, then the characteristic figures in the spatial configuration might point out predetermined symptom threshold values to be updated, in case the characteristic figures show much difference in their secondary parameters and/or their positions in relation to the representative curve of the data. When the mathematical method of dense network of curves 2003 is used to determine the post-COVID syndrome, the primary parameter includes both the data about the patient's diseases that accompany COVID-19 and the patient's individual physiological parameters, and the secondary parameter includes both the values of differentials and the values of patient's biochemical and biophysical data. The characteristic figures in the spatial configuration might point out tendencies and correlations between the data that are used to generate the characteristic figures. The values of the primary parameter for the characteristic figures will show the corresponding accompanying diseases, which, together with the patient's viral disease diagnosed as a major COVID variant, can be used to determine a possible post-COVID syndrome.

Alternatively, the primary parameter may include both the data about the patient's diseases that accompany COVID-19 and the patient's individual physiological parameters, and the secondary parameter includes the values of biochemical and biophysical data that are updated periodically. The characteristic figures in the spatial configuration might point out tendencies and correlations 2006 that may be used to determine the individual traits of the course of the patient's diseases that accompany COVID-19, based on the primary parameter with the characteristic figure, in case the data of the secondary parameter for the same characteristic figure change faster (meaning that the accompanying disease is intensifying) or slower (meaning that the accompanying disease is abating). Also, both the primary parameter and the secondary parameter may include the data from any of the detected tendencies and correlations 2006, which will be analyzed and interpreted again using the mathematical method of dense network of curves 2003.

It should be obvious to those skilled in the art that the data stored in the databases on the server 2009 can be analyzed using different mathematical methods. For example, the cluster analysis 2004 can be used for this. Cluster analysis is the task of grouping a set of objects in such a way that objects in the same group (called a cluster) are more similar to each other than to those in other groups (clusters). The cluster analysis 2004 can use the differences in the values of the all data stored in the databases on the server 2009 in the system of the present invention to define multiple groups of the values and to find tendencies and correlations 2006 in each group. For example, the cluster analysis uses the differences in the differentials within the table 2001 to define multiple groups of the differentials 2007 and to find tendencies and correlations 2006 in each group of the differentials.

Figure 24:
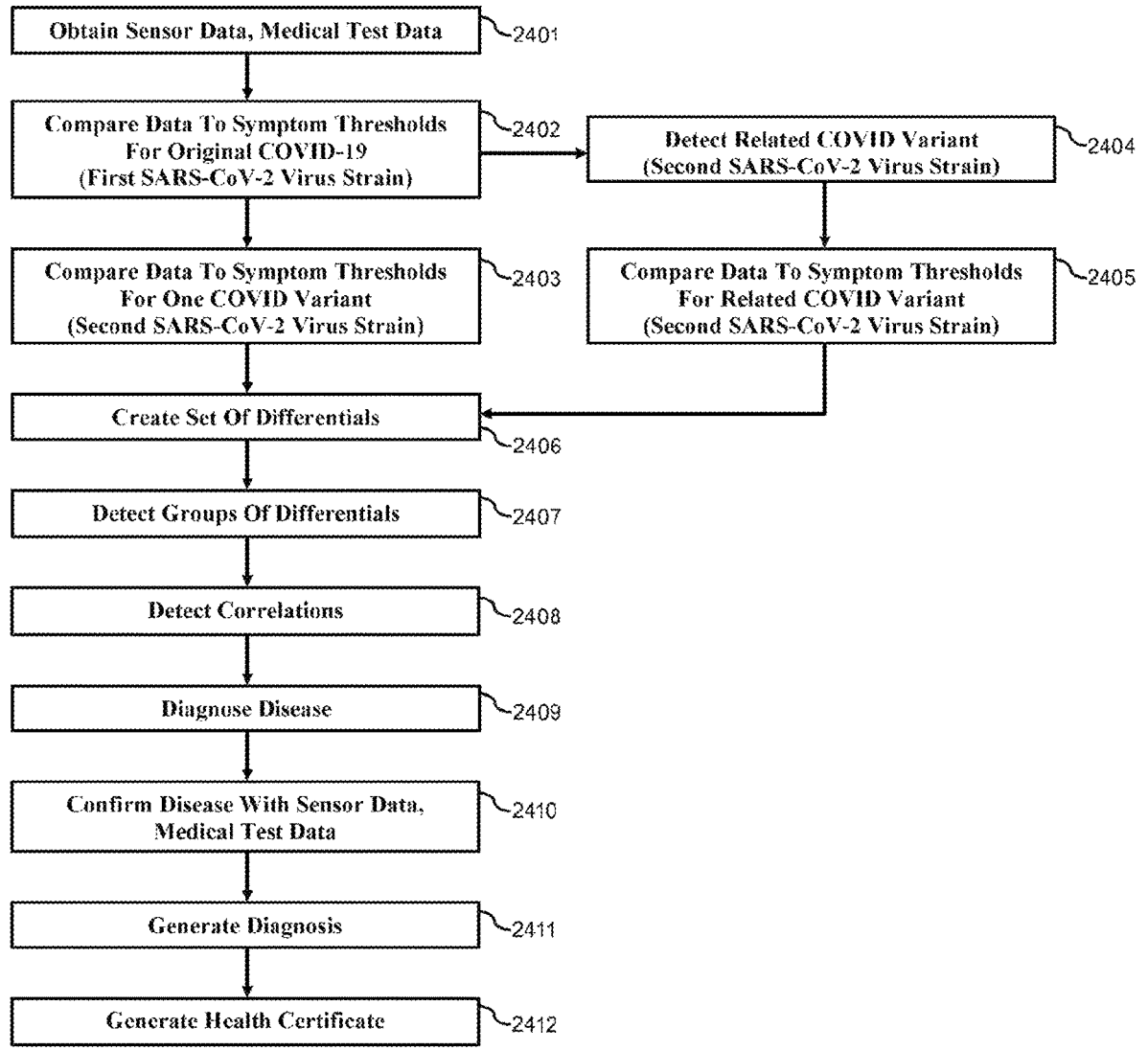
FIG. 24 is a flowchart illustrating the steps of the algorithm according to a first embodiment of the invention.

FIG. 24 is a flowchart illustrating the steps of the algorithm for detecting COVID variants according to a first embodiment of the present invention. The system of the present invention for detecting new COVID variants includes a group of servers (a central server, a medical server, an analytical server, a machine learning server, a certification server), on which operations are performed according to the algorithm, comprising the following steps. At least one patient's biochemical and biophysical data is obtained in step 2401 from the sensors (including biosensors with a mixed biological component) and through the medical tests that can be tests for COVID disease (e.g., antigen test, molecular test, antibody test). The biosensors of the present invention utilizing two different biological components have the first and second biological components (e.g., proteins, lipids, antibodies, enzymes, reagents, polymers, DNA or RNA molecules, microbial cells, cell receptors, a biomolecule dye, etc.) that are separated by a membrane and coupled to a physicochemical detector or amplifier within the biosensor.

The values of the patient's biochemical and biophysical data are compared to predetermined symptom threshold values for the original COVID-19 virus strain (the first SARS-CoV-2 virus strain) in step 2402 to calculate differentials (positive or negative). The values of the patient's biochemical and biophysical data are compared to predetermined symptom threshold values for at least one major COVID variant (the second SARS-CoV-2 virus strain) in step 2403 to calculate differentials (positive or negative). In another embodiment of the present invention, in step 2404, the major COVID variant (the second SARS-CoV-2 virus strain) that is closely related to the patient's disease is detected based on a correspondence of its symptoms to the differentials detected in step 2402 by comparing the values of the patient's biochemical and biophysical data to predetermined symptom threshold values for the original COVID-19 virus strain (the first SARS-CoV-2 virus strain). The values of the patient's biochemical and biophysical data are compared to predetermined symptom threshold values for the closely related major COVID variant (the second SARS-CoV-2 virus strain) in step 2405 to calculate differentials (positive or negative).

In an aspect, the closely related major COVID variant (the second SARS-CoV-2 virus strain) is detected such that its symptoms correspond to a majority of the differential detected in step 2402 by comparing the values of the patient's biochemical and biophysical data to predetermined symptom threshold values for the original COVID-19 virus strain (the first SARS-CoV-2 virus strain). In another aspect, the major COVID variant (the second SARS-CoV-2 virus strain) is detected such that its symptoms correspond to a minority of the differentials detected in step 2402 by comparing the values of the patient's biochemical and biophysical data to predetermined symptom threshold values for the original COVID-19 virus strain (the first SARS-CoV-2 virus strain).

The set of all differentials is created in step 2406. In step 2407, the differentials are combined within the set of differentials into multiple groups based on the differences in the differentials. The differentials not included in the groups are not taken into account in the further analysis of the set of differentials. Based on the multiple groups of differentials, the set of differentials are analyzed in step 2408 to detect correlations (tendencies) indicative of relationships between the groups of the differentials. Based on the detected correlations (tendencies), a patient's viral disease is diagnosed in step 2409 in the event that at least one detected correlation (tendency) indicates that the patient is likely to have contracted the COVID disease. The determining in step 2410 that the patient has the viral disease is based on a confirmation of its symptoms with the values of the patient's biochemical and biophysical data obtained from the sensors and through the medical tests in step 2401. In response to a determination that the patient has or has not contracted the disease, a diagnosis indicating the presence or absence of a disease is generated in step 2411. The diagnosis can be a test result indicating the presence or absence of COVID disease in a patient.

Based on the received diagnosis, in step 2412, the system generates a patient's health certificate, which includes the patient's disease, the test result for the patient that indicates the presence or absence of COVID disease, the viral risk score, the difference between the disease and the original COVID-19 virus, the probability of the patient being infected by a new COVID variant, the major COVID variant that is closely related to the disease, patient's diseases that accompany COVID-19, the disease statistics by criterion (e.g., sex, age, region), the projected post-COVID syndrome for the patient. In an aspect, the patient's health certificate is storied to a database on a computer for further outputting or displaying. In another aspect, the patient's health certificate is transmitted to a mobile electronic device using end-to-end encryption. In yet another aspect, the patient's health certificate is loaded to a Cloud server shared by multiple computers.

Figure 25:
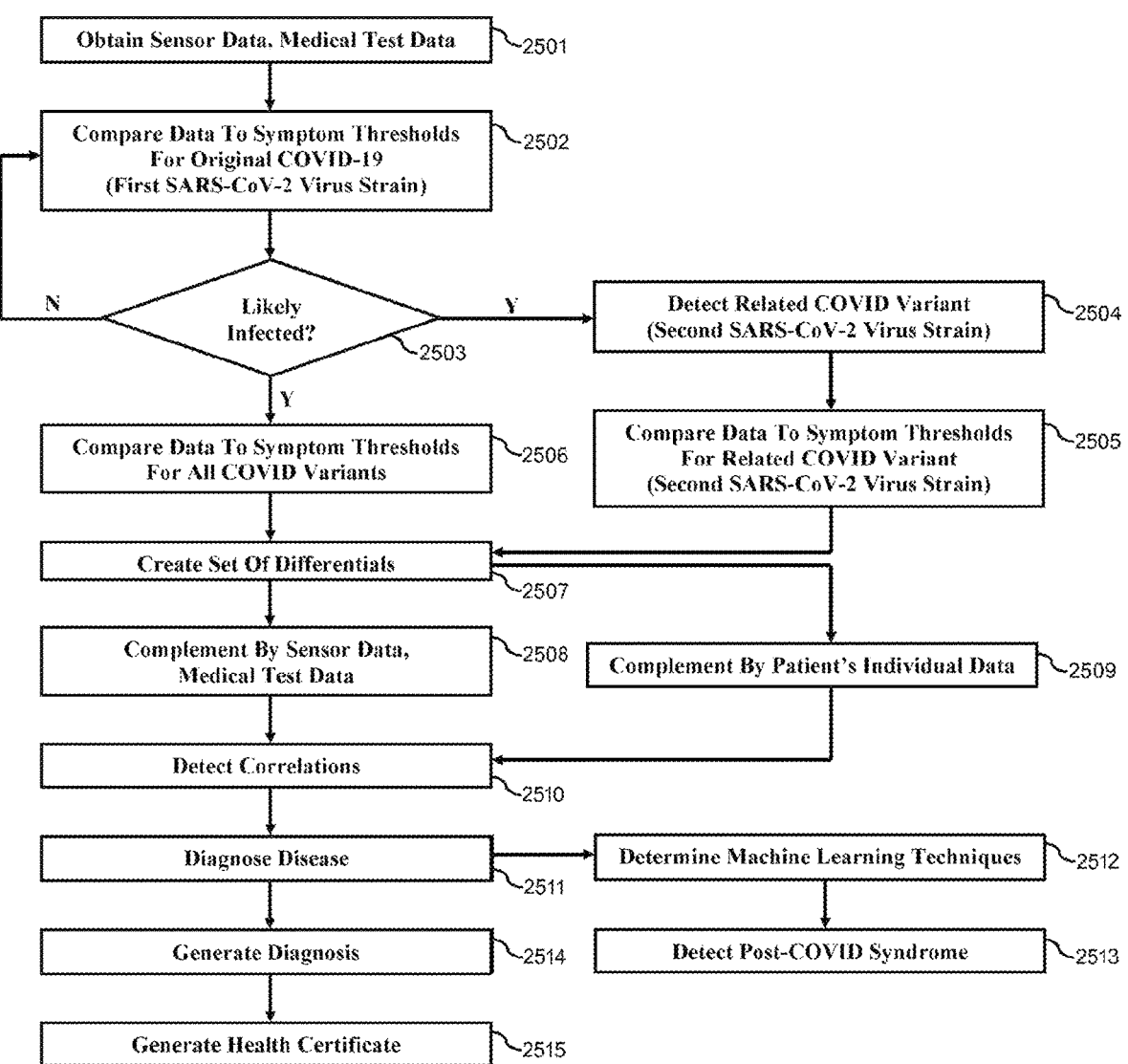
FIG. 25 is a flowchart illustrating the steps of the algorithm according to a second embodiment of the invention.

FIG. 25 is a flowchart illustrating the steps of the algorithm for detecting COVID variants according to a second embodiment of the present invention. The patient's biochemical and biophysical data is obtained from a variety of sensors in step 2501. In another aspect, the medical institution runs laboratory medical tests for COVID disease (e.g., antigen test, molecular test, antibody test), laboratory medical examinations for COVID disease and so obtains biochemical and biophysical data in step 2501. The sensors may include a smartphone, a pulse oximeter, a body temperature thermometer, etc. The sensors also may include biosensors of the present invention utilizing two different biological components with the first and second biological components separated by a membrane within the biosensor. The data is transferred by the sensor using a secure encoded channel. The process may be performed by the server or central processing unit in conjunction with the user device (e.g., running a software program provided by the server or central processing unit). The sensor data may provide direct evidence the user is experiencing one of the symptoms.

Then, the values of the patient's biochemical and biophysical data obtained is compared to predetermined symptom threshold values for the original COVID-19 virus strain (the first SARS-CoV-2 virus strain) in step 2502, e.g., the values of the patient's biochemical and biophysical data obtained through laboratory medical tests are compared to positive and negative predetermined antibody values indices within the sputum or saliva sample used as references for determination viral diseases, particularly, COVID disease. Based on this comparison, the probability of the patient having this viral disease is assessed, and it is concluded whether the patient is infected with COVID disease or not in step 2503. Therefore, the patient's viral disease is identified.

However, the process does not stop here and returns to steps 2501, in which more patient's biochemical and biophysical data is obtained from sensors and through laboratory medical tests, laboratory medical examinations. This updated patient data is again compared with predetermined symptom threshold values in step 2502. Additionally, the set of the patient's individual physiological parameters, such as age, gender, blood type, blood pressure, blood sugar, immunity, vaccination history, etc., is generated. This set may also include diseases that accompany COVID-19, e.g., tuberculosis, diabetes, severe immunosuppression, lymphoma, oncological diseases, ulcers, cardiovascular pathologies, nervous diseases, etc.

Thus, the values of the patient's biochemical and biophysical data obtained from sensors and through laboratory medical tests, laboratory medical examinations are compared to predetermined symptom threshold values for the original COVID-19 virus strain (the first SARS-CoV-2 virus strain) in step 2502. Differences are calculated, and resulting differentials, both positive and negative, are recorded. The differentials are negative when values of the patient's biochemical and biophysical data obtained do not exceed the predetermined symptom threshold values, and positive when values of the patient's biochemical and biophysical data obtained exceed the predetermined symptom threshold values.

If a resulting differential is positive, it means the value of the patient's biochemical and biophysical data exceeds the predetermined symptom threshold value for the original COVID-19 virus strain (the first SARS-CoV-2 virus strain), and the diagnostic follows the algorithm disclosed herein. If a resulting differential is negative, it means the patient's biochemical and biophysical data is below the threshold, and the process returns to step 2501, in which additional data is obtained from using sensors and/or using new laboratory medical tests (and/or laboratory medical examinations), which are run by the medical institution.

In an embodiment of the present invention, in step 2504, the differentials (positive or negative) obtained in step 2502 by comparing the values of the patient's biochemical and biophysical data to predetermined symptom threshold values for the original COVID-19 virus strain (the first SARS-CoV-2 virus strain) are used to identify a major COVID variant (the second SARS-CoV-2 virus strain) that is closely related to the patient's viral disease diagnosed in step 2503. The closely related major COVID variant (the second SARS-CoV-2 virus strain) is detected based on a correspondence of its symptoms to the differentials calculated in step 2502.

In an aspect, the closely related major COVID variant (the second SARS-CoV-2 virus strain) is detected such that its symptoms correspond to a majority of the differential. In another aspect, the closely related major COVID variant (the second SARS-CoV-2 virus strain) is detected such that its symptoms correspond to a minority of the differential. Then, the values of the patient's biochemical and biophysical data is compared to predetermined symptom threshold values for the closely related major COVID variant (the second SARS-CoV-2 virus strain) in order to calculate differentials (positive or negative) in step 2505.

In another embodiment of the present invention, when obtaining differentials in step 2502 by comparing the values of the patient's biochemical and biophysical data to predetermined symptom threshold values for the original COVID-19 virus strain (the first SARS-CoV-2 virus strain), the patient data obtained is additionally compared to predetermined symptom threshold values for all major COVID variants in step 2506 to calculate differentials (positive or negative) for all major COVID variants. All differentials are grouped in step 2507 into the set of differentials (for example, differentials can be combined into the table of differentials for further analysis). In an embodiment of the present invention, in step 2508, this set of differentials is complemented by the set of the patient's biochemical and biophysical data obtained. In another embodiment of the present invention, in step 2509, this set of differentials is complemented by the set of patient's individual physiological parameters, including diseases that accompany COVID-19.

The complemented set of differentials is then analyzed in step 2510 using statistical methods (e.g., the method of combinatorial statistical analysis, the methods of cluster analysis), mathematical methods (e.g., the mathematical method of dense network of curves) to detect correlations (tendencies) within the set. The correlations (tendencies) indicative of relationships between within the values of the complemented set of differentials. Based on the detected correlations (tendencies) in step 2510 that are the mathematical or logical relationships between the values, a viral disease is diagnosed in step 2511, wherein the following processes are involved: diagnosing the patient's viral disease and getting test result indicating the presence or absence of COVID disease, detecting a major COVID variant (the second SARS-CoV-2 virus strain) that is closely related to the patient's viral disease diagnosed (the process returns to steps 2502 and 2504), keeping statistics of the viral disease course depending on the set of differentials (the process returns to steps 2503 and 2507), predicting the disease course based on the set of differentials and patient's individual physiological parameters (the process returns to steps 2507 and 2509), determining individual traits of the course of the patient's diseases that accompany COVID-19 (the process returns to steps 2503 and 2509), predicting the post-COVID syndrome and its idiosyncrasies (the process returns to steps 2509 and 2511).

Based on the resulting diagnosis, machine learning techniques are determined in step 2512 for the set of differentials and the set of patient's individual physiological parameters, including diseases that accompany COVID-19, in order to determine individual traits of the disease course (the process can be return to steps 2503 and 2511). In another embodiment of the present invention, machine learning techniques are used to update and/or adjust predetermined symptom threshold values for all major COVID variants (the process returns to steps 2502 and 2506). In another embodiment of the present invention, machine learning techniques are used to adjust predetermined symptom threshold values for all major COVID variants, considering the patient's individual physiological parameters that include diseases that accompany COVID-19 (the process returns to steps 2506 and 2509).

Using machine learning techniques the post-COVID syndrome that can be expected for the identified major COVID variant, taking into account the patient's individual physiological parameters, including diseases that accompany COVID-19, is predicted in step 2513. For example, the post-COVID syndrome for the Delta variant often involved increased fatigue, long-term nasopharyngeal inflammation, voice changes, impaired memory, cognitive failures (slower reaction, inability to operate properly, etc.), impaired hearing, intestinal disorders, lung and heart lesions, increased susceptibility to other infections.

A system generates a diagnosis in step 2514. The diagnosis is displayed on the smartphone screen in real-time, showing the risk of the patient being infected by a major COVID variant. In step 2515, the diagnosis is represented as a patient's health certificate, in which the patient's viral disease is given. The patient's health certificate comprises the representation of the biometric sample of the patient. The biometric sample is one or more of a thumbprint set recorded from the patient, a retina scan recorded from the patient, and a DNA sample obtained from the patient and analyzed, etc.

The patient's health certificate provides the patient's detected viral disease, the test result for the patient that indicates the presence or absence of COVID disease, the viral risk score, the probability of the patient being infected by a COVID variant, individual differences between the patient's viral disease diagnosed and the original COVID-19 virus strain (the first SARS-CoV-2 virus strain), the major COVID variant (the second SARS-CoV-2 virus strain) that is closely related to the patient's disease, possible individual traits of the patient's disease course based on the patient's individual physiological parameters, general statistics of the course of the patient's disease depending on their sex, age, area of living, etc., the projected post-COVID syndrome.

The certification server can be communicatively coupled to an internal API for transmission of health certificates to electronic medical records and human resources records in medical institutions. External APIs can be communicatively coupled to the certification server to query the health certificates associated with the patient. For external APIs, the system can output the necessary information based on the type of entity requesting the information, for example, to access a specific venue, which is any public place with a large number of people, where permission to enter is required and where the chance of a spread of a viral infection is greater.

The generated patient's health certificate can be tied to the person's ID and used for various digital identifications of the patient. The person's ID number for each respective patient can be electronically tied to their corresponding health certificate, and then the person ID can be used as a unique electronic element or identifier to access with subsequent queries for a health certificate of the patient. The system can output the necessary information based on the type of entity requesting the information, and can output to a requestor an indication the patient has or does not have a viral disease COVID variant. For this, the patient's health certificate includes a code (e.g., a QR code) capable of being scanned to display the health certificate on user interfaces or an electronic device.

In some embodiments of the present invention, step 2509 has an additional step, in which, based on the analysis of the set of differentials and the set of the patient's individual physiological parameters, a major COVID variant (the second SARS-CoV-2 virus strain) is identified, which is closely related to the patient's viral disease that has been diagnosed in step 2503. Then, the process returns to step 2505, in which the biochemical and biophysical data is compared with the predetermined symptom threshold values for the related major COVID variant (the second SARS-CoV-2 virus strain) to calculate differentials. Then, a new set of differentials is generated and analyzed using statistical methods, mathematical methods, machine learning techniques to detect correlations (tendencies) that are the mathematical or logical relationships between the values within the set. Based on the correlations (tendencies), the viral disease is diagnosed again, but with higher precision.

In some embodiments of the present invention, according to the algorithm, databases with patient's biochemical and biophysical data, patient's individual physiological parameters, diseases that accompany COVID-19, additional patient data, predetermined symptom threshold values for the original COVID-19 virus (the first SARS-CoV-2 virus strain), and predetermined symptom threshold values for at least one major COVID variant (the second SARS-CoV-2 virus strain) are generated. Then, these databases are analyzed using statistical methods, mathematical methods, machine learning techniques that are applied on all data saved on the databases. Based on the results of the analysis and detected correlations (tendencies), the viral disease is diagnosed again, but with higher accuracy.

In some embodiments of the present invention, the tests for COVID disease are conducted and results are awaited. According to the algorithm, the system can determine the antibody index within the sputum or saliva sample for the patient in step 2501, the system can determine any prior conditions associated with the patient in step 2503, then again the system can determine an antibody index within the sputum or saliva sample for the patient in step 2501, and the system determines the patient's individual physiological parameters in step 2509. The data can include manual testing and/or automated testing results, both in real-time and previously performed tests.

Steps 2502 and 2506 can incorporate medical guidelines associated with predetermined symptom threshold values for all major COVID variants to determine whether the antibody index within the sputum or saliva sample, respectively, are at levels below or above the predetermined symptom threshold value. If tested positive, differentials are automatically determined for all major COVID variants. Also, again the same procedure is followed for the patient's individual physiological parameters. Whenever a patient tests positive, the system will list the data of differentials and data of the patient's individual physiological parameters.

The antibody index within the sputum or saliva sample, differentials, and the patient's individual physiological parameters can be used to generate a risk score or level. The risk score or level can be updated in a real-time or substantially real-time manner as additional test data is obtained and/or as medical guidelines are updated. The information is saved in step 2512 on the database and that data is analyzed using machine learning techniques. The reports and graphs from machine learning computers are stored on a cloud server for conclusions and suggestions. While a preferred embodiment has been set forth above, those skilled in the art will readily appreciate that other embodiments can be realized within the flowchart of the algorithm.

Figure 26:
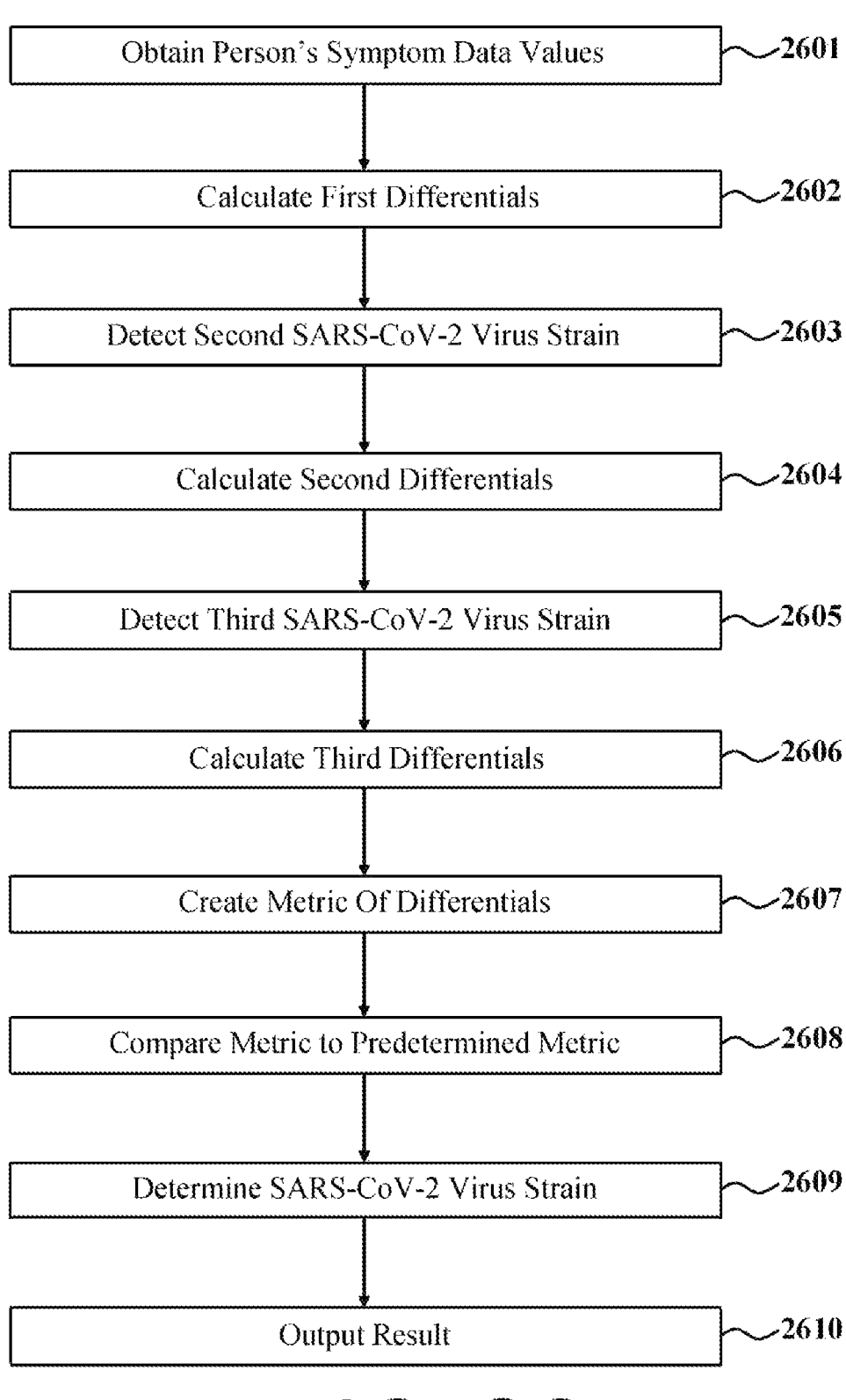
FIG. 26 is a flowchart illustrating the steps of the algorithm according to a third embodiment of the invention.

FIG. 26 is a flowchart illustrating the steps of the algorithm for detecting COVID variants according to a third embodiment of the invention. The symptom data values from at least one person are obtained in step 2601 from the sensors, biosensors of the present invention utilizing two different biological components, and through the medical tests (e.g., antigen test, molecular test, antibody test), medical examinations. The person's symptom data values are compared to predetermined symptom threshold values for the first original SARS-CoV-2 virus strain in step 2602 to calculate first differentials (positive or negative).

In step 2603, the second mutated SARS-CoV-2 virus strain is detected based on a correspondence of its symptoms to the first differentials detected in step 2602 by comparing the person's symptom data values to predetermined symptom threshold values for the first original SARS-CoV-2 virus strain. In an aspect, the second SARS-CoV-2 virus strain is detected such that its symptoms correspond to a majority of the first differentials. In another aspect, the second SARS-CoV-2 virus strain is detected such that its symptoms correspond to a minority of the first differentials. The person's symptom data values are compared to predetermined symptom threshold values for the second SARS-CoV-2 virus strain in step 2604 to calculate second differentials (positive or negative).

In step 2605, the third mutated SARS-CoV-2 virus strain is detected based on a correspondence of its symptoms to the second differentials detected in step 2604 by comparing the person's symptom data values to predetermined symptom threshold values for the second mutated SARS-CoV-2 virus strain. In an aspect, the third SARS-CoV-2 virus strain is detected such that its symptoms correspond to a majority of the second differential. In another aspect, the third SARS-CoV-2 virus strain is detected such that its symptoms correspond to a minority of the second differential. The person's symptom data values are compared to predetermined symptom threshold values for the third SARS-CoV-2 virus strain in step 2606 to calculate third differentials (positive or negative).

The metric of differentials is created in step 2607. The first, second and third differentials within metric of differentials are ordered in their values relative to symptoms of the first SARS-CoV-2 virus strain, symptoms of the second SARS-CoV-2 virus strain and symptoms of the third SARS-CoV-2 virus strain. In step 2608, the metric of differentials are compared to the known predetermined metric that contains known values of differentials indicating that the person has contracted the first SARS-CoV-2 virus strain, the second SARS-CoV-2 virus strain or the third SARS-CoV-2 virus strain.

Based on the comparison, a presence or absence of SARS-CoV-2 virus strain in a person is determined in step 2609. In an aspect, the determination that the person has contracted the SARS-CoV-2 virus strain occurs when at least one value within the metric exceeds the values within the predetermined known metric. In another aspect, the determination that the person has contracted the SARS-CoV-2 virus strain occurs when the majority of the values within the metric exceed the values within the predetermined known metric. In response to a determination that the person has or has not contracted the SARS-CoV-2 virus strain, a result (e.g., a person's health certificate) indicating the presence or absence of COVID disease is output in step 2610.

A computer system is required to implement the present invention. For example, the steps of the algorithm of FIGS. 24-26 of the present invention may be deployed in part or in whole through a machine that executes computer software, program codes, and/or instructions on a processor. The processor may be part of a server, client, network infrastructure, mobile computing platform, stationary computing platform, or other computing platform. A processor may be any kind of computational or processing device capable of executing program instructions, codes, binary instructions, etc.

The processor may be or include a signal processor, digital processor, embedded processor, microprocessor or any variant such as a co-processor (math co-processor, graphic co-processor, communication co-processor, etc.) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code.

The processor may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache, etc. A processor may include one or more cores that may enhance speed and performance of a multiprocessor. In embodiments, the process may be a dual core processor, quad core processors, other chip-level multiprocessor and the like that combine two or more independent cores (called a die).

The steps of the algorithm of FIGS. 24-26 of the present invention may be deployed in part or in whole through a machine that executes computer software on a server, client, firewall, gateway, hub, router, or other such computer and/or networking hardware. The software program may be associated with a server that may include a file server, print server, domain server, internet server, intranet server and other variants such as secondary server, host server, distributed server, etc. The server may include one or more of memories, processors, computer readable media, storage media, ports (physical and virtual), communication devices, and interfaces capable of accessing other servers, clients, machines, and devices through a wired or a wireless medium, etc. The methods, programs or codes as described herein and elsewhere may be executed by the server. In addition, other devices required for execution of the steps of the algorithm of FIGS. 24-26 of the present invention may be considered as a part of the infrastructure associated with the server.

The server may provide an interface to other devices including, without limitation, clients, other servers, printers, database servers, print servers, file servers, communication servers, distributed servers, etc. Additionally, this coupling and/or connection may facilitate remote execution of program across the network. The networking of some or all of these devices may facilitate parallel processing of a program or method at one or more location without deviating from the scope of the invention. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client, etc. The client may include one or more of memories, processors, computer readable media, storage media, ports (physical and virtual), communication devices, and interfaces capable of accessing other clients, servers, machines, and devices through a wired or a wireless medium, etc. The methods, programs or codes as described herein and elsewhere may be executed by the client. In addition, other devices required for execution of the steps of the algorithm of FIGS. 24-26 of the present invention may be considered as a part of the infrastructure associated with the client.

The client may provide an interface to other devices including, without limitation, servers, other clients, printers, database servers, print servers, file servers, communication servers, distributed servers, etc. Additionally, this coupling and/or connection may facilitate remote execution of program across the network. The networking of some or all of these devices may facilitate parallel processing of a program or method at one or more location without deviating from the scope of the invention. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The steps of the algorithm of FIGS. 24-26 of the present invention may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM, etc. The processes, methods, program codes, instructions described herein and elsewhere may be executed by one or more of the network infrastructural elements.

The methods, programs codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players, etc. These devices may include, apart from other components, a storage medium such as a flash memory, buffer, RAM, ROM and one or more computing devices. The computing devices associated with mobile devices may be enabled to execute program codes, methods, and instructions stored thereon.

Alternatively, the mobile devices may be configured to execute instructions in collaboration with other devices. The mobile devices may communicate with base stations interfaced with servers and configured to execute program codes. The mobile devices may communicate on a peer to peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g., USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, etc.

According to software or hardware engineering practices, the steps of the algorithm of FIGS. 24-26 of the present invention may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present invention. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers, etc.

Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the algorithm of FIGS. 24-26 of the present invention. All such variations and modifications are intended to fall within the scope of this invention. As such, the depiction and/or description of an order for various steps should not be understood to require a particular order of execution for those steps, unless required by a particular application, or explicitly stated or otherwise clear from the context.

The steps of the algorithm of FIGS. 24-26 of the present invention may be realized in hardware, software or any combination of hardware and software suitable for a particular application. The hardware may include a general purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, the steps of the algorithm of FIGS. 24-26 of the present invention may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present invention.

Figure 27:
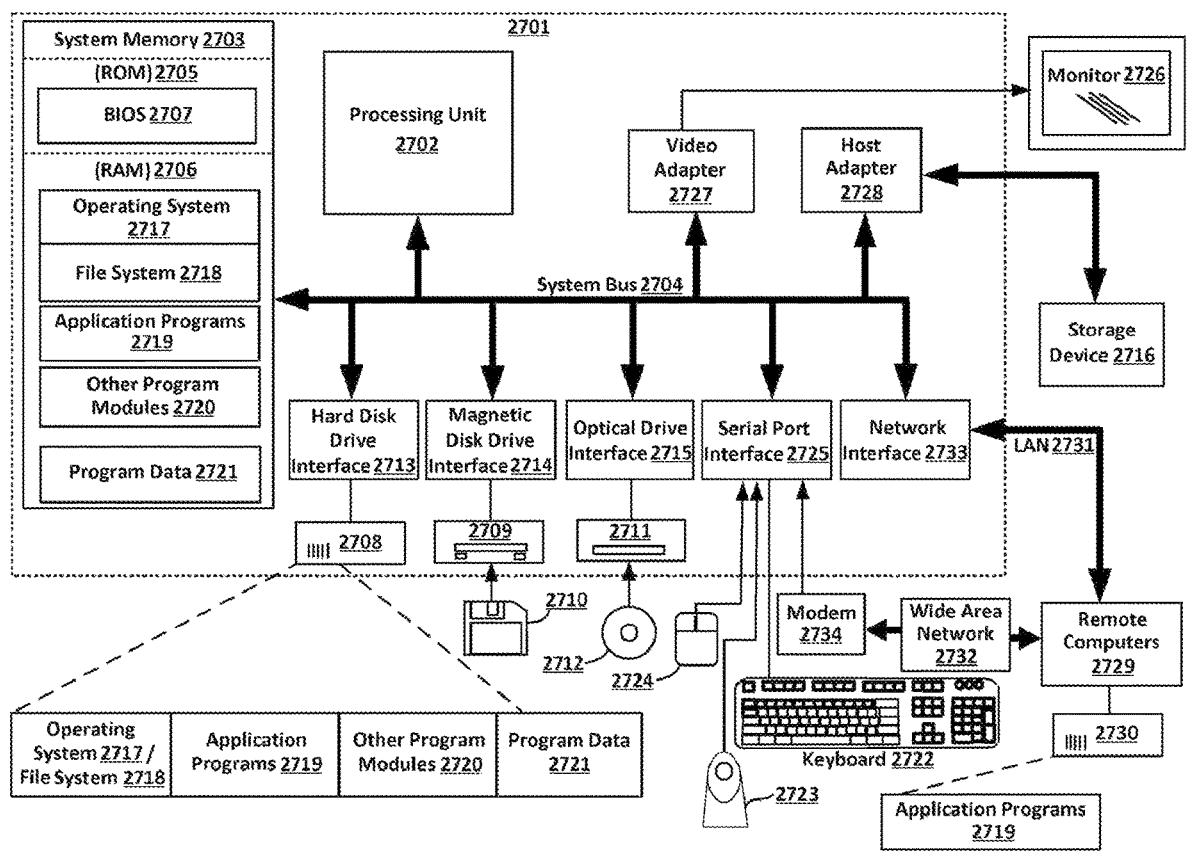
FIG. 27 is a diagram illustrating an example of the computer system for implementing the invention.

FIG. 27 is a diagram illustrating an example of the computer system for implementing the present invention. The computer system includes a general purpose computing device in the form of a host computer or a server, on which the steps of the algorithm of FIGS. 24-26 of the present invention are performed. To execute the algorithm, a host computer or a server 2701 includes a central processing unit (CPU) 2702, a system memory 2703, and a system bus 2704 that couples various system components including the system memory to the central processing unit 2702. The system bus 2704 may be any of several types of bus structures including a memory bus or memory controller, a peripheral bus, and a local bus using any of a variety of bus architectures. The system memory includes a read-only memory (ROM) 2705 and random access memory (RAM) 2706. A basic input/output system 2707 (BIOS), containing the basic routines that help to transfer information between the elements within the computer 2701, such as during start-up, is stored in ROM 2705.

The computer or server 2701 may further include a hard disk drive 2708 for reading from and writing to a hard disk, not shown herein, a magnetic disk drive 2709 for reading from or writing to a removable magnetic disk 2710, and an optical disk drive 2711 for reading from or writing to a removable optical disk 2712 such as a CD-ROM, DVD-ROM or other optical media. The hard disk drive 2708, magnetic disk drive 2709, and optical disk drive 2711 are connected to the system bus 2704 by a hard disk drive interface 2713, a magnetic disk drive interface 2714, and an optical drive interface 2715, respectively.

The drives and their associated computer-readable media provide non-volatile storage of computer readable instructions, data structures, program modules, and other data for the server 2701. Although the exemplary environment described herein employs a hard disk (storage device 2716), a removable magnetic disk 2710, and a removable optical disk 2712, it should be appreciated by those skilled in the art that other types of computer readable media that can store data that is accessible by a computer, such as magnetic cassettes, flash memory cards, digital video disks, Bernoulli cartridges, random access memories (RAMs), read-only memories (ROMs) and the like may also be used in the exemplary operating environment.

A number of program modules may be stored on the hard disk (storage device 2716), magnetic disk 2710, optical disk 2712, ROM 2705, or RAM 2706, including an operating system 2717 (e.g., MICROSOFT WINDOWS, LINUX, APPLE OS X or similar). The server/computer 2701 includes a file system 2718 associated with or included within the operating system 2717, such as the Windows NT™ File System (NTFS) or similar, one or more application programs 2719, other program modules 2720, and program data 2721. A user may enter commands and information into the server 2701 through input devices such as a keyboard 2722, a webcam 2723, and pointing device (e.g., a mouse) 2724. Other input devices (not shown) may include a microphone, joystick, game pad, satellite dish, scanner or the like.

These and other input devices are often connected to the central processing unit 2702 through a serial port interface 2725 that is coupled to the system bus, and they may also be connected by other interfaces, such as a parallel port, game port, or universal serial bus (USB). A monitor 2726 or other type of display device is also connected to the system bus 2704 via an interface, such as a video adapter 2727. In addition to the monitor 2726, computers typically include other peripheral output devices (not shown), such as speakers and printers. A host adapter 2728 is used to connect to the storage device 2716.

The server/computer 2701 may operate in a networked environment using logical connections to one or more remote computers 2729. The remote computer (or computers) 2729 may be another personal computer, a server, a router, a network PC, a peer device, or other common network node, and it typically includes some or all of the elements described above relative to the server 2701, although here only a memory storage device 2730 with application software 2719 is illustrated. The logical connections include a local area network (LAN) 2731 and a wide area network (WAN) 2732. Such networking environments are common in offices, enterprise-wide computer networks, Intranets, and the Internet.

In a LAN environment, the server/computer 2701 is connected to the local area network 2731 through a network interface or adapter 2733. When used in a WAN networking environment, the server 2701 typically includes a modem 2734 or other means for establishing communications over the wide area network 2732, such as the Internet. The modem 2734, which may be internal or external, is connected to the system bus 2704 via the serial port interface 2725. In a networked environment, the program modules depicted relative to the computer or server 2701, or portions thereof, may be stored in the remote memory storage device. It will be appreciated that the network connections shown are merely exemplary and other means of establishing a communications link between the computers may be used.

Figure 28:
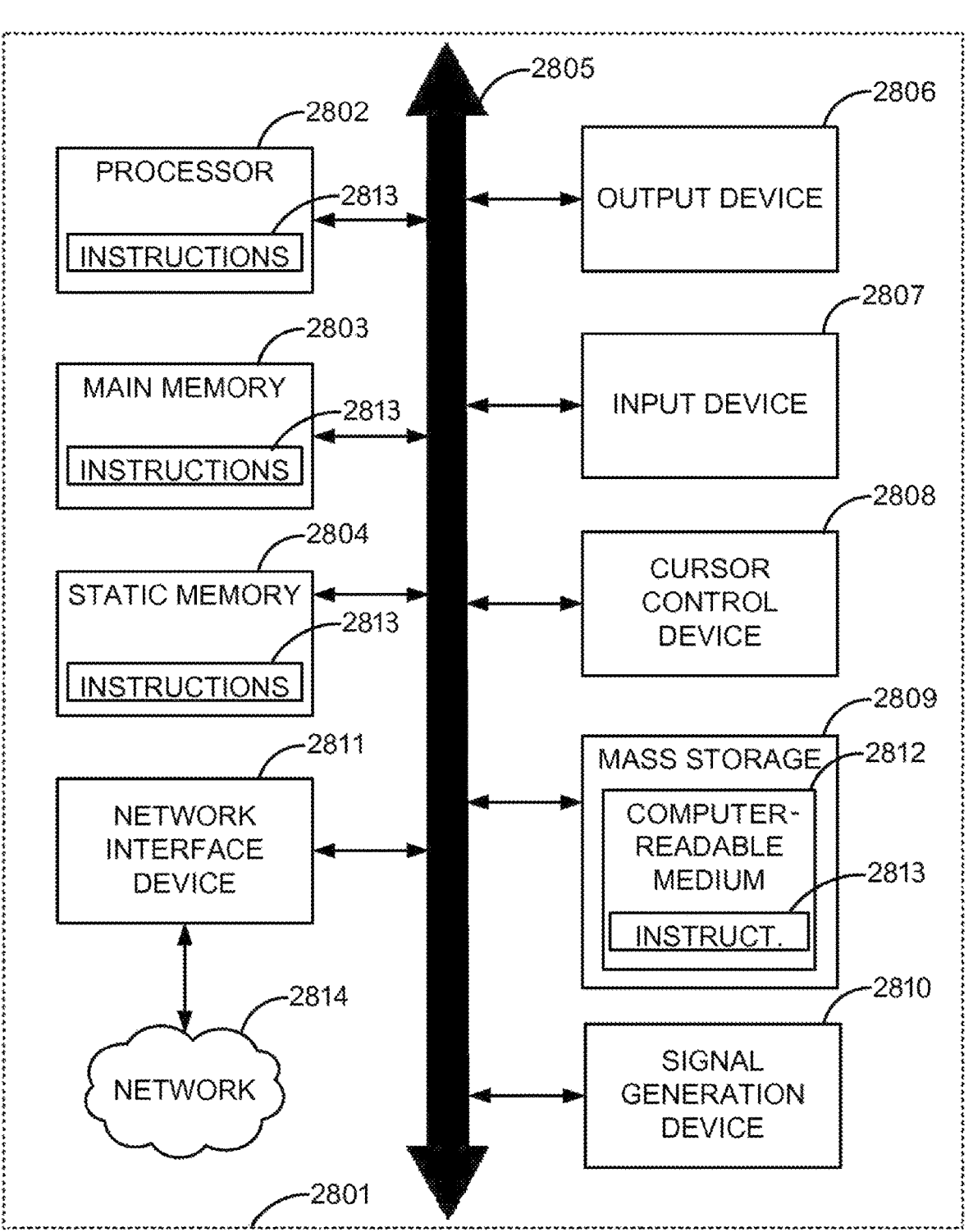
FIG. 28 is a diagram illustrating another example of the computer system for implementing the invention.

FIG. 28 is a diagram illustrating another example of the computer system for implementing the present invention. For example, an article of manufacture, such as a computer 2801, a memory system, a magnetic or optical disk, some other storage device, or any type of electronic device or system can include one or more processors 2802 coupled to a non-transitory computer-readable medium 2812 such as a memory (e.g., removable storage media, as well as any memory including an electrical, optical, or electromagnetic conductor) having instructions 2813 stored thereon (e.g., computer program instructions), which when executed by the one or more processors 2802 result in performing the steps of the algorithm of FIGS. 24-26 of the present invention.

The computer 2801 can take the form of a computer system having a processor 2802 coupled to a number of components directly, and/or using a bus 2805. Such components can include main memory 2803, static or non-volatile memory 2804, and mass storage 2809. Other components coupled to the processor 2802 can include an output device 2806, such as a video display, an input device 2807, such as a keyboard, a cursor control device 2808, such as a mouse, and a signal generation device 2810 (e.g., a speaker or a light emitting diode (LED)). A network interface device 2811 to couple the processor 2802 and other components to a network 2814 can also be coupled to the bus 2805.

The instructions 2813 can further be transmitted or received over the network 2814 via the network interface device utilizing any one of a number of well-known transfer protocols (e.g., HTTP). While the non-transitory computer-readable medium 2812 is shown as a single medium, the term "computer-readable medium" should be taken to include a single medium or multiple media (e.g., a centralized or distributed database, or associated caches and servers, and or a variety of storage media, such as the processor 2802 registers, memories 2803 and 2804, and the storage device 2809) that store the one or more sets of instructions 2813.

Any of these elements coupled to the bus 2805 can be absent, present singly, or present in plural numbers, depending on the specific embodiment to be realized. In an example, one or more of the processor 2802, the memories 2803 and 2804 storage device 2809 can each include instructions 2813 that, when executed, can cause the computer 2801 to the steps of the algorithm of FIGS. 24-26 of the present invention. In alternative embodiments, the computer 2801 operates as a standalone device or can be connected (e.g., networked) to other machines. In a networked environment, the computer 2801 can operate in the capacity of a server or a client machine in server-client network environment, or as a peer machine in a peer-to-peer (or distributed) network environment. The computer 2801 can include a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine 2801 of the machines that individually or jointly execute a set (or multiple sets) of instructions to perform the steps of the algorithm of FIGS. 24-26 of the present invention.

Figure 29:
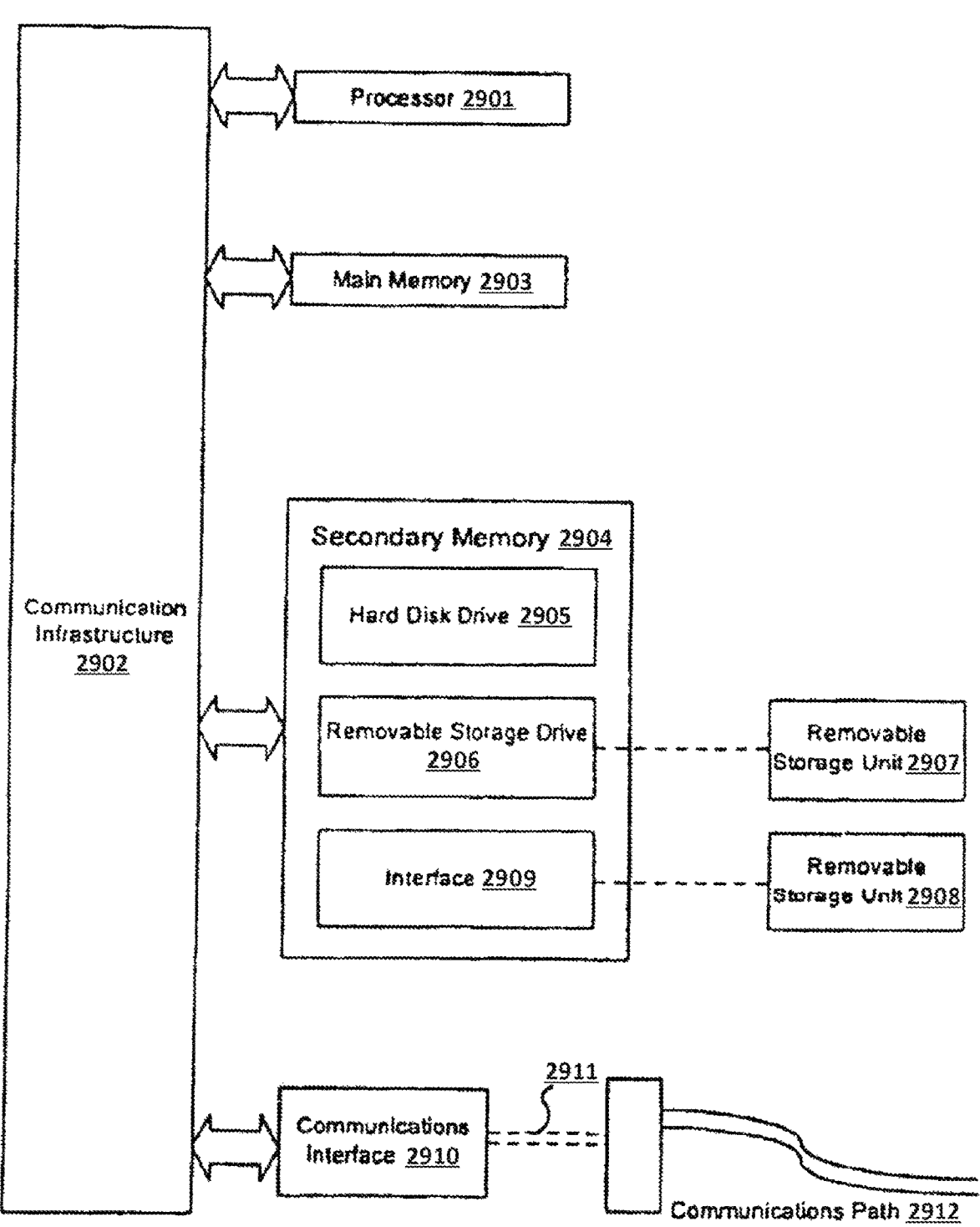
FIG. 29 is a diagram illustrating yet another example of the computer system for implementing the invention.

FIG. 29 is a diagram illustrating yet another example of the computer system for implementing the present invention. The steps of the algorithm of FIGS. 24-26 of the present invention can be implemented as software, in hardware, or as a combination of software and hardware. Consequently, the disclosed system may be implemented in the environment of a computer system or other processing system. Embodiments of the present invention may be implemented in hardware, firmware, software, or any combination thereof. Embodiments of the present invention may also be implemented as instructions stored on a machine-readable medium, which may be read and executed by one or more processors.

A machine-readable medium may include any mechanism for storing or transmitting information in a form readable by a machine (e.g. a computing device). For example, a machine-readable medium may include read only memory (ROM); random access memory (RAM); hardware memory in PDAs, mobile telephones, and other portable devices; magnetic disk storage media; optical storage media; flash memory devices; electrical, optical, acoustical, or other forms of propagated signals (e.g., carrier waves, infrared signals, digital signals, analog signals, etc.), and others. Further, firmware, software, routines, instructions, may be described herein as performing certain actions. However, it should be appreciated that such descriptions are merely for convenience and that such actions in fact result from computing devices, processors, controllers or other devices executing the firmware, software, routines, instructions, etc.

An example of such a computer system for implementing the present invention includes one or more processors, such as a processor 2901. The processor 2901 can be a special purpose or a general purpose digital signal processor. The processor 2901 is connected to a communication infrastructure 2902 (for example, a bus or network). Various software implementations are described in terms of this exemplary computer system. After reading this description, it will become apparent to a person skilled in the relevant art how to implement the disclosed systems and methods using other computer systems and/or computer architectures.

The computer system also includes a main memory 2903, preferably random access memory (RAM), and may also include a secondary memory 2904. The secondary memory 2904 may include, for example, a hard disk drive 2905 and/or a removable storage drive 2906, representing a floppy disk drive, a magnetic tape drive, an optical disk drive, etc. The removable storage drive 2906 reads from and/or writes to a removable storage unit 2907 in a well known manner. The removable storage unit 2907, represents a floppy disk, magnetic tape, optical disk, etc., which is read by and written to by the removable storage drive 2906. As will be appreciated, the removable storage unit 2907 includes a computer usable storage medium having stored therein computer software and/or data.

In alternative implementations, the secondary memory 2904 may include other similar means for allowing computer programs or other instructions to be loaded into the computer system. Such means may include, for example, a removable storage unit 2908 and an interface 2909. Examples of such means may include a program cartridge and cartridge interface (such as that found in video game devices), a removable memory chip (such as an EPROM, or PROM) and associated socket, and other removable storage units 2908 and interfaces 2909 which allow software and data to be transferred from the removable storage unit 2908 to the computer system.

Computer system may also include a communications interface 2910. Communications interface 2910 allows software and data to be transferred between the computer system and external devices. Examples of communications interface 2910 may include a modem, a network interface (such as an Ethernet card), a communications port, a PCM-CIA slot and card, or other communications path interface devices. Software and data transferred via the communications interface 2910 are in the form of signals 2911 which may be electronic, electromagnetic, optical or other signals capable of being received by communications interface 2910. These signals 2911 are provided to communications interface 2910 via a communications path 2912. Communications path 2912 carries signals 2911 and may be implemented using wire or cable, fiber optics, a phone line, a cellular phone link, an RF link and other communications channels.

Computer programs (also called computer control logic) are stored in the main memory 2903 and/or the secondary memory 2904. Computer programs may also be received via the communications interface 2910. Such computer programs, when executed, enable the computer system to implement the steps of the algorithm of FIGS. 24-26 of the present invention. In particular, the computer programs, when executed, enable the processor 2901 to implement the processes disclosed herein. Accordingly, such computer programs operate to control computer system. By way of example, in various exemplary embodiments, the processes/methods performed by signal processing blocks of encoders and/or decoders can be performed by computer control logic. Where the disclosed systems and methods are implemented using software, the software may be stored in a computer program product and loaded into the computer system using the removable storage drive 2906, the hard drive 2905 communications interface 2910, or any other known method of transferring digital information into a computer system.

In this document, the terms computer program medium and computer readable medium are used to generally refer to media such as the removable storage drive 2906, a hard disk installed in hard disk drive 2905, and the signals 2911. These computer program products are means for providing software to the computer system. In another embodiment, disclosed features are implemented primarily in hardware using, for example, hardware components such as Application Specific Integrated Circuits (ASICs) and gate arrays. Implementation of a hardware state machine so as to perform the functions described herein will also be apparent to persons skilled in the relevant art(s).

Figure 30:
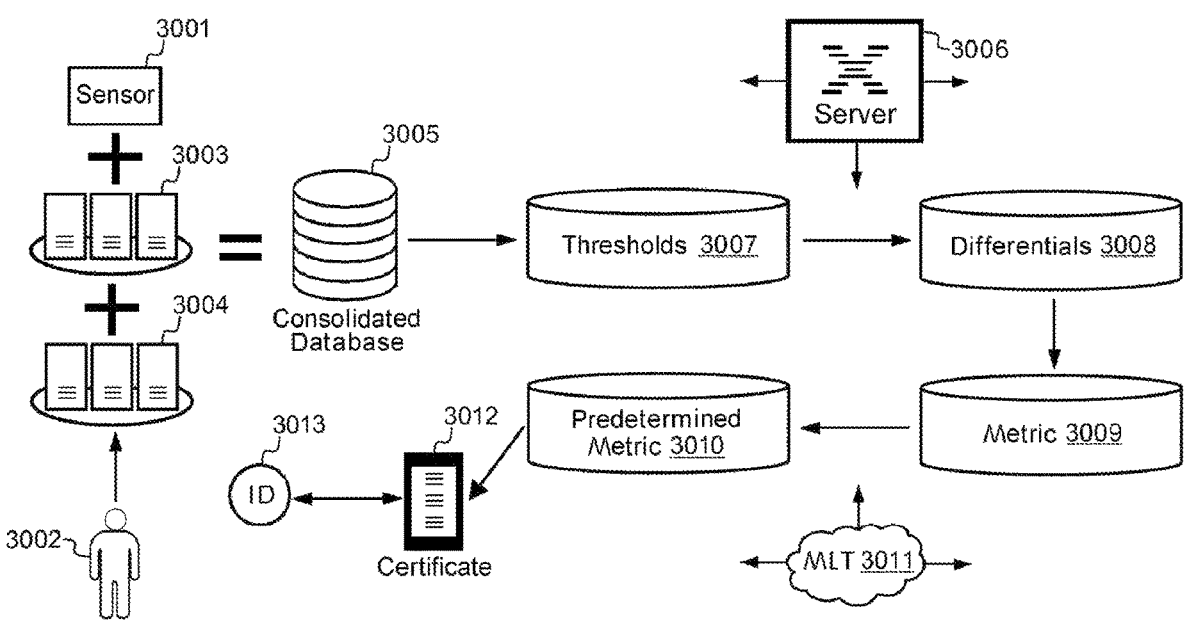
FIG. 30 is a diagram illustrating the system according to a first embodiment of the invention.

FIG. 30 is a diagram illustrating the system for detecting COVID variants according to a first embodiment of the invention. Sensors (including biosensors utilizing two different biological components) 3001 gather biochemical and biophysical data from a person 3002. Also, the biochemical and biophysical data is obtained through laboratory medical tests 3003 and laboratory medical examinations 3004. Laboratory medical tests include tests for COVID disease that can be antigen tests, molecular tests, or antibody tests. All obtained biochemical and biophysical data is combined into a consolidated database 3005 on the server 3006.

Sensors 3001 collect biochemical and biophysical data from a person 3002 representing their symptoms and are either connected to the person 3002 or perform data collection remotely. Sensors 3001 collect the symptom data values from the person for detecting respiratory symptoms (cough, sputum, shortness of breath, fever, anosmia (loss of smell), ageusia (loss of taste), nasal congestion, runny nose, sore throat), musculoskeletal symptoms (muscle pain, joint pain, headache, fatigue), digestive symptoms (abdominal pain, vomiting, diarrhea), physiological diseases (diabetes, lung diseases, cardiovascular diseases, ischemia, hypertension.)

Also, the symptom data values may be obtained at medical institutions that run laboratory medical tests 3003 and laboratory medical examinations 3004. Laboratory medical tests 3003 include the reverse transcription polymerase chain reaction (RT-PCR) test, nucleic acid test, serological test, molecular test CRISPR, isothermal nucleic acid amplification, digital polymerase chain reaction, microarray analysis, next-generation sequencing, antigen tests for antigen proteins, rapid diagnostic test, enzyme-linked immunosorbent assay test, neutralization assay, chemiluminescent immunoassay. Laboratory medical examinations 3004 include chest CT scans, checking for elevated body temperature, checking for low blood oxygen levels, etc.

The sensors 3001 include a smartphone, pulse oximeter, body temperature thermometer, heart pulse sensor, heart monitor, electrodermal activity (EDA) sensor, respiratory sensor, etc. The sensors 3001 include biosensors of the present invention utilizing two different biological components. The biosensors utilizing two different biological components have two different biological components (e.g., proteins, lipids, antibodies, enzymes, reagents, polymers, DNA or RNA molecules, microbial cells, cell receptors, a biomolecule dye) that are separated by a membrane and coupled to a physicochemical detector or amplifier within the biosensor. Types of biosensors of present invention include those that have proteins or aptamers as the first biological component and use whole cell metabolism, ligand debinding and antibody-antigen reaction. The types of person biological information that can be used for collection of the symptom data values can include a nasal swab, nasopharyngeal swab, throat swab, deep airway material, saliva.

The server 3006 is connected to sensors and biosensors 3001 via a data exchange system, collecting symptom data values, which includes antibody level, heartrate, blood pressure, pulse oxygen level, respiratory rhythm/rate, etc., and has a network connection to a person's user device. Sensors and biosensors 3001 may be in communication with a smartphone which, in turn, is in communication with at least one computing device via an Internet connection. The computing devices can be of different types, such as a PC, laptop, tablet, smartphone, smartwatch, etc. The process may be performed by the server 3006 or processor in conjunction with the user device (e.g., running a software program provided by the server or processor). Also the symptom data values 3005 can be collected through, manual input into the system, wireless computer protocols, LIS servers, HL7 diagnostic protocols, HIPAA compliant database queries, batch processing from medical records, any other means of digital entry, etc.

All symptom data values collected from person 3002 using sensors and biosensors 3001, medical tests 3003, examinations 3004 are combined into a consolidated database 3005 on the server 3006. The obtained data values within the consolidated database 3005 may provide direct evidence the person 3002 is experiencing one of the symptoms of COVID disease. The server 3006 may operate in a networked environment using logical connections to one or more remote computers. The remote computer (or computers) may be another personal computer, a server, a router, a network PC, a peer device, or other common network node.

The server 3006 is connected with a central site central processing unit and comprises a database 3005 with the received symptom data values and a database 3007 with the predetermined symptom threshold values for SARS-CoV-2 virus strains: original SARS-CoV-2 virus strain, Alpha (lineage B.1.1.7), B.1.1.7 with E484K, Beta (lineage B.1.351), Gamma (lineage P.1), Delta (lineage B.1.617.2), Lambda (lineage C.37), Mu (lineage B.1.621), Epsilon (lineages B.1.429, B.1.427, CAL.20C), Zeta (lineage P.2), Theta (lineage P.3), Eta (lineage B.1.525), Iota (lineage B.1.526), Kappa (lineage B.1.617.1), Omicron (lineage B.1.1.529), Lineage B.1.1.207, Lineage B.1.1.317, Lineage B.1.616, Lineage B.1.618, Brazilian variant, Centaurus variant, Deltacron variant, etc.

Instructions for detecting COVID variants have been programmed according to the computer implemented algorithm that performed by a central processing unit on the server 3006. The algorithm may be implemented on the computer (or another smart device, such as a smartphone, tablet, or laptop) or other software (Cloud server). When implemented on the smartphone, the algorithm may be a component of the application. When implemented on a computer, the algorithm may be a component of a non-transitory computer-readable medium (removable storage drive, a hard disk installed in a hard disk drive, flash memories, removable discs, non-removable discs, etc.) storing a program of instruction.

The algorithm comprises the steps of: receiving a plurality of symptom data values 3005 (the values of the person's biochemical and biophysical data) from a person 3002, calculating the first differentials 3008 by comparing the received values 3005 to predetermined symptom threshold values 3007 for the first original SARS-CoV-2 virus strain (wherein the first differentials 3008 are negative when the values 3005 do not exceed the first predetermined symptom threshold values 3007, and positive when the values 3005 exceed the first predetermined symptom threshold values 3007), using the first differentials to detect the second mutated SARS-CoV-2 virus strain based on a correspondence of its symptoms to the first differentials, calculating the second differentials 3008 by comparing the received values 3005 to predetermined symptom threshold values 3007 for the second SARS-CoV-2 virus strain (wherein the second differentials 3008 are negative when the values 3005 do not exceed the second predetermined symptom threshold values 3007, and positive when the values 3005 exceed the second predetermined symptom threshold values 3007), creating a metric of differentials 3009 in which the first and second differentials 3008 are ordered in their values relative to symptoms of the first SARS-CoV-2 virus strain and symptoms of the second SARS-CoV-2 virus strain, comparing the metric 3009 to the predetermined know metric 3010 that contains known values of differentials indicating that the person has contracted the first or second strain, determining a presence or absence of SARS-CoV-2 in a person 3002.

In an aspect, the determination that the person 3002 has contracted the SARS-CoV-2 virus strain occurs when at least one value within the metric 3009 exceeds the values within the predetermined known metric 3010. In another aspect, the determination that the person 3002 has contracted the SARS-CoV-2 virus strain occurs when the majority of the values within the metric 3009 exceed the values within the predetermined known metric 3010. In an aspect, the second mutated SARS-CoV-2 virus strain is detected such that its symptoms correspond to a majority of the differentials 3008 detected by comparing the received values 3005 to predetermined symptom threshold values 3007 for the first original SARS-CoV-2 virus strain. In another aspect, the second mutated SARS-CoV-2 virus strain is detected such that its symptoms correspond to a minority of the differentials 3008 detected by comparing the received values 3005 to predetermined symptom threshold values 3007 for the first original SARS-CoV-2 virus strain.

A person skilled in the relevant art will recognize other steps may be applied for implementing the algorithm of the present invention. Thus, an algorithm further comprises the step of detecting the third SARS-CoV-2 virus strain based on a correspondence of its symptoms to the second differentials 3008 calculated by comparing the received values 3005 to predetermined symptom threshold values 3007 for the second SARS-CoV-2 virus strain. Then third differentials 3008 (positive or negative) are calculated between the received values 3005 and the predetermined symptom threshold values 3007 for the third SARS-CoV-2 virus strain for further creating the metric of differentials 3009 in which the first, second and third differentials 3008 are ordered in their values relative to symptoms of the first, second and third strain. In an aspect, the third SARS-CoV-2 virus strain is detected such that its symptoms correspond to a majority of the second differentials 3008 detected by comparing the received values 3005 to predetermined symptom threshold values 3007 for the second SARS-CoV-2 virus strain. In another aspect, the third SARS-CoV-2 virus strain is detected such that its symptoms correspond to a minority of the second differentials 3008 detected by comparing the received values 3005 to predetermined symptom threshold values 3007 for the second SARS-CoV-2 virus strain.

In other aspects, an algorithm further comprises the step of identifying for each of a plurality of the first and second differentials 3008 an accurate value indicative of the likelihood that the person 3002 is experiencing the symptom of the first SARS-CoV-2 virus strain or the symptom of the second SARS-CoV-2 virus strain. Then the differentials 3008 within the metric of differentials 3009 are ordered in their accurate values relative to symptoms of the SARS-CoV-2 virus strains. In other aspects, an algorithm further comprises the step of combining the differentials 3008 into multiple groups based on the differences in the differentials 3008. Then the groups of the differentials within the metric of differentials 3009 are ordered relative to symptoms of the SARS-CoV-2 virus strains.

In other aspects, an algorithm further comprises the step of combining the similar symptoms of the SARS-CoV-2 virus strains into a group. Then the differentials 3008 within the metric of differentials 3009 are ordered relative to multiple groups of symptoms. In other aspects, an algorithm further comprises the step of determining the weighting coefficient for each symptom of the SARS-CoV-2 virus strain that characterizes the severity level of symptom. Then the differentials 3008 within the metric of differentials 3009 are ordered relative to the weighting coefficients. In other aspects, an algorithm further comprises the step of determining the complex symptom that shows the correlation of the several symptoms of the SARS-CoV-2 virus strains. Then the differentials 3008 within the metric of differentials 3009 are ordered relative to complex symptoms.

Databases that contain a set 3005 with the symptom data values (the values of the person's biochemical and biophysical data) obtained from sensors and through medical tests that include tests for COVID disease, a set 3007 with the predetermined symptom threshold values for major SARS-CoV-2 virus strains, a set 3008 with the calculated differentials, a set 3009 with the metric of differentials, a set 3010 with the predetermined known metric of differentials are generated and stored to the server 3006. Then, these databases are analyzed using machine learning techniques 3011 that are applied on the data saved on the databases. In another embodiment of the present invention, these databases are uploaded to the Cloud server that is shared by multiple computers.

In response to a determination that the person 3002 has or has not contracted the SARS-CoV-2 virus strain, a diagnosis indicating the presence or absence of a disease is generated. The diagnosis can be a test result indicating the presence or absence of COVID disease. The person's health certificate 3012 includes a QR code capable of being scanned on a user interface and can be tied to the person ID 3013 and used for various digital identifications of the person 3002. Or the number of the person ID 3013 for each respective person 3002 can be electronically tied to their corresponding person's health certificate 3018. In an aspect, the person's health certificate 3012 is storied to a database on a computer for further outputting or displaying. In another aspect, the person's health certificate 3012 is transmitted to a mobile electronic device using end-to-end encryption. In yet another aspect, the person's health certificate 3012 is loaded to a Cloud server that is shared by multiple computers.

Figure 31:
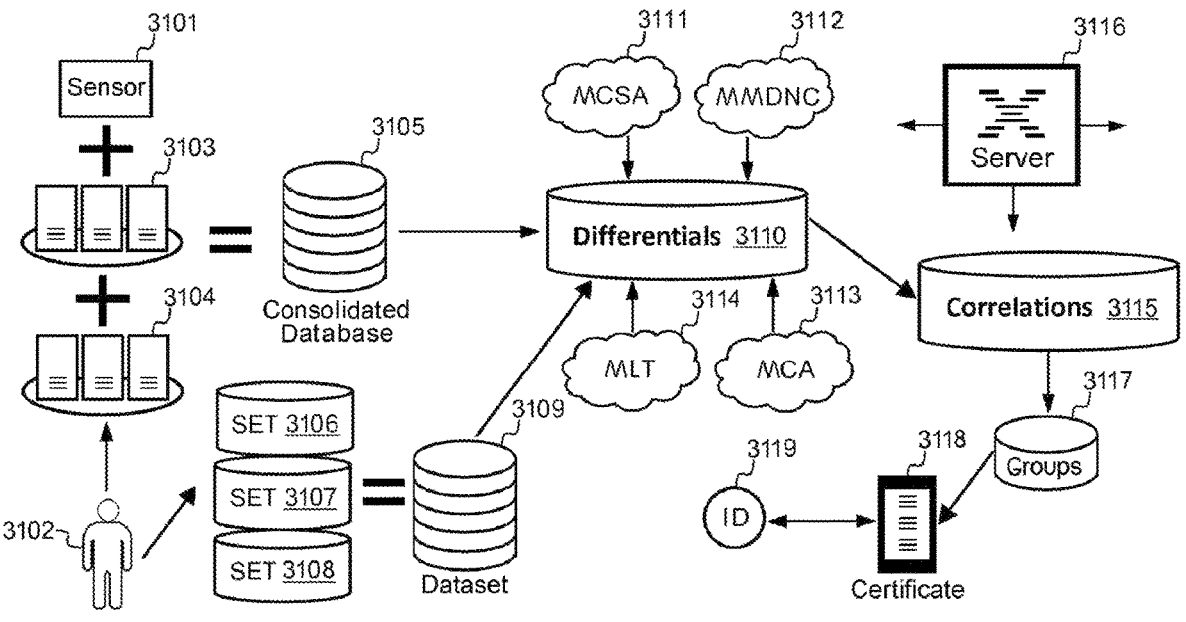
FIG. 31 is a diagram illustrating the system according to a second embodiment of the invention.

FIG. 31 is a diagram illustrating the system for detecting COVID variants according to a second embodiment of the invention. Sensors (including biosensors utilizing two different biological component) 3101 collect biochemical and biophysical data from patients 3102 for detecting symptoms that indicate the presence of a COVID disease. Also, the biochemical and biophysical data is obtained through laboratory medical tests 3103 and laboratory medical examinations 3104. Laboratory medical tests include tests for COVID disease that can be antigen tests, molecular tests, or antibody tests. All obtained biochemical and biophysical data is combined into a consolidated database 3105. The patient's individual data is inputted into the system by the patient 3102 or by a doctor. The patient's individual data includes patient's individual physiological parameters 3106, patient's diseases that accompany COVID-19 3107, additional patient data 3108. All these sets are stored in dataset 3109.

Instructions for calculating differentials have been programmed according to the computer implemented algorithm: comparing the values of the patient's biochemical and biophysical data 3105 to predetermined symptom threshold values for the original COVID-19 virus strain (the first SARS-CoV-2 virus strain) to calculate differentials (positive or negative), using the differentials to detect major COVID variant (the second SARS-CoV-2 virus strain) that is closely related to the patient's disease based on a correspondence of its symptoms to the differentials, comparing the values of the patient's biochemical and biophysical data 3105 to predetermined symptom threshold values for the closely related major COVID variant (the second SARS-CoV-2 virus strain) to calculate differentials (positive or negative). The differentials are negative when the values of the patient's biochemical and biophysical data 3105 do not exceed the predetermined symptom threshold values, and positive when the values of the patient's biochemical and biophysical data 3105 exceed the predetermined symptom threshold values.

In an aspect, the major COVID variant (the second SARS-CoV-2 virus strain) is detected such that its symptoms correspond to a majority of the differential detected by comparing the values of the patient's biochemical and biophysical data 3105 to predetermined symptom threshold values for the original COVID-19 virus strain (the first SARS-CoV-2 virus strain). In another aspect, the major COVID variant (the second SARS-CoV-2 virus strain) is detected such that its symptoms correspond to a minority of the differentials detected by comparing the values of the patient's biochemical and biophysical data 3105 to predetermined symptom threshold values for the original COVID-19 virus strain (the first SARS-CoV-2 virus strain).

In another embodiment of the present invention, instructions further comprises the step of detecting yet another major COVID variant (the third SARS-CoV-2 virus strain) based on a correspondence of its symptoms to the differentials detected by comparing the values of the patient's biochemical and biophysical data 3105 to predetermined symptom threshold values for the closely related major COVID variant (the second SARS-CoV-2 virus strain). Then differentials (positive or negative) are calculated between the values of the patient's biochemical and biophysical data 3105 and the predetermined symptom threshold values for yet another major COVID variant (the third SARS-CoV-2 virus strain).

A set of all differentials 3110 is generated. The set of differentials 3110 is analyzed to detect correlations (tendencies) 3115. To do this, the set of differentials 3110 is complemented by the plurality of the patient's individual data stored in dataset 3109 or by the plurality of the patient's biochemical and biophysical data stored in database 3105. Then the method of combinatorial statistical analysis 3111, the mathematical method of a dense network of curves (method of regression analysis) 3112, the methods of cluster analysis 3113, the machine learning techniques 3114 are used to detect correlations (tendencies). Correlations and tendencies are the mathematical or logical relationships between the values within the set 3110. The resulting plurality of correlations is stored in a database 3115. The algorithm may be implemented on the computer (or another smart device, such as a smartphone, tablet, or laptop) or other software (cloud server). When implemented on the smartphone, the algorithm may be a component of the application. When implemented on a computer, the algorithm may be a component of a non-transitory computer-readable medium (removable storage drive, a hard disk installed in a hard disk drive, flash memories, removable discs, non-removable discs, etc.) storing a program of instruction.

Databases that contain a set of patient's biochemical and biophysical data obtained from sensors and through medical tests that include tests for COVID disease, a set of patient's individual data 3109 (patient's individual physiological parameters 3106, patient's diseases that accompany COVID-19 3107, additional patient data 3108), a set of predetermined symptom threshold values for all major COVID variants, a set of differentials, a set of data about possible post-COVID syndromes are generated. The databases are uploaded and stored to the server 3116. Then, these databases are analyzed using machine learning techniques 3114 that are applied on the data saved on the databases. In another embodiment of the present invention, the databases are uploaded to the cloud server that is shared by multiple computers.

Based on the detected correlations (tendencies) 3115 due to the analysis, a patient's viral disease is diagnosed in the event that at least one correlation (tendency) detected indicates that the patient 3102 is likely to have contracted the COVID disease. In another embodiment of the present invention, the determining that the person has the COVID disease is also based on a confirmation of its symptoms with the values of the patient's biochemical and biophysical data 3105 collected from patients 3102. In another embodiment of the present invention, the detected correlations and tendencies stored in a database 3115 are further analyzed using cluster analysis 3113 to define the same or similar correlations (tendencies) and combining these correlations (tendencies) into a group 3117. The cluster analysis uses the differences in the correlations (tendencies) detected to define multiple groups of correlations (tendencies) 3117 that are same or similar. Based on the multiple groups of correlations (tendencies) 3117 detected, a patient's viral disease is diagnosed in the event that at least one detected group of correlations (tendencies) indicates that the patient 3102 is likely to have contracted the COVID disease.

In response to a determination that the patient 3102 has or has not contracted the disease, a diagnosis indicating the presence or absence of a disease is generated. The diagnosis can be a test result indicating the presence or absence of COVID disease. The system generates diagnosis in the form of a patient's health certificate 3118, which comprises the patient's viral disease as well as all information on the diagnosis, including the test result for COVID disease. The patient's health certificate 3118 includes a QR code capable of being scanned on a user interface and can be tied to the person's ID 3119 and used for various digital identifications of the patient 3102. Or the number of the person's ID 3119 for each respective patient 3102 can be electronically tied to their corresponding patient's health certificate 3118. In an aspect, the patient's health certificate 3118 is storied to a database on a computer for further outputting or displaying. In another aspect, the patient's health certificate 3118 is transmitted to a mobile electronic device using end-to-end encryption. In yet another aspect, the patient's health certificate 3118 is loaded to a Cloud server that is shared by multiple computers.

Figure 32:
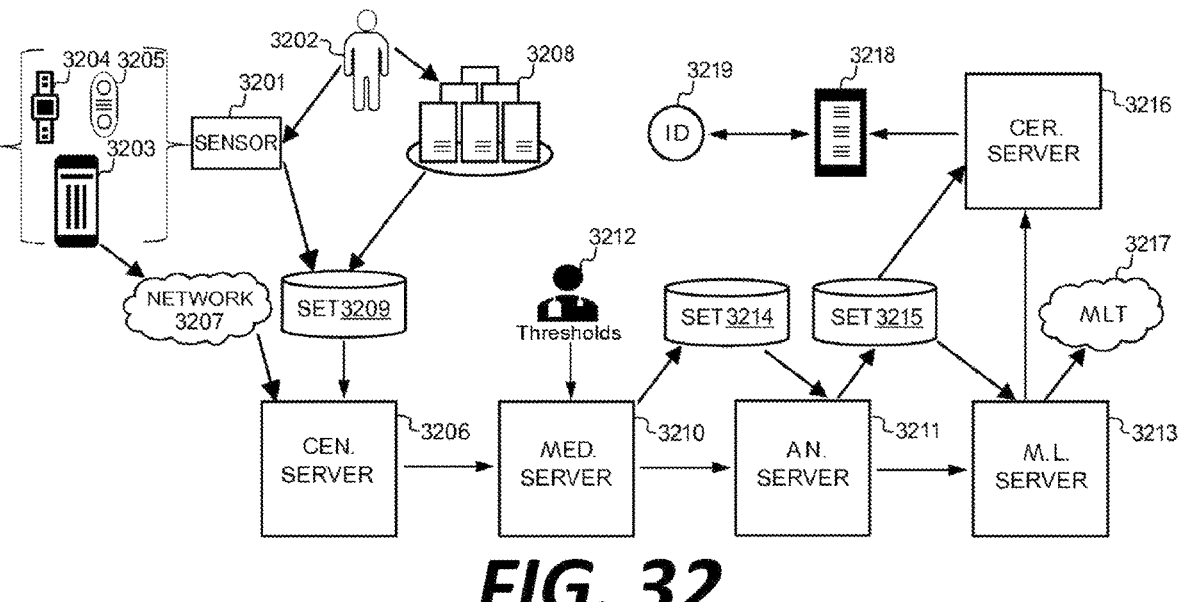
FIG. 32 is a diagram illustrating the system according to a third embodiment of the invention.

FIG. 32 is a diagram illustrating the system for detecting COVID variants according to a third embodiment of the invention. Sensors (including biosensors utilizing two different biological components) 3201 collect biochemical and biophysical data from a person 3202. The sensors 3201 are either connected to the person 3202 or perform data collection remotely, and may include a smartphone 3203, a pulse oximeter 3204, a body temperature thermometer 3205, etc., which send the data collected via a secure and encoded channel to a central server 3206. The system includes using a pulse oximeter 3204 to acquire at least the pulse and blood oxygen saturation percentage, which is transmitted wirelessly to a smartphone. The body temperature thermometer 3205 may be any suitable device configured to sense the body temperature and output information indicative of the body temperature. The body temperature thermometer 3205 may output information indicative of the body temperature to the user device 3203 (e.g., smartphone), for example, via direct, short-range, wireless communication signals (e.g., Bluetooth), via the local area network, etc.

The sensors 3201 include biosensors of the present invention utilizing two different biological components. Also, sensors 3201 may include a heart pulse sensor, a heart monitor, an electrodermal activity (EDA) sensor, a respiratory sensor, electrochemical immunosensor, sensor based on the atomic magnetometer (AM), micro temperature sensor, spectrometer, fluorescence microscope, etc. For example, data indicative of the heart activity of the person may be received, for example, from the heart pulse sensor. Heartrate variability may be determined, for example, based on data received from the heart monitor. Sensors 3201 may be in communication with a smartphone 3203, which, in turn, is in communication with at least one computing device via a wide area network 3207 (WAN), such as the Internet. The computing devices can be of different types, such as a PC, laptop, tablet, smartphone, smartwatch, etc., using one, or different operating systems or platforms.

The central server 3206 is connected to the sensors 3201 via a data exchange system, collecting biochemical and biophysical data, which includes heart rate, blood pressure, pulse oxygen level, respiratory rhythm/rate, etc. The central server 3206 has a network connection to a user device (e.g., a smartphone 3203) and is connected to the wide area network 3207. The system may also be configured to periodically or continuously monitor the health of the person 3202 (e.g., at least once per day.) It should be appreciated that all data may be acquired manually (e.g., by requiring the person 3202 to enter the information), including respiratory rate (e.g., number of breaths per minute), body temperature, and blood pressure (e.g., systolic pressure, diastolic pressure), and used together with other values, such as Perfusion Index (PI %), Perfusion Index Trend Waveform, age, weight, sex, etc., to determine whether the person 3202 is suffering from a SARS-CoV-2 virus strain. The recording of the data is preferably done through the smartphone 3203, or an application operating thereon, using a simple user interface. Alternatively, the process may be performed by the central server 3206 in conjunction with the user device (smartphone) 3203 (e.g., running a software program provided by the central server 3206.)

The biochemical and biophysical data 3208 may be obtained at a medical institution that runs laboratory medical tests for COVID disease (e.g., antigen test, molecular test, antibody test) and laboratory medical examinations for COVID disease. Laboratory medical tests include the reverse transcription polymerase chain reaction (RT-PCR) test, nucleic acid test, serological test, molecular test CRISPR, isothermal nucleic acid amplification, digital polymerase chain reaction, microarray analysis, next-generation sequencing, antigen tests for antigen proteins, rapid diagnostic test, enzyme-linked immunosorbent assay test, neutralization assay, chemiluminescent immunoassay, etc. Laboratory medical examinations include chest CT scans, checking for elevated body temperature, checking for low blood oxygen levels, etc.

A set 3209 comprises decrypted all person's biochemical and biophysical data that has been obtained from sensors 3201 and through laboratory medical tests, laboratory medical examinations 3208. Biochemical and biophysical data stored in set 3209 may be obtained by the person 3202 themselves at home, either manually or automatically. This data may be inputted into the system by the person 3202 themselves, or by a doctor using a smartphone 3203 interface. The person's biochemical and biophysical data 3209 are stored on the central server 3206, which is connected to a medical server 3210 and an analytical server 3211, in datasets that are sent to the medical server 3210 and the analytical server 3211.

Separately, a database with predetermined symptom threshold values 3212 for major SARS-CoV-2 virus strains is generated on the medical server 3210. For this, medical guidelines containing up-to-date medical information for definition of predetermined symptom threshold values 3212 for major SARS-CoV-2 virus strains, or the listing of the predetermined symptom threshold values 3212 for major SARS-CoV-2 virus strains are uploaded to the medical server 3210. By relying on well-established, medically documented, famous scientific facts, predetermined symptom threshold values 3212 that indicate a COVID disease can be established.

The threshold value may be determined, based on the latest medical documentation, such that a value of obtained data below the lowest threshold value is indicative of a low likelihood the person 3202 has contracted a COVID disease. The medical guidelines used to determine predetermined symptom threshold values 3212 for major SARS-CoV-2 virus strains may be updated over time. Therefore, the system for detecting new SARS-CoV-2 virus strains provides a platform that can be updated so the predetermined symptom threshold values 3212 reflect the latest understanding of symptoms for major SARS-CoV-2 virus strains. The database comprising predetermined symptom threshold values 3212 for major SARS-CoV-2 virus strains is sent to a machine learning server 3213 for further action.

The medical server 3210 stores primary instructions for processing data in the database with the person's biochemical and biophysical data 3209 and in the database with predetermined symptom threshold values 3212 for major SARS-CoV-2 virus strains. The primary instructions are executed by the medical server 3210 to induce the system for detecting new SARS-CoV-2 virus strains to perform the following steps in accordance with the algorithm: comparing the values of the person's biochemical and biophysical data 3209 to predetermined symptom threshold values 3212 for the first original SARS-CoV-2 virus strain and finding the first differentials (positive or negative), using the first differentials to detect the second mutated SARS-CoV-2 virus strain based on a correspondence of its symptoms to the first differentials, comparing the values of the person's biochemical and biophysical data 3209 to predetermined symptom threshold values 3212 for the second SARS-CoV-2 virus strain and finding the second differentials (positive or negative).

In an embodiment of the present invention, the second mutated SARS-CoV-2 virus strain is defined such that its symptoms correspond to a majority of differentials detected by comparing the values of the person's biochemical and biophysical data 3209 to predetermined symptom threshold values 3212 for the first original SARS-CoV-2 virus strain. In another embodiment of the present invention, the second mutated SARS-CoV-2 virus strain is defined such that its symptoms correspond to a minority of differentials detected by comparing the values of the person's biochemical and biophysical data 3209 to predetermined symptom threshold values 3212 for the first original SARS-CoV-2 virus strain.

Set 3214 is a set of differentials detected based on the predetermined symptom threshold values 3212 for major SARS-CoV-2 virus strains conforming to medical guidelines that have been obtained by executing the primary instructions. Differentials can be both positive and negative. The differentials are negative when the values of the data 3209 received do not exceed the predetermined symptom threshold values 3212, and positive when the values of the data 3209 received exceed the predetermined symptom threshold values 3212. The set of differentials 3214 is stored in a database and sent to the analytical server 3212 for further analysis, as well as to the machine learning server 3213.

The analytical server 3211 stores the following databases: a database with person's biochemical and biophysical data 3209, a database with predetermined symptom threshold values 3212 for major SARS-CoV-2 virus strains, a database with differentials 3214 that have been determined using the primary instructions. The analytical server 3211 executes secondary instructions stored on the server, applying them to all data in the databases listed above. The secondary instructions induce the system to perform the following operations in accordance with the algorithm: creating a metric of differentials 3215 in which the differentials from the set of differentials 3214 are ordered in their values relative to symptoms of the SARS-CoV-2 virus strains, comparing the metric 3215 to the predetermined known metric that contains known values of differentials indicating that the person has contracted the SARS-CoV-2 virus strain, determining a presence or absence of SARS-CoV-2 in a person.

The created metric of differentials 3215 is stored in a database that is sent to a certification server 3216 for further actions and to the machine learning server 3213 to create machine learning techniques 3217. Also, the metric of differentials 3215 is stored on a non-transitory computer-readable medium (removable storage drive, a hard disk installed in hard disk drive, flash memories, removable discs, non-removable discs, etc.), a Cloud server, a computer, or any other equivalent device. In another embodiment of the present invention, the algorithm further comprises the steps of: creating a metric of differentials 3215, analyzing the metric of differentials 3215 to detect tendencies (correlations) within the metric indicative of relationships between the differentials, determining if the person 3202 has the first SARS-CoV-2 virus strain or the second SARS-CoV-2 virus strain when at least one detected tendency indicates the person 3202 has contracted the first or second virus strain, outputting a result indicating a presence or absence of SARS-CoV-2 in a person.

The machine learning server 3213 stores the following databases: a database with the person's biochemical and biophysical data 3209, a database with predetermined symptom threshold values 3212 for major SARS-CoV-2 virus strains, a database with differentials 3214 that have been calculated using the primary instructions, a database with metric of differentials 3215 that have been calculated using the secondary instructions, a database with predetermined known metric. The machine learning server 3213 applies machine learning techniques 3217 to all data stored in the databases listed above for detecting correlations between the differentials.

Also, machine learning techniques 3217 allow us to set predetermined symptom threshold values 3212 for major SARS-CoV-2 virus strains, and to update and/or adjust predetermined symptom threshold values 3212 for major SARS-CoV-2 virus strains. New predetermined symptom threshold values 3212 are sent to the medical server 3210 to update medical guidelines for major SARS-CoV-2 virus strains. The reports and graphs from machine learning server 3213 are stored on the cloud server and certification server 3216 for conclusions and suggestions, as well as on a non-transitory computer-readable medium.

Based on the comparing the metric 3215 to the predetermined known metric that contains known values of differentials indicating that the person has contracted the SARS-CoV-2 virus strain that have been calculated using the secondary instructions, diagnosis is performed on the certification server 3216 having a network connection with the user device 3203 (e.g., the smartphone), in which a software application is run. Software can be used to make a medical diagnosis based on the received information to determine the likelihood that the person 3202 has contracted the SARS-CoV-2 virus strain. The certification server 3216 analyses data entries, electronically, to find information to determine if the person 3202 has actually been infected by a SARS-CoV-2 virus strain or not and to determine whether there is information confirming infection by a SARS-CoV-2 virus strain. If yes, the certification server 3216 generates a diagnosis providing the projected patient's health condition in real-time.

The diagnosis is displayed on the smartphone 3203 screen, and the system may determine the likelihood that the person 3202 has contracted the SARS-CoV-2 virus strain in response to a request by the person 3202 (e.g., via the user device graphical interface.) The results provided to the person 3202 could be an indication (positive, negative), the likelihood (1-10, low, medium, high), the disease severity (uninfected, mild, moderate, and severe), etc. Also, the diagnosis can be provided as a person's health certificate 3218. The person's health certificate 3218 includes a QR code capable of being scanned to display the person's health certificate 3218 on a graphical interface on the user's electronic device 3203 (e.g., the smartphone). The person's health certificate 3218 comprises the representation of the person's biometric sample, which is one or more thumbprint sets, a retina scan, a DNA sample, etc.

The certification server 3216 can be communicatively coupled to an internal API for transmission of person's health certificates 3218 to electronic medical records and human resources records in medical institutions. External APIs can be communicatively coupled to the certification server 3216 to query the person's health certificates 3218 associated with the person 3202. For external APIs, the system can output the necessary information based on the type of entity requesting the information. For example, the system can output to a requestor via a graphical representation or report on a smartphone 3203 the person's health certificate 3218. The number of the person ID 3219 for each respective person 3202 can be electronically tied to their corresponding person's health certificate 3218. The person ID 3219 can be used as a unique electronic element or identifier to access subsequent queries for the person's health certificate 3218 of the person 3202. While a preferred embodiment has been set forth above, those skilled in the art will readily appreciate that other embodiments can be realized within the represented diagram of the system.

Figure 33:
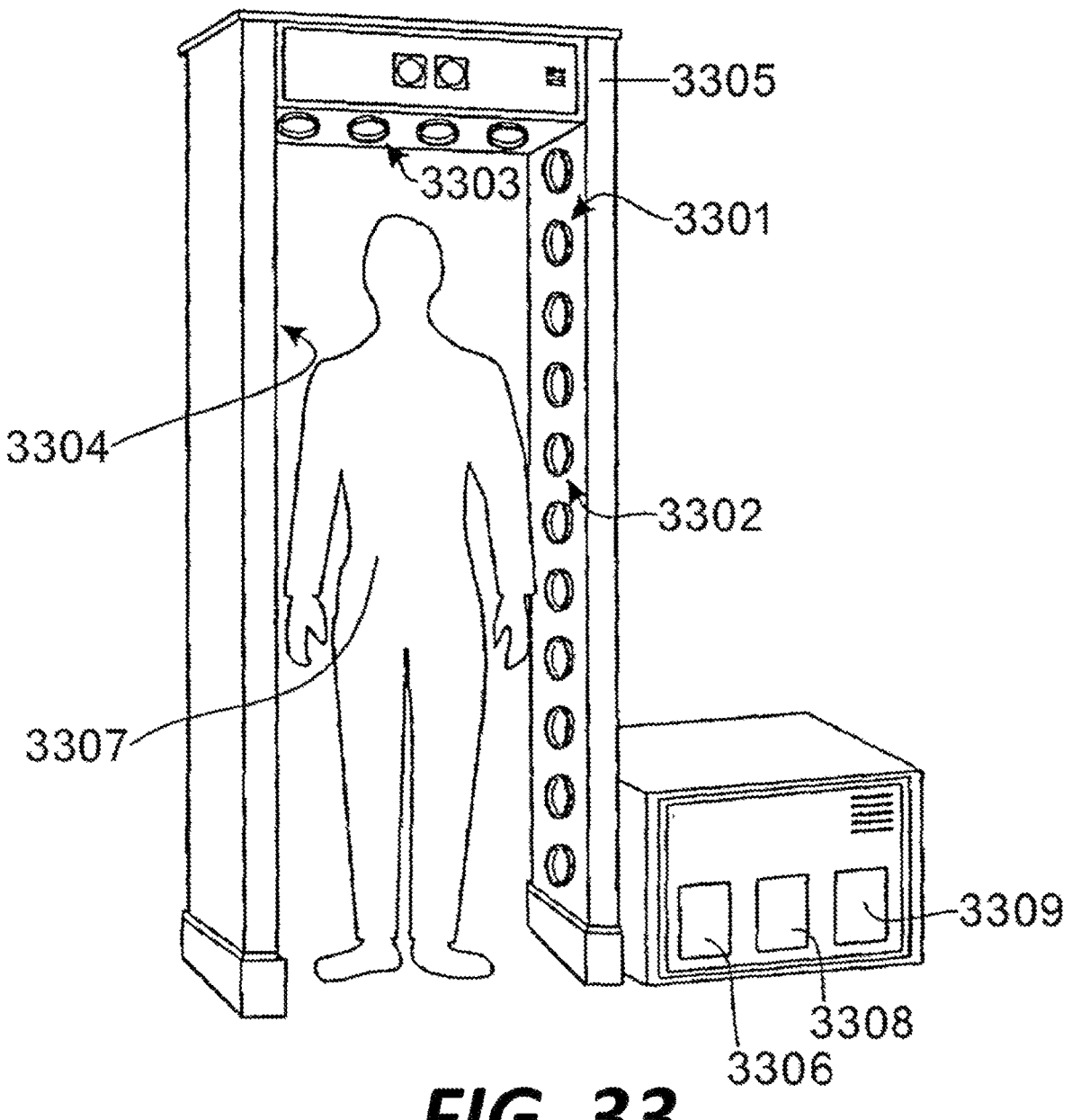
FIG. 33 is a diagram illustrating the system according to a fourth embodiment of the invention.

FIG. 33 is a diagram illustrating the system for detecting COVID variants according to a fourth embodiment of the invention. Multiple collectors 3301, 3302, 3303 and 3304 would be located and mounted on a known walk-through metal detector 3305, such as shown in FIG. 33. Each collector would include an air vacuum or be attached to a central air vacuum box 3306 which would gather and pull in air surrounding the collector. Accordingly, as a person 3307 passed through the walk-through detector 3305, air would be sampled in the immediate vicinity of the individual passing therethrough. By way of example and not by way of limitation, the collectors might be located approximately 25 to 50 cm away from the individual. The particular location would vary depending on the mounting location and depending on the sensitivity of the collector.

Each collector would be connected by a tube or passageway to a sensor 3308 or sensor located nearby. Accordingly, an airborne specimen is obtained. Once the collectors have gathered an airborne specimen or sample, the particulate matter in the specimen will be analyzed by the sensor or biosensors. As the values of the data are obtained, it will be transmitted via a transmitting system central processing unit 3309 to a server 3308 for analysis. A benefit of the present invention is that it could be employed with existing metal detectors in place which would be in close proximity to those passing into and through airports and government buildings. Accordingly, the structure for deploying such a system is already in place.

Instructions for detecting COVID variants have been programmed according to the computer implemented algorithm that performed by a central processing unit on the server 3308. The algorithm comprises the steps of: calculating the first differentials (positive or negative) by comparing the values received by collectors 3301, 3302, 3303 and 3304 to predetermined symptom threshold values for the first original SARS-CoV-2 virus strain, using the first differentials to detect the second mutated SARS-CoV-2 virus strain based on a correspondence of its symptoms to the first differentials, calculating the second differentials (positive or negative) by comparing the values received by collectors 3301, 3302, 3303 and 3304 to predetermined symptom threshold values for the second SARS-CoV-2 virus strain, creating a metric of differentials in which the first and second differentials are ordered in their values relative to symptoms of the first SARS-CoV-2 virus strain and symptoms of the second SARS-CoV-2 virus strain, comparing the metric to the predetermined metric that contains known values of differentials indicating that the person has contracted the first or second strain, determining a presence or absence of SARS-CoV-2 in a person 3307.

In another embodiment of the present invention, the algorithm further comprises the steps of: creating a metric of differentials, analyzing the metric of differentials to detect tendencies (correlations) within the metric indicative of relationships between the differentials, determining if the person 3307 has the first SARS-CoV-2 virus strain or the second SARS-CoV-2 virus strain when at least one detected tendency indicates the person 3307 has contracted the first or second virus strain, outputting a result indicating a presence or absence of SARS-CoV-2 in a person 3307.

Figure 34:
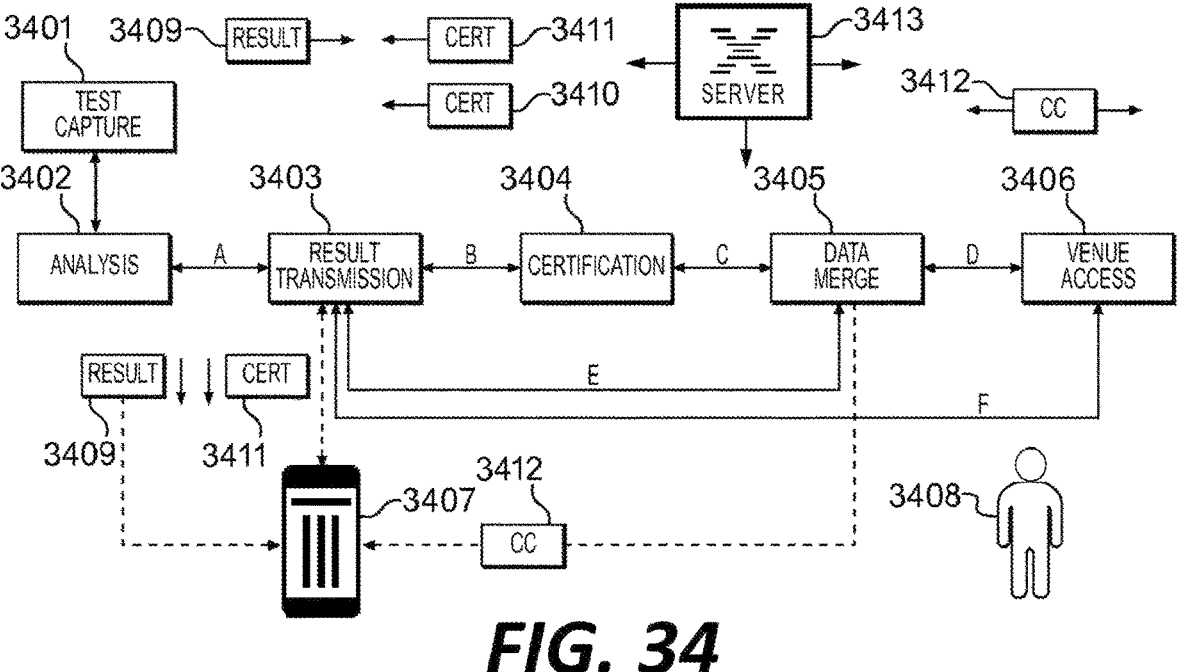
FIG. 34 is a diagram illustrating the system according to a fifth embodiment of the invention.

FIG. 34 is a diagram illustrating the system for detecting COVID variants according to a sixth embodiment of the invention. The system includes a test capture component 3401, an analysis component 3402, a transmission component 3403, a certification component 3404, a data merging component 3405, a venue access component 3406. The components can be implemented by a central processing unit, server, Cloud server, computer, smartphone, or other software. In FIG. 34 the components are uploaded and stored to the server 3413. In another embodiment of the present invention, the components are uploaded to the Cloud server that is shared by multiple computers.

The analysis component 3402 and the transmission component 3403 communicate over interface A to cooperatively allow administration of a medical test of a person that collect sputum and saliva data from sputum and saliva samples from the person, analysis of the sputum and saliva data obtained by medical tests, and generation of a test result by the test capture component 3401 and the analysis components 3402. The analysis component 3402 may supply the results of a medical test to the transmission component 3403 over the interface A. In an aspect, the test capture component 3401, the analysis component 3402, and the transmission component 3403 may be combined in a single hardware device. In another aspect, the test capture component 3401 and the analysis component 3402 may be stand-alone hardware devices. In another aspect, some functions of the transmission component 3403 may be embodied in another component, such as smartphone 3407, or similar device, for example.

The analysis component 3402 performs the actions according to the instructions loaded into the system for: calculating the first differentials (positive or negative) by comparing the values of the sputum and saliva data obtained by medical testing from the test capture component 3401 to predetermined threshold values for the first original SARS-CoV-2 virus strain, using the first differentials to detect the second mutated SARS-CoV-2 virus strain based on a correspondence of its symptoms to the first differentials, calculating the second differentials (positive or negative) by comparing the values of the sputum and saliva data obtained by medical testing from the test capture component 3401 to predetermined threshold values for the second SARS-CoV-2 virus strain, creating a metric of differentials in which the first and second differentials are ordered in their values relative to symptoms of the first SARS-CoV-2 virus strain and symptoms of the second SARS-CoV-2 virus strain, comparing the metric to the predetermined metric that contains known values of differentials indicating that the person has contracted the first or second strain, determining a presence or absence of SARS-CoV-2 in a person.

In another embodiment of the present invention, the algorithm further comprises the steps of: creating a metric of differentials, analyzing the metric of differentials to detect tendencies (correlations) within the metric indicative of relationships between the differentials, determining if the person has the first SARS-CoV-2 virus strain or the second SARS-CoV-2 virus strain when at least one detected tendency indicates the person has contracted the first or second virus strain, outputting a result indicating a presence or absence of SARS-CoV-2 in a person.

In an embodiment of the present invention, the test capture component 3401 and the analysis component 3402 may be implemented at a medical institution, where medical tests that collect the sputum and saliva data are carried out. The medical institution could be located at a specific venue, such as at a pharmacy or at a medical clinic. Alternatively, the medical institution could be located at the entrance to a business center or an airport terminal. The medical institution also may provide some or all the functions of the transmission component 3403. In another embodiment of the present invention, the person 3408 may employ test capture component 3401 to self-perform a medical test for a major SARS-CoV-2 virus strain, such as when at home or other private settings.

The test capture component 3401 includes a medical test kit for testing a user 3408 for possible infection from a new SARS-CoV-2 virus strain. Such a medical test kit may be a small, portable device configured to cooperate with the transmission component 3403. The medical test kit includes different mechanisms to acquire a sample (a nasal swab, nasopharyngeal swab, throat swab, deep airway material, saliva) from the person, analyze the sample, and provide test result for major SARS-CoV-2 virus strain to the transmission component 3403 over the interface A.

The transmission component 3403 may include mechanisms to control operation of the analysis component 3402. For example, when implemented in the smartphone 3407, the transmission component 3403 may include or be in communication with an application of the smartphone 3407, and the application may initiate analysis by the analysis component 3402, may provide data related to the person to the analysis component 3402, and may provide security for the test result 3409 for major SARS-CoV-2 virus strain (e.g., encryption). Following any processing at the transmission component 3403, the test result 3409 for major SARS-CoV-2 virus strain and any associated data may be encrypted and sent to the certification component 3404. The certificate component 3404 receives the secure test result 3409 for major SARS-CoV-2 virus strain over interface B from the transmission component 3403.

In an aspect, the transmission component 3403 and the certification component 3404 may be combined into a single unit or single hardware device. In another aspect, the transmission component 3403 and the certification component 3404 may be co-located such as at a medical institution. In another aspect, the transmission component 3403 and the certification component 3404 are separated and may communicate over a wireless communications network. The transmission mechanism, when the transmission component 3403 and the certification component 3404 are not combined in a single unit, may include any suitable digital data exchange mechanism.

The certificate component 3404 functions to process a secure test result 3409 for major SARS-CoV-2 virus strain and from the test result processing, generate a person's health certificate 3410 attesting to the acceptability of the test result for one or more purposes regarding the COVID viral disease. The person's health certificate 3410 may include the test result for COVID disease as well as all information provided in the secure test result 3409 for major SARS-CoV-2 virus strain. The person's health certificate 3410 may include the date and time of sample collection, the medical test kit identification, including manufacturer and date of manufacture, test type, and a unique serial number of the medical test kit. The person's health certificate 3410 further may include a time to live for the test result 3409 for major SARS-CoV-2 virus strain, such as, for example, 24 hours, one month, etc.

The person's health certificate 3410 also may include a quality value. The quality value may be based on the type of test and the identity of the medical test kit. The quality value further may be based on the process or modality by which the sample is collected and the test result is produced from the sample. The quality value still further may be based on the degree of security, or confidence, in the reliability of the test result. For example, a test sample collected at a medical institution and analyzed at the medical institution may have a high value. Thus a test sample collected by a medical professional at a medical clinic and processed to produce a test result by the medical professional may have the highest value. A test sample collected by person 3408 and applied to a home medical test kit may have a medium value. Other quality factors and quality rating systems may be employed.

The certificate component 3404 may provide the person's health certificate 3410 to the component submitting the secure test result 3409 for the major SARS-CoV-2 virus strain. For example, if the submitting component is the smartphone 3407 of person 3408, the certificate component 3404 may transmit the patient's health certificate 3410 to the smartphone 3407. If the test result submitting component is a medical institution, the certificate component 3404 may provide the person's health certificate 3410 to an address input to the medical institution by the smartphone 3407, for example, an email address of the person 3408. Alternatively, the certificate component 3404 may provide the person's health certificate 3410 for printing at the medical institution. When printed, the person's printed health certificate 3410 may include a tamper-proof RFID (e.g., a read-once RFID). The certificate component 3404 produces a person's health certificate 3411 with a tamper-proof reference. The reference then may be used to look up and retrieve data such as that incorporated in the person's health certificate 3410.

The person 3408 may employ the person's health certificate 3411 in its digital form or in a printed form. For example, the person 3408 may provide the person's health certificate 3411 on the user's smartphone display. In another embodiment of the present invention, the certificate component 3404, or aspects of the certificate component 3404, may be implemented in a cloud-based system. For example, the certificate component 3404 may maintain active as well as deactivated person's health certificate in a cloud storage facility. As noted herein, the transmission component 3403 and the certification component 3404 may be combined on a single hardware device. In an embodiment of the present invention, the certificate component 3404 may be implemented on the computer, smartphone 3407, or another smart device (such as a tablet) operated by the person 3408. In this case, the person's health certificate 3410 is stored on the smartphone 3407, where they remain active until the expiration of the assigned time to live.

When implemented on the smartphone 3407, the certificate component 3404 may be a component of the application. When implemented on a computer, the certificate component 3404 may be a component of a non-transitory computer-readable medium storing a program of instruction. When implemented as a service (e.g., as a cloud-based service) separate from the transmission component 3403, the certificate component 3404 may transmit the person's health certificates 3410 and 3411 to the data merging component 3405 over interface C. Such transmission may require authorization from the person 3408. In another embodiment of the present invention, the person 3408 may operate the smartphone 3407, or other smart device, to transmit the person's health certificates 3410 and 3411 to the data merging component 3405 over interface E.

The data merging component 3405 may produce a certified certificate 3412 that the person 3408 may employ to access a specific venue by using the venue access component 3406. The specific venue is any public place with a large number of people, where a permission to enter is required and where the spread of a viral infection is of great danger, for example, a stadium or an airplane. The data merging component 3405 may produce the certified person's health certificate 3412 by merging data from the venue access component 3406 with a person's health certificate 3410, having acquired the person's health certificate 3410 from the certificate component 3404 or the transmission component 3403. The data merging component 3405 may generate the certified person's health certificate 3412 when requested or authorized to so by the transmission component 3403. The venue access component 3406 may communicate directly with the transmission component 3403 over interface F and/or with the data merging component 3405 over interface D.

The certified person's health certificate 3412 may be produced by the venue access component 3406 based on inputs received from the test result 3409 for major SARS-CoV-2 virus strain, or the transmission component 3403 and/or the data merging component 3405. In an aspect, the transmission component 3403 may provide a person's health certificate 3410 to the venue access component 3406. In another aspect, the transmission component 3403 may provide the venue access component 3406 with authorization and a mechanism to acquire a person's health certificate 3410 from the data merging component 3405. In another aspect, the transmission component 3403 may provide the venue access component 3406 with authorization and a mechanism to acquire a certified person's health certificate 3412 from the data merging component 3405.

Figure 35:
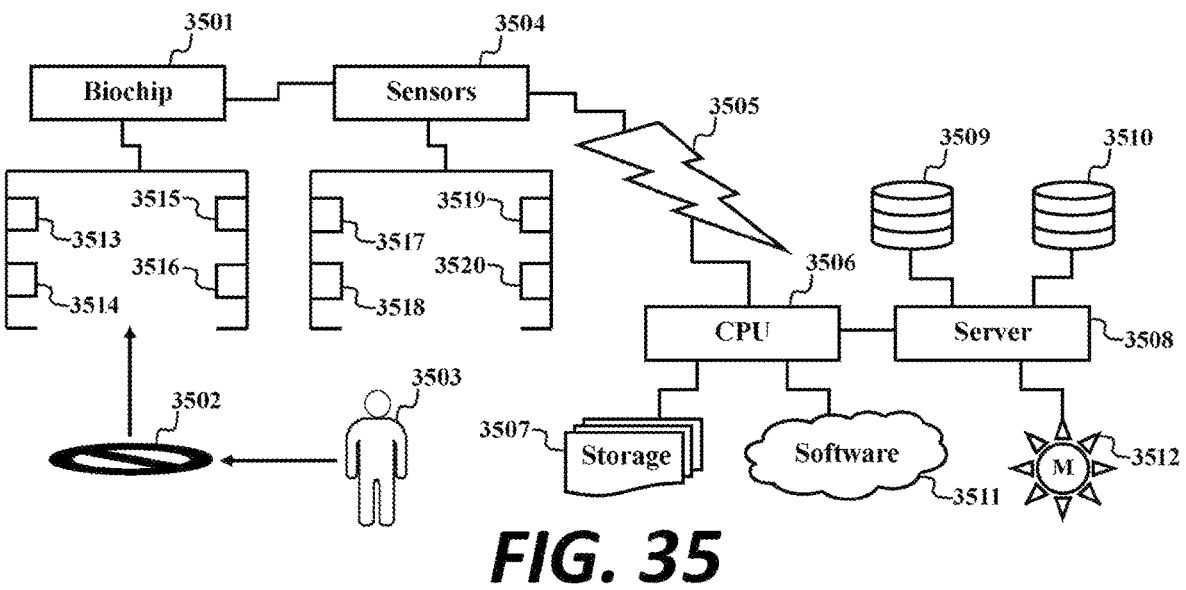
FIG. 35 is a diagram illustrating the system for detecting COVID variants implemented in the device of the "Covidometer."

FIG. 35 is a diagram illustrating the system for detecting COVID variants implemented in the device known as a "Covidometer." The "Covidometer" comprises a collector (e.g., a sensor chip or biochip) 3501 that collects a sputum and saliva samples 3502 from the person 3503, a plurality of sensors and biosensors 3504 (e.g., a sensors panel) that gather data values from the sputum and saliva samples 3502, a transmission system 3505 to transmit data values from the sensors and biosensors 3504, a central processing unit 3506 in communication with the transmission system 3505 to collect data values from the sensors and biosensors 3504, a storage 3507 that receives and stores sputum and saliva samples 3502, a server 3508 in communication with the central processing unit 3506 that comprise a database 3509 with gathered data values and a database 3510 with predetermined symptom threshold values for SARS-CoV-2 virus strains, a software application 3511 that is downloadable to and executable by the central processing unit 3506 to detect tendencies, means (e.g., a display or printer) 3512 for outputting a result indicating a presence or absence of COVID disease in a person 3503.

The collector (e.g., the sensor chip or biochip) 3501 has incorporated thereon a number of biosensors 3513-3516 utilizing two different biological components, which are mounted thereon. The biosensors 3513-3516 interact with a sputum and saliva samples 3502 (e.g., a nasal swab, nasopharyngeal swab, throat swab, deep airway material, saliva) from the person 3503, which will be analyzed by sensors 3517-3520, which are installed on the sensors panel to gather data values from the sputum and saliva samples 3502. In some aspects, the biosensors 3513-3516 work based on the use whole cell metabolism, ligand debinding and antibody-antigen reaction. The biosensors utilizing two different biological components produce electrical, magnetic or optical signals detectable by the sensors 3517-3520 that can be integrated into the memory device of FIG. 6-7.

Once the collector (the sensor chip or biochip) 3501 has gathered a sputum and saliva samples 3502 from the person 3503, the sputum and saliva samples 3502 will be delivered in the storage 3507 that receives and stores collected the sputum and saliva samples from the person. The purpose of the storage 3507 (e.g., the box for biological materials) is to provide for preservation of the sputum and saliva samples 3502 of the person 3503 to enable it to be reanalyzed by the "Covidometer." The analysis of the sputum and saliva samples 3502 will result in sending data values gathered from the sputum and saliva samples 3502 by using the sensors 3517-3520 to a server 3508. The sensors 3517-3520 installed in the sensors panel 3504 of the "Covidometer" are replaceable so that a failure of any sensor could be addressed by a simple replacement of the sensor, allowing simple and robust connection with hardware components of the "Covidometer" by common protocols and procedures following universal standards. In some aspects, the sensors 3517-3520 are embedded in the memory device within the "Covidometer."

The process to collect data values from the sputum and saliva samples 3502 stored in the storage 3507 by using the sensors 3517-3520 may follow a process having a number of steps. At the initial stage data values will be retrieved from the sputum and saliva samples 3502 of person 3503. At the next stage the symptom data values representing the COVID symptoms of person 3503 will be determined from the data values retrieved from the sputum and saliva samples 3502. The COVID symptoms of person 3503 may be respiratory symptoms (cough, sputum, shortness of breath, fever, anosmia (loss of smell), ageusia (loss of taste), nasal congestion, runny nose, sore throat), musculoskeletal symptoms (muscle pain, joint pain, headache, fatigue), digestive symptoms (abdominal pain, vomiting, diarrhea), physiological diseases (diabetes, lung diseases, cardiovascular diseases, ischemia, hypertension.)

The transmission system 3505 transmit the symptom data values gathered from the sensors 3517-3520, and thereafter the central processing unit 3506 in communication with the transmission system 3505 collect the symptom data values. The central processing unit 3506 is a transmitting or monitored central processing unit which is connected through the transmission system 3505 to biosensors utilizing two different biological components 3513-3516 and sensors 3517-3520. In an aspect, the transmitting or monitored central processing unit will be connected to a transmission system 3505, e.g., standard telecommunication network, and thereafter the symptom data values will be delivered to the central processing unit 3506. The symptom data values are transferred by the sensors 3517-3520 using a secure encoded channel, and levels of encryption are applied to all data transfer. In another aspect, the "Covidometer" may further include the transmitting system central processing unit remote from the central processing unit 3506. For example, the transmitting system central processing unit may be installed on a collector (biochip) 3501.

The central processing unit 3506 is connected to a transmission system 3505, and thereafter all the symptom data values gathered by using the biosensors 3513-3516 and sensors 3517-3520 will be delivered to a server 3508. The server 3508 in communication with the central processing unit 3506 comprises the database 3509 with the gathered symptom data values and the database 3510 with predetermined symptom threshold values for SARS-CoV-2 virus strains: Alpha (lineage B.1.1.7), B.1.1.7 with E484K, Beta (lineage B.1.351), Gamma (lineage P.1), Delta (lineage B.1.617.2), Lambda (lineage C.37), Mu (lineage B.1.621), Epsilon (lineages B.1.429, B.1.427, CAL.20C), Zeta (lineage P.2), Theta (lineage P.3), Eta (lineage B.1.525), Iota (lineage B.1.526), Kappa (lineage B.1.617.1), Omicron (lineage B.1.1.529), Lineage B.1.1.207, Lineage B.1.1.317, Lineage B.1.616, Lineage B.1.618, Brazilian variant, Centaurus variant, Deltacron variant, etc.

A software application 3511 receives information and executing by the central processing unit 3506 within the server 3508 comprised the databases 3509 and 3510, on which steps are performed according to the algorithm to manipulate the databases 3509 and 3510 of medical data for detect tendencies within the symptom data values. One of the ordinary skills in the art will further understand the various programming languages that can be employed to create one or more the software applications 3511 designed to implement and perform the steps of the algorithm. For example, the software applications 3511 can be structured in an object-orientated format using an object-oriented language, such as Java, C++, or one or more other languages. Alternatively, the software applications 3511 can be structured in a procedure-orientated format using a procedural language, such as assembly, C, etc.

The algorithm to detect tendencies comprises the steps of: calculating the first differentials (positive or negative) by comparing the received values stored in the database 3509 to predetermined symptom threshold values for the first original SARS-CoV-2 virus strain stored in the database 3510, using the first differentials to detect the second mutated SARS-CoV-2 virus strain based on a correspondence of its symptoms to the first differentials, calculating the second differentials (positive or negative) by comparing the received values stored in the database 3509 to predetermined symptom threshold values for the second SARS-CoV-2 virus strain stored in the database 3510, creating a metric of differentials in which the first and second differentials are ordered in their values relative to symptoms of the first SARS-CoV-2 virus strain and symptoms of the second SARS-CoV-2 virus strain, comparing the metric to the predetermined metric that contains known values of differentials indicating that the person has contracted the first or second strain, determining a presence or absence of SARS-CoV-2 in a person 3503, outputting a result indicating a presence or absence of COVID disease in a person 3503 by using the means 3512.

In another embodiment of the present invention, the algorithm further comprises the steps of: creating the metric of differentials, analyzing the metric of differentials to detect tendencies indicative of relationships between the differentials within the metric, determining if the person has the first SARS-CoV-2 virus strain or the second SARS-CoV-2 virus strain when at least one detected tendency indicates the person 3503 has contracted the first or second virus strain, outputting a result indicating a presence or absence of COVID disease in a person 3503 by using the means 3512.

Means 3512 outputs a result indicating a presence or absence of COVID disease in a person 3503. Means 3512 for outputting a result are an electronic device (such as a liquid-crystal display (LCD)) or part of a device (such as the screen of a tablet) that presents the result in visual form for patient 3503. Means 3512 can be any piece of computer hardware equipment which converts information into a human-perceptible form, such as text, graphics, audio, or video. Examples of means 3512 include monitors (e.g., a computer monitor or studio monitor), speakers (e.g., computer speakers), headphones, projectors (e.g., a LED projector), printers (e.g., inkjet printers, laser printers, thermal printers, dot matrix printers), tactile displays, braille displays, terminals for outputting information (e.g., a monochromatic terminal), punched cards, etc. It should be understood that other and further modifications of the "Covidometer," apart from those shown or suggested herein, may be made within the spirit and scope of the present invention.

Figure 36:
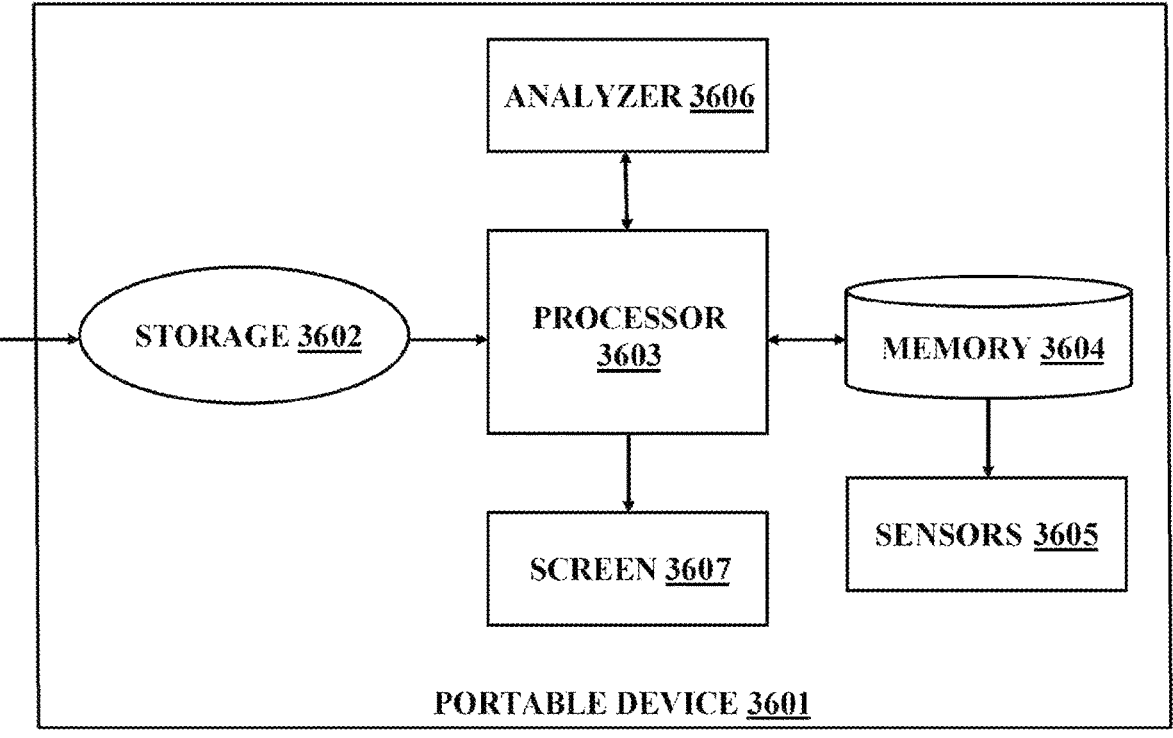
FIG. 36 is a diagram illustrating hardware components for implementing the device of the "Covidometer."

FIG. 36 is a diagram illustrating hardware components for implementing the device of the "Covidometer." The system for detecting COVID variants of the present invention can be implemented in the device of the "Covidometer" that determines if a person has a viral disease of a first original COVID-19 virus strain or second mutated COVID variant and requires no lab work. The "Covidometer" of FIG. 36 is the small, portable battery powered device 3601 with computing resources in the form of a storage 3602 for sputum and saliva samples (e.g., a box for biological materials), processor 3603, memory device 3604 with the sensors 3605 integrated into the memory device 3604, analyzer 3606 to detect tendencies, screen 3607, and it can determine at home whether a person has contracted COVID disease.

Figure 37:
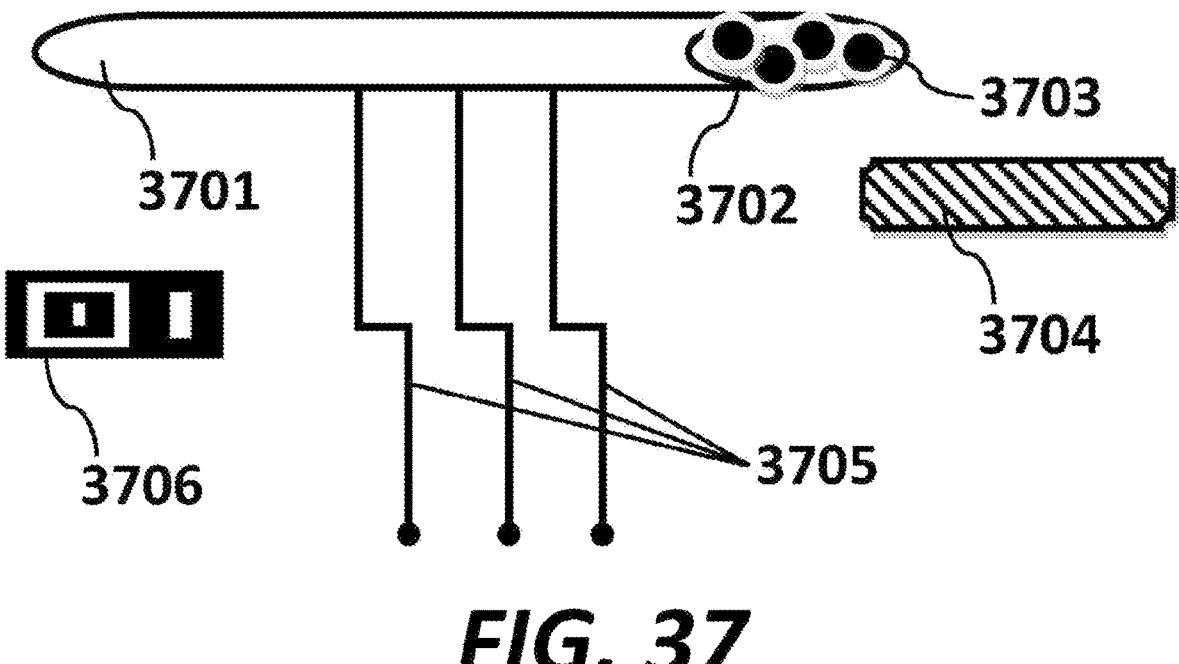
FIG. 37 is a diagram illustrating an example of the operation of the device of the "Covidometer."
Figure 38:
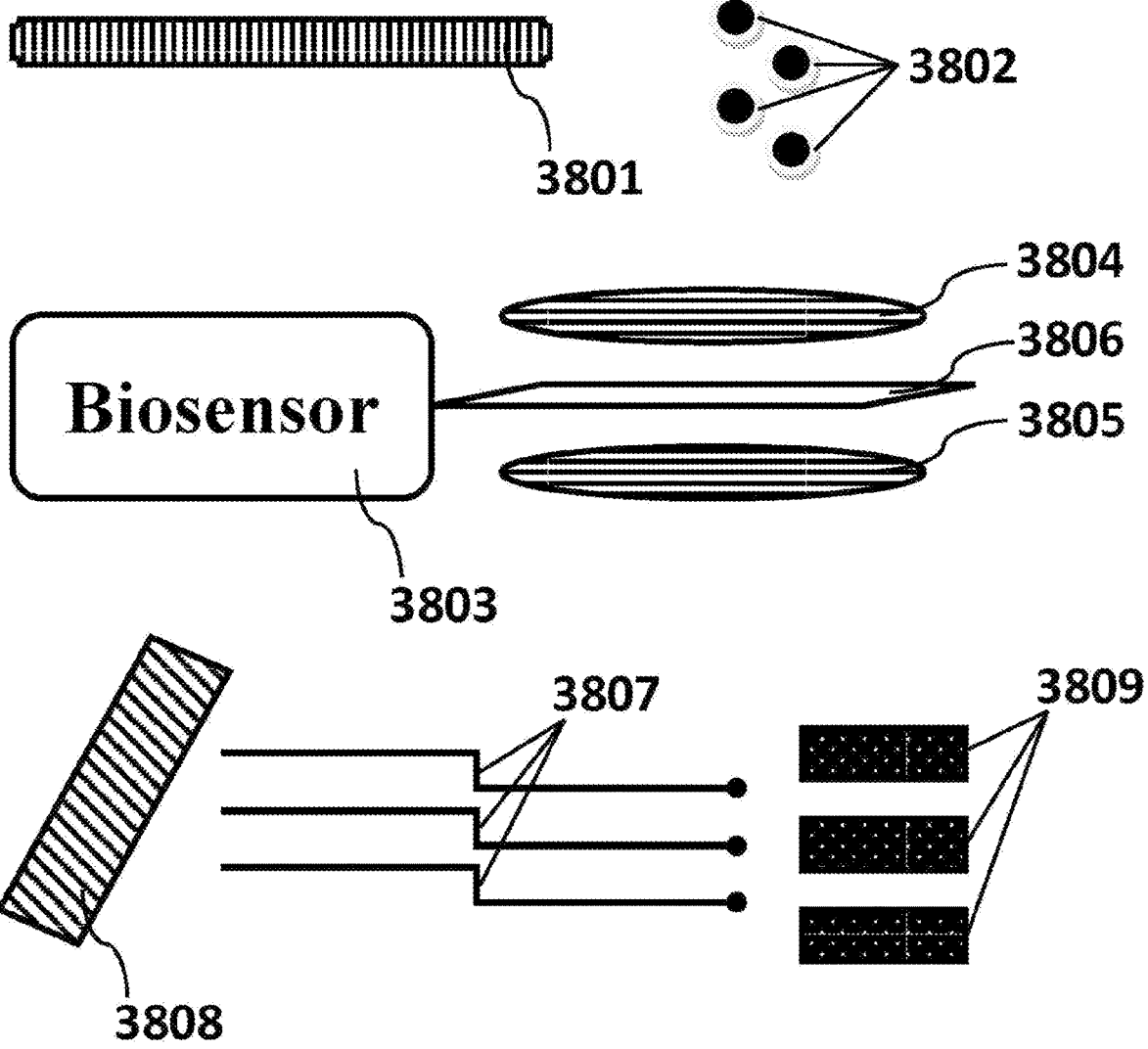
FIG. 38 is a diagram illustrating another example of the operation of the device of the "Covidometer."

FIGS. 37-38 illustrate examples of the operation of the device of the "Covidometer." As shown in FIG. 37, the "Covidometer" for detecting SARS-CoV-2 in sputum and saliva samples is based on magnetic particle spectroscopy technology (MPS). The "Covidometer" has a tube 3701 containing tiny magnetic iron oxide nanoparticles 3702 suspended in a liquid. Magnetic nanoparticles 3702 are coated with molecules, such as antibodies 3703, that recognize and attach to pieces of protein unique to the SARS-CoV-2 virus strain. The "Covidometer" testing involves taking sputum and saliva samples from a person and mixing them with two biological components of the biosensor 3704 utilizing two different biological components, which destroy any viral particles. This releases viral proteins and genetic material (RNA) and makes these viral targets accessible to antibodies 3703.

The "Covidometer" then applies a magnetic field to the tube 3701. One part of each viral protein will stick to the specific antibody 3703 on the surface of the magnetic nanoparticle 3702, and the other part will hang freely. The dangling part can stick to another antibody 3703 on another magnetic nanoparticle 3702, turning the protein into a bridge holding the two magnetic nanoparticles together. As this process is repeated, clumps of magnetic nanoparticles are formed, causing the magnetic signals 3705 emanating from the tube 3701 to weaken, that is detected by detectors 3706 (e.g., detectors integrated into the memory device of the "Covidometer") and gives a positive test result by the "Covidometer."

In another embodiment of the present invention, the basis of the "Covidometer" is a silicon chip with two electrodes, a nanowire or nanoribbon, onto which antibodies 3703 are applied. The principle of operation of the "Covidometer" is similar to the example noted above, but is based on recording signals of electric current flowing through the nanowire or nanoribbon. When viral protein particles of sputum or saliva enter the "Covidometer", they bind to antibodies applied to the surface, what changes the electrical conductivity of the nanowire or nanoribbon, what is detected by detectors 3706 (e.g., detectors integrated into the memory device of the "Covidometer") and gives a positive test result by the "Covidometer."

FIG. 38 is a diagram illustrating another example of the operation of the device of the "Covidometer." The disposable test strip 3801 is inserted into the "Covidometer" for testing, which analyzes sputum and saliva samples. Sputum or saliva 3802 is applied to the end of the strip 3801 and the result appears on the screen of the "Covidometer" within seconds. To set up such a system for detecting SARS-CoV-2 in sputum and saliva samples 3802, the "Covidometer" uses a biosensor 3803 utilizing two different biological components, where proteins 3804 and antibodies 3805 are the first and second biological components, respectively, which are separated by a membrane 3806 within the biosensor 3803.

The antibodies 3805 bind specifically to the virus in sputum and saliva 3802, resulting in a series of chemical reactions to attach the antibodies 3805 to the strip 3801. Once inserted into the "Covidometer", the strip 3801 with proteins 3804 and antibodies 3805 is exposed to an electrical current 3807 generated by the internal circuit board 3808. If sputum or saliva 3802 applied to the strip 3801 contains SARS CoV-2, then the viral particles bind to the proteins 3804 and antibodies 3805, slightly deforming them in this process. These subtle movements create distortions in the electrical current 3807 (the more virus, the more distortion) what is detected by detectors 3809 (e.g., detectors integrated into the memory device of the "Covidometer") within the "Covidometer" into numerical values that appear on the screen of the "Covidometer."

In another embodiment of the present invention, the "Covidometer" of the present invention can detect not only the basic original SARS-CoV-2 virus strain, but also its derivative strains within sputum and saliva samples 3802, as it analyzes angiotensin, —converting enzyme 2 (ACE2), —a viral receptor that is common to all known major SARS-CoV-2 virus strains. To do this, the biosensor 3803 uses proteins 3804 that glow when mixed with virus components in sputum and saliva 3802. The protein constructs 3804 recognize specific molecules on the surface of a virus or antibody, bind to them, and then emit light as a result of a biochemical reaction. This optical signal is detected by detectors 3809 (e.g., detectors integrated into the memory device of the "Covidometer") what gives a positive test result by the "Covidometer."

All publications, patents, and patent documents referred to in this document are incorporated by reference herein in their entirety, as though individually incorporated by reference. While various embodiments of the present invention have been described above, it should be understood that they have been presented by way of example only, and not limitation, and therefore the examples and embodiments described herein are non-limiting examples.

A person skilled in the relevant art will recognize that other components and configurations may be used without parting from the spirit and scope of the embodiments. Furthermore, the various features of the embodiments described herein may be extracted and/or combined to form new embodiments, and each specific element includes all technical equivalents that operate in a similar manner to accomplish a similar purpose.

In the drawings and the description of the drawings herein, certain terminology is used for convenience only, and is not to be taken as limiting the embodiments of the present invention. References to "one embodiment," "an embodiment," etc., may indicate that the embodiment(s) of the invention so described may include a particular feature, structure, or characteristic, but not every embodiment necessarily includes the particular feature, structure, or characteristic.

The terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. Also, in the following claims, the terms "including" and "comprising" are open-ended, that is, a system, device, article, or process that includes elements in addition to those listed after such a term in a claim are still deemed to fall within the scope of that claim.

Having thus described a preferred embodiment, it should be apparent to those skilled in the art that certain advantages of the described method and apparatus have been achieved.

It should also be appreciated that various modifications, adaptations, and alternative embodiments thereof may be made within the scope and spirit of the present invention.

What is claimed is:

1. A system for detecting a target biological agent in a sputum sample obtained from a person, the system comprising:

(a) a protein biosensor configured to:

interact with the sputum sample;

contain two different biological components, wherein:

the first biological component and the second biological component are coupled to the same transducer within the protein biosensor;

the first biological component and the second biological component are separated from each other by a membrane within the protein biosensor; and the first biological component comprises proteins;

output both the first signal and the second signal, respectively, when the first biological component and the second biological component change the chemical structure of the sputum sample;

(b) a wireless communication device;

(c) a memory device having one or more integrated detectors, the memory device being configured to:

receive a first signal and a second signal from the protein biosensor via the one or more integrated detectors, wherein the one or more integrated detectors are embedded within the memory device and are configured to convert the first or the second signal into corresponding values;

include a memory device controller that is coupled to each of the one or more integrated detectors, wherein the memory device controller is configured to set a first signal threshold and a second signal threshold for each of the one or more integrated detectors;

transmit an indication, via the wireless communication device, to another device responsive to a determination that a value detected by the one or more integrated detectors is greater than or less than the first signal threshold; and, transmit an indication, via the wireless communication device, to another device responsive to a determination that a value detected by the one or more integrated detectors is greater than or less than the second signal threshold;

wherein the first signal threshold and the second signal threshold are predetermined calibration levels correlating to a presence of the target biological agent, such that the indication is specific to the target biological agent in the person.

2. The system of claim 1, wherein the membrane that separates the two biological components from each other within the protein biosensor is a semi-permeable membrane.

3. The system of claim 1, wherein:

at least one of the one or more integrated detectors are configured to perform electrical, magnetic or optical measurements; and the memory device is further configured to update the first and second signal thresholds for each of the one or more integrated detectors based on the detected change in the electrical, magnetic, or optical characteristics of the sputum sample.

4. The system of claim 1, wherein:

at least one of the one or more integrated detectors contains a detector that measures temperature or relative molecular motion; and the memory device is further configured to update the first and second signal thresholds for each of the one or more integrated detectors based on the detected change in the characteristics of temperature or relative molecular motion of the sputum sample.

5. The system of claim 1, wherein the indication identifies the presence of SARS-CoV-2 in the person when the first signal threshold or the second signal threshold for each of the one or more integrated detectors is set to a limit threshold for a SARS-CoV-2 virus strain; and, wherein the first signal threshold and the second signal threshold are predetermined calibration levels correlating to the presence of a first and second SARS-CoV-2 strain, respectively, such that the indication is specific to the first and second SARS-CoV-2 strains in the person.

6. The system of claim 5, wherein:

the concentration of the first biological component corresponds to the concentration for the first SARS-CoV-2 virus strain and the concentration of the second biological component corresponds the concentration for the second SARS-CoV-2 virus strain;

the concentrations of the first and second biological component are specific component's volume within the analyte derived from data obtained using samples confirmed to contain SARS-CoV-2 within the analyte; and the memory device identifies that the person has contracted the first SARS-CoV-2 virus strain or the second SARS-CoV-2 virus strain in response to one or more integrated detectors detecting a value that is greater than or less than the first signal threshold or the second signal threshold, respectively.

7. The system of claim 1, wherein:

the first and second biological components, when interacting with the sample, do not capture different parts of the target substance to form a sandwich complex; and no complex is formed within the sputum sample in which the target substance is sandwiched between the first and second biological components.

8. The system of claim 1, wherein the internal membrane:

is located between the first and second biological components and functions as a physical barrier there between; and has a first contact surface with the first biological component and a second contact surface with the second biological component.

9. The system of claim 1, wherein, in response to detected changes in the sample, the memory device controller updates the threshold criteria for the first and second signals for each of the integrated detectors.

10. The system of claim 1, wherein:

the sputum sample obtained from a person comprises at least one of sputum, saliva, a nasal swab, a nasopharyngeal swab, an oropharyngeal swab, a throat swab, or deep airway material; and the protein biosensor is configured to interact with at least one of sputum, saliva, a nasal swab, a nasopharyngeal swab, an oropharyngeal swab, a throat swab, or deep airway material, respectively.

11. A system for detecting a target biological agent in a sample, the system comprising:

(a) a protein biosensor comprising a semipermeable membrane within the biosensor, a first biological component immobilized on one side of the membrane, and a second biological component immobilized on an opposite side of the membrane, wherein the first and second biological components are different and are both coupled to a same transducer of the biosensor, the protein biosensor being configured to interact with a sample obtained from a person such that an interaction between the first biological component and the target biological agent produces a first signal and an interaction between the second biological component and the target biological agent produces a second signal;

(b) one or more detectors integrated into a memory device and configured to receive the first signal and second signal from the protein biosensor and convert the signals into corresponding values, the memory device including a memory device controller;

(c) the memory device controller configured to set threshold criteria for the first signal and the second signal and to generate an indication when the corresponding value exceeds a respective threshold criterion or the corresponding value is less than a respective threshold criterion; and (d) a wireless communication device operably coupled to the memory device and configured to transmit the indication to an external device;

wherein the semipermeable membrane prevents direct contact between the first biological component and the second biological component while permitting the sample to contact both components, thereby allowing the system to distinguish the presence of the target biological agent based on both the first signal and the second signal;

wherein the protein biosensor is configured such that the first and second biological components, when interacting with the sample, do not capture different parts of the same target biological agent to form a sandwich complex, and no complex is formed in which the target biological agent is sandwiched between the first and second biological components.

12. The system of claim 11, wherein:

the sample comprises at least one of sputum, saliva, a nasal swab, a nasopharyngeal swab, an oropharyngeal swab, a throat swab, or deep airway material; and the protein biosensor is configured to interact with at least one of sputum, saliva, a nasal swab, a nasopharyngeal swab, an oropharyngeal swab, a throat swab, or deep airway material.

*     *     *     *     *